US008450106B2

(12) United States Patent
Kaur et al.

(10) Patent No.: US 8,450,106 B2
(45) Date of Patent: May 28, 2013

(54) ONCOLYTIC VIRUS

(75) Inventors: Balveen Kaur, Dublin, OH (US); Antonio Chiocca, Powell, OH (US); Yoshinaga Saeki, Toyama (JP)

(73) Assignee: The Ohio State University Research Foundation, Columbus, OH (US)

( * ) Notice: Subject to any disclaimer, the term of this patent is extended or adjusted under 35 U.S.C. 154(b) by 410 days.

(21) Appl. No.: 12/697,891

(22) Filed: Feb. 1, 2010

(65) Prior Publication Data
US 2010/0272686 A1    Oct. 28, 2010

Related U.S. Application Data

(63) Continuation of application No. PCT/US2008/080367, filed on Oct. 17, 2008.

(60) Provisional application No. 61/256,644, filed on Oct. 30, 2009, provisional application No. 61/148,870, filed on Jan. 30, 2009, provisional application No. 60/980,664, filed on Oct. 17, 2007.

(51) Int. Cl.
  *C12N 15/79* (2006.01)
  *C12N 15/869* (2006.01)
(52) U.S. Cl.
  USPC ........................................... 435/320.1
(58) Field of Classification Search
  None
  See application file for complete search history.

(56) References Cited

U.S. PATENT DOCUMENTS

| | | | |
|---|---|---|---|
| 4,683,202 A | 7/1987 | Mullis | |
| 5,928,906 A | 7/1999 | Köster et al. | |
| 6,214,613 B1 | 4/2001 | Higuchi et al. | |
| 6,379,674 B1 | 4/2002 | Rabkin et al. | |
| 6,432,700 B1 | 8/2002 | Henderson et al. | |
| 6,573,099 B2 | 6/2003 | Graham | |
| 7,052,872 B1 | 5/2006 | Hansen et al. | |
| 7,074,405 B1 | 7/2006 | Hansen et al. | |
| 7,138,103 B2 | 11/2006 | Goldenberg et al. | |
| 7,186,409 B2 | 3/2007 | Snyder et al. | |
| 7,553,950 B2 | 6/2009 | Prabhakar et al. | |
| 2003/0039656 A1 | 2/2003 | Tarrand et al. | |
| 2003/0185832 A1 | 10/2003 | Thorpe et al. | |
| 2004/0003435 A1 | 1/2004 | Baszczynski et al. | |
| 2004/0009604 A1 | 1/2004 | Zhang et al. | |
| 2004/0105844 A1* | 6/2004 | Federoff et al. | 424/93.2 |
| 2004/0258667 A1* | 12/2004 | Whitley et al. | 424/93.2 |
| 2005/0163758 A1 | 7/2005 | Chiocca et al. | |
| 2006/0057553 A1 | 3/2006 | Aguilar-Cordova | |
| 2006/0099224 A1 | 5/2006 | Kirn | |
| 2006/0147420 A1 | 7/2006 | Fueyo et al. | |
| 2007/0134202 A1 | 6/2007 | Hamada et al. | |
| 2007/0141705 A1 | 6/2007 | Inoue et al. | |
| 2008/0008686 A1 | 1/2008 | Yao | |
| 2008/0081032 A1 | 4/2008 | Morris et al. | |
| 2008/0206199 A1 | 8/2008 | Cassady et al. | |
| 2008/0292592 A1 | 11/2008 | Chada et al. | |
| 2009/0117644 A1 | 5/2009 | Yazaki et al. | |
| 2009/0215147 A1 | 8/2009 | Zhang et al. | |
| 2009/0220460 A1 | 9/2009 | Coffin | |
| 2010/0086522 A1 | 4/2010 | Bell et al. | |

FOREIGN PATENT DOCUMENTS

WO    2008/012695 A2    1/2008

OTHER PUBLICATIONS

Abdallah, B.M. et al., The Use of Mesenchymal (Skeletal) Stem Cells for Treatment of Degenerative Diseases: Current Status and Future Prespectives, Journal of Cellular Physiology, 2009, pp. 9-12, 218.

Aboody, K.S. et al., Neural stem cells display extensive tropism for pathology in adult brain: Evidence from intracranial gliomas, PNAS, Nov. 7, 2000, pp. 12846-12851, 97(23).

Aboody, K.S. et al., Stem and progenitor cell-mediated tumor selective gene therapy, Gene Therapy, 2008, pp. 739-752, 15.

Abordo-Adesida, E. et al., Stability of Lentiviral Vector-Mediated Transgene Expression in the Brain in the Presence of Systemic Antivector Immune Responses, Hum Gene Ther., 2005, pp. 741-751, 16(6).

Abremski, K. et al., Bacteriophage P1 Site-specific Recombination, The Journal of Biological Chemistry, Feb. 10, 1984, pp. 1509-1514, 259(3).

Aghi, M. et al., Synergistic Anticancer Effects of Ganciclovir/Thymidine Kinase and 5-Fluorocytosine/Cytosine Deaminase Gene Therapies, Journal of the National Cancer Institute, Mar. 4, 1998, pp. 370-380, 90(5).

Aghi, M. et al., Multimodal Cancer Treatment Mediated by a Replicating Oncolytic Virus That Delivers the Oxazaphosphorine/Rat Cytochrome P450 2B1 and Ganciclovir/Herpes Simplex Virus Thymidine Kinase Gene Therapies, Cancer Research, Aug. 15, 1999, pp. 3861-3865, 59.

Aghi, M. et al., Oncolytic viral therapies—the clinical experience, Oncogene, 2005, pp. 7802-7816, 24.

Aghi, M. et al., Tumor Stromal-Derived Factor-1 Recruits Vascular Progenitors to Mitotic Neovasculature, where Microenvironment Influences Their Differentiated Phenotypes, Cancer Res, Sep. 15, 2006, pp. 9054-9064, 66(18).

Aghi, M. et al., Angiogenic Response Caused by Oncolytic Herpes Simplex Virus-Induced Reduced Thrombospondin Expression Can Be Prevented by Specific Viral Mutations or by Administering a Thrombospondin-Derived Peptide, Cancer Res, Jan. 15, 2007, pp. 440-444, 67(2).

(Continued)

*Primary Examiner* — Michael Burkhart
(74) *Attorney, Agent, or Firm* — Standley Law Group LLP

(57) ABSTRACT

Malignant tumors that are intrinsically resistant to conventional therapies are significant therapeutic challenges. An embodiment of the present invention provides an oncolytic virus capable of killing target cells, such as a tumor cells. In various embodiments presented herein, the oncolytic virus is armed or encodes a therapeutic polypeptide. In at least one embodiment, a recombinant oncolytic virus has been generated that can specifically replicate in cancer cells leading to their destruction and at the same time secrete robust amounts of a therapeutic polypeptide. Compositions and methods disclosed herein have broad therapeutic applicability.

5 Claims, 19 Drawing Sheets
(2 of 19 Drawing Sheet(s) Filed in Color)

OTHER PUBLICATIONS

Aghi, M. et al., Oncolytic herpes virus with defective ICP6 specifically replicates in quiescent cells with homozygous genetic mutations in p16, Oncogene, 2008, pp. 4249-4254, 27.

Al, J. et al., The inositol phosphatase SHIP-2 down-regulated FcγR-mediated phagocytosis in murine mactophases independently of SHIP-1, Blood, Jan. 15, 2006, pp. 813-820, 107(2).

Akanitapichat, P. et al., 1,3-Dihydroxyacridone derivatives as inhibitors of herpes virus replication, Antiviral Research, 2000, pp. 123-134, 45.

Akhter, A. et al., Caspase-7 Activation by the Nlrc4/Ipaf Inflammasome Restricts *Legionella pneumophila* Infection, PLoS Pathogens, Apr. 2009, pp. 1-13, 5(4).

Albert, H. et al., Site-specific integration of DNA into wild-type and mutant lox sites placed in the plant genome, The Plant Journal, 1995, pp. 649-659, 7(4).

Ali, S. et al., Combined Immunostimulation and Conditional Cytotoxic Gene Therapy Provide Long-term Survival in a Large Glioma Model, Cancer Res, Aug. 15, 2005, pp. 7194-7204, 65(16).

Allen, J.C. et al., Brain Tumors in Children: Current Cooperative and Institutional Chemotherapy Trials in Newly Diagnosed and Recurrent Disease, Seminars in Oncology, Mar. 1986, pp. 110-122, 13(1).

Altschul, S.F. et al., Basic Local Alignment Search Tool, J. Mol. Biol., 1990, pp. 403-410, 215.

Altschul, S.F. et al., Gapped BLAST and PSI-BLAST: a new generation of protein database search programs, Nucleic Acids Research, 1997, pp. 3389-3402, 25(17).

Alvarez-Breckenridge, C. et al., Pharmacologic and Chemical Adjuvants in Tumor Virotherapy, Chem Rev., Jul. 2009, pp. 3125-3140, 109(7).

Andreansky, S. et al., Evaluation of Genetically Engineered Herpes Simplex Viruses as Oncolytic Agents for Human Malignant Brain Tumors, Cancer Research, Apr. 15, 1997, pp. 1502-1509, 57.

Andreansky, S. et al., Treatment of intracranial gliomas in immunocompetent mice using herpes simplex viruses that express murine interleukins, Gene Therapy, 1998, pp. 121-130, 5.

Arslan, F. et al., The role of versican isoforms V0/V1 in glioma migration mediated by transforming growth factor-β2, British Journal of Cancer, 2007, pp. 1560-1568, 96.

Avery, A.M. et al., Substrate specificity of ultraviolet DNA endonuclease (UVDE/Uve1p) from *Schizosaccharomyces pombe*, Nucleic Acids Research, 1999, pp. 2256-2264, 27(11).

Ayoub, S.S. et al., Acetaminophen-induced hypothermia in mice is mediated by a prostaglandin endoperoxide synthase 1 gene-derived protein, PNAS, Jul. 27, 2004, pp. 11165-11169, 101(30).

Babic, A.M. et al., CYR61, a product of a growth factor-inducible immediate early gene, promotes angiogenesis and tumor growth, Proc. Natl. Acad. Sci. USA, May 1998, pp. 6355-6360, 95.

Balachandran, S. et al., Defective translational control facilitates vesicular stomatitis virus oncolysis, Cancer Cell, Jan. 2004, pp. 51-65, 5.

Baran, C.P. et al., The Inositol 5'-Phosphatase SHIP-1 and the Src Kinase Lyn Negatively Regulate Macrophage Colony-stimulating Factor-induced Akt Activity, The Journal of Biological Chemistry, Oct. 3, 2003, pp. 38628-38636, 278(40).

Barber, G.N., The dsRNA-dependent protein kinase, PKR and cell death, Cell Death and Differentiation, 2005, pp. 563-570, 12.

Barth, R.F. et al., Rat brain tumor models in experimental neuro-oncology: the C6, 9L, T9, RG2, F98, BR4C, RT-2, and CNS-1 gliomas, J Neurooncol, 2009, pp. 299-312, 94.

Behin, A. et al., Primary brain tumours in adults, The Lancet, Jan. 25, 2003, pp. 323-331, 361.

Bellail, A.G. et al., Microregional extracellular matrix heterogeneity in brain modulates glioma cell invasion, The International Journal of Biochemistry & Cell Biology, 2004, pp. 1046-1069, 36.

Benedetti, S. et al., Gene therapy of experimental brain tumors using neural progenitor cells, Nature Medicine, Apr. 2000, pp. 447-450, 6(4).

Bennett, J.J. et al., Interleukin 12 Secretion Enhances Antitumor Efficacy of Oncolytic Herpes Simplex Viral Therapy for Colorectal Cancer, Annals of Surgery, Jun. 2001, pp. 819-826, 233(6).

Bergelson, J.M. et al., Isolation of a Common Receptor for Coxsackie B Viruses and Adenoviruses 2 and 5, Science, Feb. 28, 1997, pp. 1320-1323, 275.

Bexell, D. et al., Bone Marrow Multipotent Mesenchymal Stroma Cells Act as Pericyte-like Migratory Vehicles in Experimental Gliomas, Molecular Therapy, Jan. 2009, pp. 183-190, 17(1).

Bhaumik, S. et al., Optical imaging of *Renilla luciferase* reporter gene expression in living mice, PNAS, Jan. 8, 2002, pp. 377-382, 99(1).

Biglari, A. et al., Effects of ectopic decorin in modulating intracranial glioma progression in vivo, in a rat syngeneic model, Cancer Gene Ther., Nov. 2004, pp. 721-732, 11(11).

Bischof, G. et al., Effects of extracellular pH on intracellular pH-regulation and growth in a human colon carcinoma cell-line, Biochimica et Biophysica Acta, 1996, pp. 131-139, 1282.

Bleyer, W.A., The Impact in the United States and the World of Central Nervous System Cancer During Childhood, Pediatric Neuro-Oncology, 1992, pp. 1-7, 3.

Boehmer, P.E. et al., Herpes Simplex Virus DNA Replication, Annu. Rev. Biochem., 1997, pp. 347-384, 66.

Borovjagin, A.V. et al., Complex mosaicism is a novel approach to infectivity enhancement of adenovirus type 5-based vectors, Cancer Gene Therapy, 2005, pp. 475-486, 12.

Bosch, P. et al., Efficient Adenoviral-Mediated Gene Delivery into Porcine Mesenchymal Stem Cells, Molecular Reproduction and Development, 2006, pp. 1393-1403, 73.

Boviatsis, E.J. et al., Gene Transfer into Experimental Brain Tumors Mediated by Adenovirus, Herpes Simplex Virus, and Retrovirus Vectors, Human Gene Therapy, 1994, pp. 183-191, 5.

Boviatsis, E.J. et al., Long-Term Survival of Rats Harboring Brain Neoplasms Treated with Ganciclovir and a Herpes Simplex Virus Vector That Retains and Intact Thymidine Kinase Gene, Cancer Research, Nov. 15, 1994, pp. 5745-5751, 54.

Bradbury, E.J. et al., Chondroitinase ABC promotes functional recovery after spinal cord injury, Nature, Apr. 11, 2002, pp. 636-640, 416.

Brat, D.J. et al., Gentic and Biologic Progression in Astrocytomas and Their Relation to Angiogenic Dysregulation, Advances in Anatomic Pathology, 2002, pp. 24-36, 9(1).

Brat, D.J. et al., Pseudopalisades in Glioblastoma Are Hypoxic, Express Extracellular Matrix Proteases, and Are Formed by an Actively Migrating Cell Population, Cancer Research, Feb. 1, 2004, pp. 920-927, 64.

Breidenbach, M. et al., Genetic Replacement of the Adenovirus Shaft Fiber Reduces Liver Tropism in Ovarian Cancer Gene Therapy, Human Gene Therapy, May 2004, pp. 509-518, 15.

Breitbach, C.J. et al., Targeted Inflammation During Oncolytic Virus Therapy Severely Compromises Tumor Blood Flow, Molecular Therapy, Sep. 2007, pp. 1686-1693, 15(9).

Brem, S.S. et al., Central Nervous System Cancers, Journal of the National Comprehensive Cancer Network, May 2008, pp. 456-504, 6(5).

Broach, J.R. et al., Recombination within the Yeast Plasmid 2μ Circle is Site-Specific, Cell, May 1982, pp. 227-234, 29.

Brown, A.B. et al., Intravascular Delivery of Neural Stem Cell Lines to Target Intracranial and Extracranial Tumors of Neural and Non-Neural Origin, Human Gene Therapy, Dec. 10, 2003, pp. 1777-1785, 14.

Brückner, G. et al., Acute and long-lasting changes in extracellular-matrix chondroitin-sulphate proteoglycans induced by injection of chondroitinase ABC in the adult rat brain, Exp Brain Res, 1998, pp. 300-310, 121.

Brückner, G. et al., Postnatal Development of Perineuronal Nets in Wild-Type Mice and in a Mutant Deficient in Tenascin-R, The Journal of Comparative Neurology, 2000, pp. 616-629, 428.

Burns, T.C. et al., Stem Cells for Ischemic Brain Injury: A Critical Review, The Journal of Comparative Neurology, 2009, pp. 125-144, 515.

Busch, S.A. et al., The role of extracellular matrix in CNS regeneration, Current Opinion in Neurobiology, 2007, pp. 120-127, 17.

Butchar, J.P. et al., *Francisella tularensis* Induces IL-23 Production in Human Monocytes, The Journal of Immunology, 2007, pp. 4445-4454.

Butchar, J.P. et al., IFNγ enhances IL-23 production during *Francisella* infection of human monocytes, FEBS Lett., Apr. 2, 2008, pp. 1044-1048, 582(7).
Butchar, J.P. et al., Microarray Analysis of Human Monocytes Infected with *Francisella tularensis* Identifies New Targets of Host Response Subversion, PLoS One, Aug. 2008, pp. 1-8, 3(8).
Cao, X. et al., The Inositol 3-Phosphatase PTEM Negatively Regulates Fcy Receptor Signaling, but Supports Toll-Like Receptor 4 Signaling in Murine Peritoneal Macrophages, The Journal of Immunology, 2004, pp. 4851-4857.
Carmeliet, P. et al., Angiogenesis in cancer and other diseases, Nature, Sep. 14, 2000, pp. 249-257, 407.
Carroll, N.M. et al., Enhancement of Gene Therapy Specificity for Diffuse Colon Carcinoma Liver Metastases with Recombinant Herpes Simplex Virus, Annals of Surgery, Sep. 1996, pp. 323-330, 224(3).
Carroll, N.M. et al., The Effect of Ganciclovir on Herpes Simplex Virus-Mediated Oncolysis, Journal of Surgical Research, 1997, pp. 413-417, 69.
Chacko, G.W. et al., Negative Signaling in B Lymphocytes Induces Tyrosine Phosphorylation of the 145-kDa Inositol Polyphosphate 5-Phosphatase, SHIP1, The Journal of Immunology, 1996, pp. 2234-2238.
Chang, H-M. et al., Induction of interferon-stimulated gene expression and antiviral responses require protein deacetylase activity, PNAS, Jun. 29, 2004, pp. 9578-9583, 101(26).
Chase, M. et al., An oncolytic viral mutant that delivers the CYP2B1 transgene and augments cyclophosphamide chemotherapy, Nature Biotechnology, May 1998, pp. 444-448, 16.
Chi, M. et al., C-Reactive Protein Induces Signaling Through FcγRIIa on HL-60 Granulocytes, The Journal of Immunology, 2002, pp. 1413-1418.
Chiocca, E.A. et al., Transfer and Expression of the lacZ Gene in Rat Brain Neurons Mediated by Herpes Simplex Virus Mutants, The New Biologist, Aug. 1990, pp. 739-746, 2(8).
Chiocca, E.A. et al., Guided genes for tumor warfare, Nature Biotechnology, Mar. 2002, pp. 235-236, 20.
Chiocca, E.A. et al., Oncolytic Viruses, Nature Reviews, Dec. 2002, pp. 938-951, 2.
Chiocca, E.A. et al., A Phase I Open-Label, Dose-Escalation, Multi-Institutional Trial of Injection with an E1B-Attenuated Adenovirus, ONYX-015, into the Peritumoral Region of Recurrent Malignant Gliomas, in the Adjuvant Setting, Molecular Therapy, Nov. 2004, pp. 958-966, 10(5).
Chiocca, E.A. et al., A Phase I Trial of Ad.hIFN-β Gene Therapy for Glioma, Molecular Therapy, Mar. 2008, pp. 618-626, 16(3).
Chou, J. et al., Association of a Mr 90,000 phosphoprotein with protein kinase PKR in cells exhibiting enhanced phosphorylation of translation initiation factor eIF-2α and premature shutoff of protein synthesis after infection with γ134.5—mutants of herpes simplex virus 1, Proc. Natl. Acad. Sci. USA, Nov. 1995, pp. 10516-10520, 92.
Chung, R.Y. et al., B-myb Promoter Retargeting of Herpes Simplex Virus γ34.5 Gene-Mediated Virulence toward Tumor and Cycling Cells, Journal of Virology, Sep. 1999, pp. 7556-7564, 73(9).
Coffey, M.C. et al., Reovirus Therapy of Tumors with Activated Ras Pathway, Science, Nov. 13, 1998, pp. 1332-1334, 282.
Conrad, C. et al., Δ24-hyCD adenovirus suppresses glioma growth in vivo by combining oncolysis and chemosensitization, Cancer Gene Therapy, 2005, pp. 284-294, 12.
Contag, P.R. et al., Bioluminescent indicators in living mammals, Nature Medicine, Feb. 1998, pp. 245-247, 4(2).
Contag, P.R. et al., Advances in Vivo Bioluminescence Imaging of Gene Expression, Annu. Rev. Biomed. Eng., 2002, pp. 235-260, 4.
Cook, S.H. et al., Luciferase Imaging of a Neurotropic Viral Infection in Intact Animals, Journal of Virology, May 2003, pp. 5333-5338, 77(9).
Coukos, G. et al., Use of Carrier Cells to Deliver a Replication-selective Herpes Simplex Virus-1 Mutant for the Intraperitoneal Therapy of Epithelial Ovarian Cancer, Clinical Cancer Research, Jun. 1999, pp. 1523-1537, 5.
Cox, M.M. et al., The FLP protein of the yeast 2-μm plasmid: Expression of a eukaryotic genetic recombination system in *Escherichia coli*, Proc. Natl. Acad. Sci. USA, Jul. 1983, pp. 4223-4227, 80.

Cremer, T.J. et al., Effective host response to *Francisella tularensis* requires functional mast cells, Future Microbiol, Oct. 2008, pp. 503-506, 3.
Cremer, T.J. et al., *Francisella tularensis* regulates autophagy-related host cell signaling pathways, Autophagy, Jan. 2009, pp. 125-128, 5(1).
Crespo, D. et al., How does chondroitinase promote functional recovery in the damaged CNS?, Experimental Neurology, 2007, pp. 159-171, 206.
Crouser, E.D. et al., Monocyte Activation by Necrotic Cells is Promoted by Mitochondrial Proteins and Formyl Peptide Receptors, Crit Care Med., Jun. 2009, pp. 2000-2009, 37(6).
Csatary, L.K. et al., Use of Newcastle Disease Virus Vaccine (MTH-68/H) in a Patient With High-grade Glioblastoma, JAMA, May 5, 1999, pp. 1585-1589, 284.
Csatary, L.K. et al., MTH-68/H oncolytic viral treatment in human high-grade gliomas, Journal of Neuro-Oncology, 2004, pp. 83-93, 67.
Culver, K.W. et al., In Vivo Gene Transfer with Retroviral Vector-Producer Cells for Treatment of Experimental Brain Tumors, Science, Jun. 12, 1992, pp. 1550-1552, 256.
Currier, M.A. et al., Efficacy and Safety of the Oncolytic Herpes Simplex Virus rRp450 Alone and Combined With Cyclophosphamide, Mol Ther., May 2008, pp. 879-885, 16(5).
Cutter, J.L. et al., Gene therapeutics: the future of brain tumor therapy?, Expert Rev. Anticancer Ther., 2006, pp. 1053-1064, 6(7).
Dahlstrand, J. et al., Expression of the Class VI Intermediate Filament Nestin in Human Central Nervous System Tumors, Cancer Research, Oct. 1, 1992, pp. 5334-5341, 52.
Danks, M.K. et al., Overexpression of a Rabbit Liver Carboxylesterase Sensitizes Human Tumor Cells to CPT-11, Cancer Research, Jan. 1, 1998, pp. 20-22, 58.
Danks, M.K. et al., Comparison of Activation of CPT-11 by Rabbit and Human Carboxylesterases for Use in Enzyme/Prodrug Therapy, Clinical Cancer Research, Apr. 1999, pp. 917-924. 5.
Deisboeck, T.S. et al., Development of a novel non-human primate model for preclinical gene vector safety studies. Determining the effects of intracerebral HSV-1 inoculation in the common marmoset: a comparative study, Gene Therapy, 2003, pp. 1225-1233, 10.
Delpech, B. et al., Hyaluronan and Hyaluronectin in the Extracellular Matrix of Human Brain Tumour Stroma, Eur J Cancer, 1993, pp. 1012-1017, 29A(7).
Dewhirst, M.W. et al., Cycling hypoxia and free radicals regulate angiogenesis and radiotherapy response, Nature Reviews, Jun. 2008, pp. 425-437, 8.
Dickens, D.S. et al., Therapeutic Strategies for Targeting Mononuclear Phagocytes in Cancer, J Pediatr Hematol Oncol, Jan. 2009, 31(1).
Dunn, I.F. et al., The Neurosurgeon as Local Oncologist: Cellular and Molecular Neurosurgery in Malignant Glioma Therapy, Neurosurgery, Jun. 2003, pp. 1411-1422, 52(6).
Ejercito, P.M. et al., Characterization of Herpes Simplex Virus Strains Differing in their Effects on Social Behaviour of Infected Cells, J. gen. Virol., 1968, pp. 357-364, 2.
Elliott, K. et al., The c-Myc-interacting adaptor protein Bin1 activates a caspase-independent cell death program, Oncogene, 2000, pp. 4669-4684, 19.
Fang, H. et al., Lipopolysaccharide-Induced Macrophage Inflammatory Response is Regulated by SHIP, The Journal of Immunology, 2004, pp. 360-366.
Fehrer, C. et al., Reduced oxygen tension attenuates differentiation capacity of human mesenchymal stem cells and prolongs heir lifespan, Aging Cell, 2007, pp. 745-757, 6.
Feil, R. et al., Ligand-activated site-specific recombination in mice, Proc. Natl. Acad. Sci. USA, Oct. 1996, pp. 10887-10890, 93.
Filipski, E. et al., Effects of Chronic Jet Lag on Tumor Progression in Mice, Cancer Research, Nov. 1, 2004, pp. 7879-7885, 64.
Finger, C. et al., Replicating retroviral vectors mediating continuous production and secretion of therapeutic gene products from cancer cells, Cancer Gene Therapy, 2005, pp. 464-474, 12.
Fisher, L.J., Neural Precursor Cells: Applications for the Study and Repair of the Central Nervous System, Neurobiology of Disease, 1997, pp. 1-22, 4.

Fouletier-Dilling, C.M. et al., Novel Compound Enables High-Level Adenovirus Transduction in the Absence of an Adenovirus-Specific Receptor, Human Gene Therapy, Nov. 2005, pp. 1287-1297, 16.
Frank, R.T. et al., Neural Stem Cells as a Novel Platform for Tumor-Specific Delivery of Therapeutic Antibodies, PLoS ONE, Dec. 2009, pp. 1-7, 4(12).
Friedman, A. et al., Glioma Virotherapy: Effects of Innate Immune Suppression and Increased Viral Replication Capacity, Cancer Res, Feb. 15, 2006, pp. 2314-2319, 66(4).
Friedman, H.S. et al., Schedule-dependent activity of irinotecan plus BCNU against malignant glioma xenografts, Cancer Chemother Pharmacol, 2000, pp. 345-349, 45.
Friedman, H.S. et al., The Emerging Role of Irinotecan (CPT-11) in the Treatment of Malignant Glioma in Brain Tumors, Cancer Supplement, May 1, 2003, pp. 2359-2362, 97(9).
Fu, X. et al., A strict-late viral promoter is a strong tumor-specific promoter in the context of an oncolytic herpes simplex virus, Gene Therapy, 2003, pp. 1458-1464, 10.
Fueyo, J. et al., A mutant oncolytic adenovirus targeting the Rb pathway produces anti-glioma effect in vivo, Oncogene, 2000, pp. 2-12, 19.
Fueyo, J. et al., Preclinical Characterization of the Antiglioma Activity of a Tropism-Enhanced Adenovirus Targeted to the Retinoblastoma Pathway, Journal of the National Cancer Institute, May 7, 2003, pp. 652-660, 95(9).
Fukushima, Y. et al., Brain-specific angiogenesis inhibitor 1 expression is inversely correlated with vascularity and distant metastasis of colorectal cancer, International Journal of Oncology, 1998, pp. 967-970, 13.
Fulci, G. et al., Initiation of Human Astrocytoma by Clonal Evolution of Cells with Progressive Loss of p53 Functions in a Patient with a 283H TP53 Germ-line Mutation: Evidence for a Precursor Lesion, Cancer Research, May 15, 2002, pp. 2897-2905, 62.
Fulci, G. et al., Cyclophosphamide enhances glioma virotherapy by inhibiting innate immune responses, PNAS, Aug. 22, 2006, pp. 12873-12878, 103(34).
Fulci, G. et al., Depletion of Peripheral Macrophages and Brain Microglia Increases Brain Tumor Titers of Oncolytic Viruses, Cancer Res, Oct. 1, 2007, pp. 9398-9406, 67(19).
Gage, F.H., Mammalian Neural Stem Cells, Science, Feb. 25, 2000, pp. 1433-1438, 287.
Galli, R. et al., Isolation and Characterization of Tumorigenic, Stem-like Neural Precursors from Human Glioblastoma, Cancer Research, Oct. 1, 2004, pp. 7011-0721, 64.
Ganesan, L.P. et al., The Protein-tyrosine Phosphatase SHP-1 Associates with the Phosphorylated Immunoreceptor Tyrosine-based Activation Motif of FcγRIIa to Modulate Signaling Events in Myeloid Cells, The Journal of Biological Chemistry, Sep. 12, 2003, pp. 35710-35717, 278(37).
Ganesan, L.P. et al., The Serine/Threonine Kinase AKT Promotes Fcγ Receptor-mediated Phagocytosis in Murine Macrophages through the Activation of p70S6 Kinase, The Journal of Biological Chemistry, Dec. 24, 2004, pp. 54416-54425, 279(52).
Ganesan, L.P. et al., FcγR-induced production of superoxide and inflammatory cytokines is differentially regulated by SHIP through its influence on PI3K and/or Ras/Erk pathways, Blood, Jul. 15, 2006, pp. 718-725, 108(2).
Ganesh, S. et al., Relaxin-Expressing, Fiber Chimeric Oncolytic Adenovirus Prolongs Survival of Tumor-Bearing Mice, Cancer Res, May 1, 2007, pp. 4399-4407, 67(9).
Ganesh, S. et al., Intratumoral Coadministration of Hyaluronidase Enzyme and Oncolytic Adenoviruses Enhances Virus Potency in Metastatic Tumor Models, Clin Cancer Res, Jun. 15, 2008, pp. 3933-3941, 14(12).
Gao, Z. et al., Voltammetric Determination of Dopamine in the Presence of Ascorbic Acid at Over-oxidized Polypyrrole-Indigo Carmine Film-coated Electrodes, Analyst, Mar. 1994, pp. 459-464, 119.
Gautier, I. et al., Early apoptosis-related changes triggered by HSV-1 in individual neuronlike cells, Experimental Cell Research, 2003, pp. 174-183, 289.
Gilbertson, R.J. et al., Making a tumour's bed: glioblastoma stem cells and the vascular niche, Nature Reviews, Oct. 2007, pp. 733-736, 7.
Gillespie, G.Y. et al., Glioma Migration Can Be Blocked by Nontoxic Inhibitors of Myosin II, Cancer Research, May 1, 1999, pp. 2076-2082, 59.
Gladson, C.L., The Extracellular Matrix of Gliomas: Modulation of Cell Function, Journal of Neuropathology and Experimental Neurology, Oct. 1999, pp. 1029-1040, 58(10).
Glass, R. et al., Glioblastoma-Induced Attraction of Endogenous Neural Precursor Cells is Associated with Improved Survival, The Journal of Neuroscience, Mar. 9, 2005, pp. 2637-2646, 25(10).
Godlewski, J. et al., Targeting of the Bmi-1 Oncogene/Stem Cell Renewal Factor by MicroRNA-128 Inhibits Glioma Proliferation and Self-Renewal, Cancer Res, Nov. 15, 2008, pp. 9125-9130, 68(22).
Goldstein, D.J. et al., Herpes Simplex Virus Type 1-Induced Ribonucleotide Reductase Activity is Dispensable for Virus Growth and DNA Synthesis: Isolation and Characterization of an ICP6 IacZ Insertion Mutant, Journal of Virology, Jan. 1988, pp. 196-205, 62(1).
Gomez-Manzano, C. et al., A novel E1A-E1B mutant adenovirus induces glioma regression in vivo, Oncogene, 2004, pp. 1821-1828, 23.
Gowda, A. et al., IL-21 mediates apoptosis through up-regulation of the BH3 family member BIM and enhances both direct and antibody-dependent cellular cytotoxicity in primary chronic lymphocytic leukemia cells in vitro, Blood, May 1, 2008, pp. 4723-4730, 111(9).
Greco, O. et al., Novel chimeric gene promoters responsive to hypoxia and ionizing radiation, Gene Therapy, 2002, pp. 1403-1411, 9.
Groth, A.G. et al., Phage Integrases: Biology and Applications, J. Mol. Biol., 2004, pp. 667-678, 335.
Guruvayoorappan, C., Tumor Versus Tumor-Associated Macrophages: How Hot is the Link?, Integrative Cancer Therapies, Jun. 2008, pp. 90-95, 7(2).
Hakkarainen, T. et al., Human Mesenchymal Stem Cells Lack Tumor Tropism but Enhance the Antitumor Activity of Oncolytic Adenoviruses in Orthotopic Lung and Breast Tumors, Human Gene Therapy, Jul. 2007, pp. 627-641, 18.
Hallak, L.K. et al., Targeted Measles Virus Vector Displaying Echistatin Infects Endothelial Cells via αvβ3 and Leads to Tumor Regression, Cancer Res, Jun. 15, 2005, pp. 5292-5300, 65(12).
Hamada, K. et al., Carrier Cell-mediated Delivery of a Replication-competent Adenovirus for Cancer Gene Therapy, Molecular Therapy, Jun. 2007, pp. 1121-1128, 15(6).
Hammarsten, O. et al., Inhibition of Topoisomerase II by ICRF-193 Prevents Efficient Replication of Herpes Simplex Virus Type 1, Journal of Virology, Jul. 1996, pp. 4523-4529, 70(7).
Hardcastle, J. et al., Oncolytic Viruses Driven by Tumor-Specific Promoters, Current Cancer Drug Targets, 2007, pp. 181-189, 7.
Hardcastle, J. et al., Enhanced Antitumor Efficacy of Vasculostatin (Vstat120) Expressing Oncolytic HSV-1, Molecular Therapy, Feb. 2010, pp. 285-294, 18(2).
Harrow, S. et al., HSV1716 injection into the brain adjacent to tumour following surgical resection of high-grade glioma: safety data and long-term survival, Gene Therapy, 2004, pp. 1648-1658, 11.
Harsh, G.R. et al., Thymidine kinase activation of ganciclovir in recurrent malignant gliomas: a gene-marking and neuropathological study, J. Neurosurg., May 2000, pp. 804-811, 92.
Haseley, A. et al., Advances in Oncolytic Virus Therapy for Glioma, Recent Pat CNS Drug Discov., Jan. 2009, pp. 1-13, 4(1).
Hatanaka, H. et al., Vascularization is decreased in pulmonary adenocarcinoma expressing brain-specific angiogenesis inhibitor 1 (BAI1), International Journal of Molecular Medicine, 2000, pp. 181-183, 5.
Hedley, S.J. et al., An adenovirus vector with a chimeric fiber incorporating stabilized single chain antibody achieves targeted gene delivery, Gene Therapy, 2006, pp. 88-94, 13.
He, T-C. et al., A simplified system for generating recombinant adenoviruses, Proc. Natl. Acad. Sci. USA, Mar. 1998, pp. 2509-2514, 95.
Heise, C. et al., ONYX-015, an E1B gene-attenuated adenovirus, causes tumor-specific cytolysis and antitumoral efficacy that can be augmented by standard chemotherapeutic agents, Nature Medicine, Jun. 1997, pp. 639-645, 3(6).

Heise, C. et al., An adenovirus E1A mutant that demonstrates potent and selective systemic anti-tumoral efficacy, Nature Medicine, Oct. 2000, pp. 1134-1139, 6(10).

Hellums, E.K. et al., Increased efficacy of an interleukin-12-secreting herpes simplex virus in a syngeneic intracranial murine glioma model, Neuro-Oncology, Jul. 2005, pp. 213-224.

Henning, L.N. et al., Pulmonary Surfactant Protein-A regulates Toll-like receptor expression and activity in human macrophages, J Immunol., Jun. 2008, pp. 7847-7858, 180(12).

Herrlinger, U. et al., Neural Precursor Cells for Delivery of Replication-Conditional HSV-1 Vectors to Intracerebral Gliomas, Molecular Therapy, Apr. 2000, pp. 347-357, 1(4).

Hoess, R.H. et al., The role of the loxP spacer region in P1 site-specific recombination, Nucleic Acids Research, 1986, pp. 2287-2300, 14(5).

Hoffmann, D. et al., Improved glioblastoma treatment with Ad5/35 fiber chimeric conditionally replicating adenoviruses, The Journal of Gene Medicine, 2007, pp. 764-778, 9.

Houghton, P.J. et al., Antitumor Activity of Temozolomide Combined with Irinotecan is Partly Independent of O6-Methylguanine-DNA Methyltransferase and Mismatch Repair Phenotypes in Xenograft Models, Clinical Cancer Research, Oct. 2000, pp. 4110-4118, 6.

Hu, B. et al., The Proteoglycan Brevican Binds to Fibronectin after Proteolytic Cleavage and Promotes Glioma Cell Motility, Journal of Biological Chemistry, Sep. 5, 2008, pp. 24848-24859, 283(36).

Iankov, I.D. et al., Infected Cell Carriers: A New Strategy for Systemic Delivery of Oncolytic Measles Viruses in Cancer Virotherapy, Molecular Therapy, Jan. 2007, pp. 114-122, 15(1).

Ichikawa, T. et al., Intraneoplastic Polymer-based Delivery of Cyclophosphamide for Intratumoral Bioconversion by a Replicating Oncolytic Viral Vector, Cancer Research, Feb. 1, 2001, pp. 864-868, 61.

Ichikawa, T. et al., Comparative Analyses of Transgene Delivery and Expression in Tumors Inoculated with a Replication-conditional or -defective Viral Vector, Cancer Research, Jul. 15, 2001, pp. 5336-5339, 61.

Ichikawa, T. et al., MRI of Transgene Expression: Correlation to Therapeutic Gene Expression, Neoplasia, 2002, pp. 523-530, 4(6).

Ikeda, K. et al., Oncolytic virus therapy of multiple tumors in the brain requires suppression of innate and elicited antiviral responses, Nature Medicine, Aug. 1999, pp. 881-887, 5(8).

Ikeda, K. et al., Complement Depletion Facilitates the Infection of Multiple Brain Tumors by an Intravascular, Replication-Conditional Herpes Simplex Virus Mutant, Journal of Virology, May 2000, pp. 4765-4775, 74(10).

Imhof, D. et al., Sequence Specificity of SHP-1 and SHP-2 Src Homology 2 Domains, The Journal of Biological Chemistry, Jul. 21, 2006, pp. 20271-20282, 281(29).

Inoue, R. et al., Infectious delivery of the 132 kb CDKN2A/CDKN2B genomic DNA region results in correctly spliced gene expression and growth suppression in glioma cells, Gene Therapy, 2004, pp. 1195-1204, 11.

Jackson, J.R. et al., The codependence of angiogenesis and chronic inflammation, The FASEB Journal, May 1997, pp. 457-465, 11.

Jacob, A. et al., FcγRIIb Modulation of Surface Immunoglobulin-induced Akt Activation in Murine B Cells, The Journal of Biological Chemistry, May 7, 1999, pp. 13704-13710, 274(19).

Jacobs, A. et al., HSV-1-Based Vectors for Gene Therapy of Neurological Diseases and Brain Tumors: Part I. HSV-1 Structure, Replication and Pathogenesis, Neoplasia, Nov. 1999, pp. 387-401, 1(5).

Jacobs, A. et al., Positron Emission Tomography-based Imaging of Transgene Expression Mediated by Replication-conditional, Oncolytic Herpes Simplex Virus Type 1 Mutant Vectors in Vivo, Cancer Research, Apr. 1, 2001, pp. 2983-2995, 61.

Jain, R.K., Normalization of Tumor Vasculature: An Emerging Concept in Antiangiogenic Therapy, Jan. 7, 2005, pp. 58-62, 307.

Jain, R.K., Angiogenesis in brain tumours, Nature Reviews, Aug. 2007, pp. 610-622, 8.

Jones, D.H. et al., Regulation of cancer cell migration and bone metastasis by RANKL, Nature, Mar. 30, 2006, pp. 692-696, 440.

Joshi, T. et al., Fcγ Receptor Signaling in Phagocytes, International Journal of Hematology, 2006, pp. 210-216, 84.

Joshi, T. et al., Molecular analysis of expression and function of hFcγRIIbl and b2 isoforms in myeloid cells, Molecular Immunology, 2006, pp. 839-850, 43.

Joshi, T. et al., The PtdIns 3-Kinase/Akt Pathway Regulates Macrophage-Mediated ADCC against B Cell Lymphoma, PLoS One, Jan. 2009, pp. 1-11, 4(1).

Josiah, D.T. et al., Adipose-derived Stem Cells as Therapeutic Delivery Vehicles of an Oncolytic Virus for Glioblastoma, Molecular Therapy, Feb. 2010, pp. 377-385, 18(2).

Kambara, H. et al., An Oncolytic HSV-1 Mutant Expressing ICP34.5 under Control of a Nestin Promoter Increases Survival of Animals even when Symptomatic from a Brain Tumor, Cancer Research, Apr. 1, 2005, pp. 2832-2839, 65.

Kambara, H. et al., Cyclophosphamide Allows for in vivo Dose Reduction of a Potent Oncolytic Virus, Cancer Res, Dec. 15, 2005, pp. 11255-11258, 65(24).

Kamen, L.A. et al., SHIP-1 Increases Early Oxidative Burst and Regulates Phagosome Maturation in Macrophages, The Journal of Immunology, 2008, pp. 7497-7505.

Karlin, S. et al., Methods for assessing the statistical significance of molecular sequence features by using general scoring schemes, Proc. Natl. Acad. Sci. USA, Mar. 1990, pp. 2264-2268, 87.

Karlin, S. et al., Applications and statistics for multiple high-scoring segments in molecular sequences, Proc. Natl. Acad. Sci. USA, Jun. 1993, pp. 5873-5877, 90.

Kasuya, H. et al., Selectivity of an Oncolytic Herpes Simplex Virus for Cells Expressing the DF3/MUC1 Antigen, Cancer Research, Apr. 1, 2004, pp. 2561-2567, 64.

Kato, H. et al., Differential roles of MDA5 and RIG-I helicases in the recognition of RNA viruses, Nature, May 4, 2006, pp. 101-105, 441.

Kaur, B. et al., Expression, Purification, and Characterization of Ultraviolet DNA Endonuclease from *Schizosaccharomyces pombe*, Biochemistry, 1998, pp. 11599-11604, 37.

Kaur, B. et al., A Uve1p-Mediated Mismatch Repair Pathway in *Schizosaccharomyces pombe*, Molecular and Cellular Biology, Jul. 1999, pp. 4703-4710, 19(7).

Kaur, B. et al, Ultraviolet Damage Endonuclease (Uve1p): A Structure and Strand-Specific DNA Endonuclease, Biochemistry, 2000, pp. 5788-5796, 39.

Kaur, B. et al., Brain Angiogenesis Inhibitor 1 is Differentially Expressed in Normal Brain and Glioblastoma Independently of p53 Expression, American Journal of Pathology, Jan. 2003, pp. 19-27, 162(1).

Kaur, B. et al., Genetic and hypoxic regulation of angiogenesis in gliomas, Journal of Neuro-Oncology, 2004, pp. 229-243, 70.

Kaur, B. et al., Vasculostatin, a proteolytic fragment of Brain Angiogenesis Inhibitor 1, is an antiangiogenic and antitumorigenic factor, Oncogene, 2005, pp. 3632-3642, 24.

Kaur, B. et al., Hypoxia and the hypoxia-inducible-factor pathway in glioma growth and angiogenesis, Neuro-Oncology, Apr. 2005, pp. 134-153.

Kaur, B. et al., Oncolytic viruses: extreme treatment for an extreme disease, Future Microbiol., 2006, pp. 351-353, 1(4).

Kaur, B. et al., Personalizing oncolytic virotherapy?, Molecular Therapy, Jan. 2007, pp. 6-7, 15(1).

Kaur, B. et al., Vasculostatin Inhibits Intracranial Glioma Growth and Negatively Regulates in vivo Angiogenesis through a CD36-Dependent Mechanism, Cancer Res, Feb. 1, 2009, pp. 1212-1220, 69(3).

Kawaguchi, A. et al., Nestin-EGFP Transgenic Mice: Visualization of the Self-Renewal and Multipotency of CNS Stem Cells, Molecular and Cellular Neuroscience, 2001, pp. 259-273, 17.

Kefas, B. et al., microRNA-7 Inhibits the Epidermal Growth Factor Receptor and the Akt Pathway and is Down-regulated in Glioblastoma, Cancer Res, May 15, 2008, pp. 3566-3572, 68(10).

Kikuchi, E. et al., Inhibition of Orthotopic Human Bladder Tumor Growth by Lentiviral Gene Transfer of Endostatin, Clinical Cancer Research, Mar. 1, 2004, pp. 1835-1842, 10.

Kilby, N.J. et al., Site-specific recombinases: tools for genome engineering, TIG, Dec. 1993, pp. 413-421, 9(12).

Kim, J-H. et al., Relaxin Expression From Tumor-Targeting Adenoviruses and Its Intratumoral Spread, Apoptosis Induction, and Efficacy, Journal of the National Cancer Institute, Oct. 18, 2006, pp. 1482-1493, 98(20).

Kirn, D. et al., Clinical research results with dl1520 (Onyx-015), a replication-selective adenovirus for the treatment of cancer: what have we learned?, Gene Therapy, 2001, pp. 89-98, 8.

Knaän-Shanzer, S. et al., Endowing Human Adenovirus Serotype 5 Vectors with Fiber Domains of Species B Greatly Enhances Gene Transfer into Human Mesenchymal Stem Cells, Stem Cells, 2005, pp. 1598-1607, 23.

Ko, D. et al., Development of transcriptionally regulated oncolytic adenoviruses, Oncogene, 2005, pp. 7763-7774, 24.

Koh, J.T. et al., Extracellular fragment of brain-specific angiogenesis inhibitor 1 suppresses endothelial cell proliferation by blocking αvβ5 integrin, Experimental Cell Research, 2004, pp. 172-184, 294.

Komarova, S. et al., Mesenchymal progenitor cells as cellular vehicles for delivery of oncolytic adenoviruses, Mol Cancer Ther, 2006, Mar. 2006, 5(3).

Komohara, Y. et al., Possible involvement of the M2 anti-inflammatory macrophage phenotype in growth of human gliomas, J Pathol, 2008, pp. 15-24, 216.

Kondadasula, S.V. et al., Colocalization of the IL-12 receptor and FcyRIIIa to natural killer cell lipid rafts leads to activation of ERK and enhanced production of interferon-y, Blood, Apr. 15, 2008, pp. 4173-4183, 111(8).

Kramm, C.M. et al., Therapeutic Efficiency and Safety of a Second-Generation Replication-Conditional HSV1 Vector for Brain Tumor Gene Therapy, Human Gene Therapy, Nov. 20, 1997, pp. 2057-2068, 8.

Krasnykh, V. et al., Characterization of an Adenovirus Vector Containing a Heterologous Peptide Epitope in the HI Loop of the Fiber Knob, Journal of Virology, Mar. 1998, pp. 1844-1852, 72(3).

Kunstfeld, R. et al., Induction of cutaneous delayed-type hypersensitivity reactions in VEGF—A transgenic mice results in chronic skin inflammation associated with persistent lymphatic hyperplasia, Blood, Aug. 15, 2004, pp. 1048-1057, 104(4).

Kuriyama, N. et al., Pretreatment with Protease is a Useful Experimental Strategy for Enhancing Adenovirus-Mediated Cancer Gene Therapy, Human Gene Therapy, Nov. 1, 2000, pp. 2219-2230, 11.

Kurozumi, K. et al., Effect of Tumor Microenvironment Modulation on the Efficacy of Oncolytic Virus Therapy, JNCI, Dec. 5, 2007, pp. 1768-1781, 99(23).

Kurozumi, K. et al., Oncolytic HSV-1 Infection of Tumors Induces Angiogenesis and Upregulates CYR61, Mol Ther., Aug. 2008, pp. 1382-1391, 16(8).

Kurre, P. et al., Efficient Marking of Murine Long-Term Repopulating Stem Cells Targeting Unseparated Marrow Cells at Low Lentiviral Vector Particle Concentration, Molecular Therapy, Jun. 2004, pp. 914-922, 9(6).

Lamfers, M.L.M. et al., Cyclophosphamide Increases Transgene Expression Mediated by an Oncolytic Adenovirus in Glioma-Bearing Mice Monitored by Bioluminescence Imaging, Molecular Therapy, Dec. 2006, pp. 779-788, 14(6).

Lamfers, M. et al., Homing properties of adipose-derived stem cells to intracerebral glioma and the effects of adenovirus infection, Cancer Letters, 2009, pp. 78-87, 274.

Lange-Asschenfeldt, B. et al., Increased and prolonged inflammation and angiogenesis in delayed-type hypersensitivity reactions elicited in the skin of thrombospondin-2-deficient mice, Blood, Jan. 15, 2002, pp. 538-545, 99(2).

Lapalombella, R. et al., The humanized CD40 antibody SGN-40 demonstrates pre-clinical activity that is enhanced by lenalidomide in chronic lymphocytic leukaemia, British Journal of Haematology, 2009, pp. 848-855, 144.

Lawler, S.E. et al., Genetic strategies for brain tumor therapy, Cancer Gene Therapy, 2006, pp. 225-233, 13.

Lazennec, G. et al, Concise review: adult multipotent stromal cells and cancer: risk or benefit?, Stem Cells, Jun. 2008, pp. 1387-1394, 26(6).

Le, L.P. et al., Dynamic Monitoring of Oncolytic Adenovirus in Vivo by Genetic Capsid Labeling, Journal of the National Cancer Institute, Feb. 1, 2006, pp. 203-214, 98(3).

Lee, D-H. et al., Targeting Rat Brainstem Glioma Using Human Neural Stem Cells and Human Mesenchymal Stem Cells, Clin Cancer Res, Aug. 1, 2009, pp. 4925-4934, 15(15).

Lee, G. et al., Role of nucleotide sequences of loxP spacer region in Cre-mediated recombination, Gene, 1998, pp. 55-65, 216.

Lee, J.H. et al., Comparative study of angiostatic and anti-invasive gene expressions as prognostic factors in gastric cancer, International Journal of Oncology, 2001, pp. 355-361, 18.

Leopardi, R. et al., The herpes simplex virus major regulatory protein ICP4 blocks apoptosis induced by the virus or by hyperthermia, Proc. Natl. Acad. Sci. USA, Sep. 1996, pp. 9583-9587, 93.

Li, S., Electroporation Gene Therapy: New Developments in Vivo and in Vitro, Current Gene Therapy, 2004, pp. 309-315, 4.

Liu, T-C. et al., Functional interactions of antiapoptotic proteins and tumor necrosis factor in the context of a replication-competent adenovirus, Gene Therapy, 2005, pp. 1333-1346, 12.

Liu, T-C. et al., Viruses with deletions in antiapoptotic genes as potential oncolytic agents, Oncogene, 2005, pp. 6069-6079, 24.

Liu, T-C. et al., Dominant-Negative Fibroblast Growth Factor Receptor Expression Enhances Antitumoral Potency of Oncolytic Herpes Simplex Virus in Neural Tumors, Clin Cancer Res, Nov. 15, 2006, pp. 6791-6799, 12(22).

Liu, T-C. et al., Oncolytic HSV Armed with Platelet Factor 4, an Antiangiogenic Agent, Shows Enhanced Efficacy, Molecular Therapy, Dec. 2006, pp. 789-797, 14(6).

Lorbach, E. et al., Site-specific Recombination in Human Cells Catalyzed by Phage λ Integrase Mutants, J. Mol. Biol., 2000, pp. 1175-1181, 296.

Luker, G.D. et al., Noninvasive Bioluminescence Imaging of Herpes Simplex Virus Type 1 Infection and Therapy in Living Mice, Journal of Virology, Dec. 2002, pp. 12149-12161, 76(23).

Lund, J.M. et al., Recognition of single-stranded RNA viruses by Toll-like receptor 7, PNAS, Apr. 13, 2004, pp. 5598-5603, 101(15).

Lyden, T.W. et al., The Fc Receptor for IgG Expressed in the Villus Endothelium of Human Placenta is FcyRIIb2, The Journal of Immunology, 2001, pp. 3882-3889.

Mader, E.K. et al., Mesenchymal Stem Cell Carriers Protect Oncolytic Measles Viruses from Antibody Neutralization in an Orthotopic Ovarian Cancer Therapy Model, Clin Cancer Res, Dec. 1, 2009, pp. 7246-7255, 15(23).

Mahendra, G. et al., Antiangiogenic cancer gene therapy by adeno-associated virus 2-mediated stable expression of the soluble FMS-like tyrosine kinase-1 receptor, Cancer Gene Therapy, 2005, pp. 26-34, 12.

Mahller, Y.Y. et al., Neuroblastoma Cell Lines Contain Pluripotent Tumor Initiating Cells That Are Susceptible to a Targeted Oncolytic Virus, PLoS One, Jan. 2009, pp. 1-10, 4(1).

Mabjeesh, N.J. et al., Geldanamycin Induces Degradation of Hypoxia-inducible Factor 1α Protein via the Proteosome Pathway in Prostate Cancer Cells, Cancer Research, May 1, 2002, pp. 2478-2481, 62.

Makhov, A.M. et al., Origin-specific unwinding of herpes simplex virus 1 DNA by the viral UL9 and ICP8 proteins: Visualization of a specific preunwinding complex, PNAS, Feb. 4, 2003, pp. 898-903, 100(3).

Mandell, J.G. et al., Zinc Finger Tools: custom DNA-binding domains for transcription factors and nucleases, Nucleic Acids Research, 2006, pp. W516-E523, 34.

Markert, J.M. et al., Conditionally replicating herpes simplex virus mutant, G207 for the treatment of malignant glioma: results of a phase I trial, Gene Therapy, 2000, pp. 867-874, 7.

Markert, J.M. et al., Phase Ib Trial of Mutant Herpes Simplex Virus G207 Inoculated Pre- and Post-tumor Resection for Recurrent GBM, Molecular Therapy, Jan. 2009, pp. 199-207, 17(1).

Martino, G. et al., The therapeutic potential of neural stem cells, Nature Reviews, May 2006, pp. 395-406, 7.

Martuza, R.L. et al., Experimental Therapy of Human Glioma by Means of a Genetically Engineered Virus Mutant, Science, May 10, 1991, pp. 854-856, 252.

Mathis, J.M. et al., Oncolytic adenoviruses—selective retargeting to tumor cells, Oncogene, 2005, pp. 7775-7791, 24.

McKee, T.D. et al., Degradation of Fibrillar Collagen in a Human Melanoma Xenograft Improves the Efficacy of an Oncolytic Herpes Simplex Virus Vector, Cancer Res, Mar. 1, 2006, pp. 2509-2513, 66(5).

McLendon, R.E. et al., Is the Long-Term Survival of Patients with Intracranial Glioblastoma Multiforme Overstated?, Cancer, Oct. 15, 2003, pp. 1745-1748, 98(8).

Meck, M.M. et al., A Virus-directed Enzyme Prodrug Therapy Approach to Purging Neuroblastoma Cells from Hematopoietic Cells Using Adenovirus Encoding Rabbit Carboxylesterase and CPT-11, Cancer Research, Jul. 1, 2001, pp. 5083-5089, 61.

Menéndez, J.A. et al., The angiogenic factor CYR61 in breast cancer: molecular pathology and therapeutic perspectives, Endocrine-Related Cancer, 2003, pp. 141-152, 2003.

Menotti, L. et al., Construction of a Fully Retargeted Herpes Simplex Virus 1 Recombinant Capable of Entering Cells Solely via Human Epidermal Growth Factor Receptor 2, Journal of Virology, Oct. 2008, pp. 10153-10161, 82(20).

Miller, J.C. et al., An improved zinc-finger nuclease architecture for highly specific genome editing, Nature Biotechnology, Jul. 2007, pp. 778-785, 25(7).

Mineta, T. et al., Attenuated multi-mutated herpes simplex virus-1 for the treatment of malignant gliomas, Nature Medicine, Sep. 1995, pp. 938-943, 1(9).

Mizuguchi, H. et al., Fiber-modified adenovirus vectors mediate efficient gene transfer into undifferentiated and adipogenic-differentiated human mesenchymal stem cells, Biochemical and Biophysical Research Communications, 2005, pp. 1101-1106, 332.

Mo, F-E. et al., CYR61 (CCN1) is Essential for Placental Development and Vascular Integrity, Molecular and Cellular Biology, Dec. 2002, pp. 8709-8720, 22(24).

Mohr, I., To replicate or not to replicate: achieving selective oncolytic virus replication in cancer cells through translational control, Oncogene, 2005, pp. 7697-7709, 24.

Mok, W. et al., Matrix Metalloproteinases-1 and -8 Improve the Distribution and Efficacy of an Oncolytic Virus, Cancer Res, Nov. 15, 2007, pp. 10664-10668, 67(22).

Mone, A.P. et al., Alemtuzumab induces caspase-independent cell death in human chronic lymphocytic leukemia cells through a lipid raft-dependent mechanism, Leukemia, 2006, pp. 272-279, 20.

Moon, L.D.F. et al., Regeneration of CNS axons back to their target following treatment of adult rat brain with chondroitinase ABC, Nature Neuroscience, May 2001, pp. 465-466, 4(5).

Moon, L.D.F. et al., Limited Growth of Severed CNS Axons After Treatment of Adult Rat Brain With Hyaluronidase, Journal of Neuroscience Research, 2003, pp. 23-37, 71.

Muir, E.M. et al., Modification of N-glycosylation sites allows secretion of bacterial chondroitinase ABC from mammalian cells, Journal of Biotechnology, 2009, 8 pages.

Mullen, J.T. et al., Regulation of Herpes Simplex Virus 1 Replication Using Tumor-Associated Promoters, Annals of Surgery, 2002, pp. 502-513, 236(4).

Mullen, J.T. et al., Oncolysis by Viral Replication and Inhibition of Angiogenesis by a Replication-Conditional Herpes Simplex Virus that Expresses Mouse Endostatin, Cancer, Aug. 15, 2004, pp. 869-877, 101(4).

Müller, A. et al., Involvement of chemokine receptors in breast cancer metastasis, Nature, Mar. 1, 2001, pp. 50-56, 401.

Nagy, A. et al., Cre Recombinase: The Universal Reagent for Genome Tailoring, Genesis, 2000, pp. 99-109, 26.

Nakamuro, H. et al., Regulation of herpes simplex virus γ134.5 expression and oncolysis of diffuse liver metastases by Myb34.5, The Journal of Clinical Investigation, Apr. 2002, pp. 871-882, 109(7).

Nakano, K. et al., Herpes Simplex Virus Targeting to the EGF Receptor by a gD-Specific Soluble Bridging Molecule, Molecular Therapy, Apr. 2005, pp. 617-626, 11(4).

Nakashima, H. et al., Inducible oncolytic transformation of replication-deficient virus for the cell-based virotherapy, American Society of Gene Therapy 12th Annual Meeting, 2009, 2 pages.

Nakashima, H. et al., Directing systemic oncolytic viral delivery to tumors via carrier cells, Cytokine & Growth Factor Reviews, 2010, 8 pages.

Nam, D-H. et al., Expression of VEGF and brain specific angiogenesis inhibitor-1 in glioblastoma: prognostic significance, Oncology Reports, 2004, pp. 863-869, 11.

Nemunaitis, J. et al., Intravenous infusion of a replication-selective adenovirus (ONYX-015) in cancer patients: safety, feasibility and biological activity, Gene Therapy, 2001, pp. 746-759, 8.

Nguyen, M.L. et al., Susceptibility of cancer cells to herpes simplex virus-dependent apoptosis, Journal of General Virology, 2007, pp. 1866-1875, 88.

Nichols, M. et al., FLP Recombinase/Estrogen Receptor Fusion Proteins Require the Receptor D Domain for Responsiveness to Antagonists, but not Agonists, Molecular Endocrinology, 1997, pp. 950-961, 11.

Nicholson, C. et al., Extracellular space structure revealed by diffusion analysis, TINS, 1998, pp. 207-215, 21(5).

Nilsson, M. et al., Development of an adenoviral vector system with adenovirus serotype 35 tropism; efficient transient gene transfer into primary malignant hematopoietic cells, J Gene Med, 2004, pp. 631-641, 6.

Nishimori, H. et al., A novel brain-specific p53-target gene, BAI1, containing thrombospondin type 1 repeats inhibits experimental angiogenesis, Oncogene, 1997, pp. 2145-2150, 15.

Nimonkar, A.V. et al., Reconstitution of recombination-dependent DNA synthesis in herpes simplex virus 1, PNAS, Sep. 2, 2003, pp. 10201-10206, 100(18).

Nowicki, M.O. et al., Lithium inhibits invasion of glioma cells; possible involvement of glycogen synthase kinase-3, Neuro-Oncology, Oct. 2008, pp. 690-699.

Nusinzon, I. et al., Interferon-stimulated transcription and innate antiviral immunity require deacetylase activity and histone deacetylase 1, PNAS, Dec. 9, 2003, pp. 14742-14747, 100(25).

Nyberg, P. et al., Endogenous Inhibitors of Angiogenesis, Cancer Res, May 15, 2005, pp. 3967-3979, 65(10).

Ohira, K. et al., Ischemia-induced neurogenesis of neocortical layer 1 progenitor cells, Nature Neuroscience, Feb. 2010, pp. 173-179, 13(2).

Olivares, E.C. et al., Phage R4 integrase mediates site-specific integration in human cells, Gene, 2001, pp. 167-176, 278.

Oreffo, R.O.C. et al., Mesenchymal Stem Cells, Lineage, Plasticity, and Skeletal Therapeutic Potential, Stem Cell Reviews, 2005, pp. 169-178, 1.

Otsuki, A. et al., Histone Deacetylase Inhibitors Augment Antitumor Efficacy of Herpes-based Oncolytic Viruses, Molecular Therapy, Sep. 2008, pp. 1546-1555, 16(9).

Oura, H. et al., A critical role of placental growth factor in the induction of inflammation and edema formation, Blood, Jan. 15, 2003, pp. 560-567, 101(2).

Packer, R.J. et al., A prospective study of cognitive function in children receiving whole-brain radiotherapy and chemotherapy: 2-year results, J Neurosurg, 1989, pp. 707-713, 70.

Packer, R.J. et al., Improved survival with the use of adjuvant chemotherapy in the treatment of medulloblastoma, J Neurosurg, 1991, pp. 433-440, 74.

Papanastassiou, V. et al., The potential for efficacy of the modified (ICP 34.5-) herpes simplex virus HSV1716 following intratumoural injection into human malignant glioma: a proof of principle study, Gene Therapy, 2002, pp. 398-406, 9.

Parihar, R. et al., Src Homology 2-Containing Inositol 5'-Phosphatase 1 Negatively Regulates IFN-γ Production by Natural Killer Cells Stimulated with Antibody-Coated Tumor Cells and Interleukin-12, Cancer Res, Oct. 1, 2005, pp. 9099-9107, 65(19).

Park, D. et al., BAI1 is an engulfment receptor for apoptotic cells upstream of the ELMO/Dock180/Rac module, Nature, Nov. 15, 2007, pp. 430-435, 450.

Park, J.W. et al., Epidermal growth factor (EGF) receptor targeted delivery of PEGylated adenovirus, Biochemical and Biophysical Research Communications, 2008, pp. 769-774, 366.

Park, Y.W. et al., Thrombospondin 2 Functions as an Endogenous Regulator of Angiogenesis and Inflammation in Rheumatoid Arthritis, American Journal of Pathology, Dec. 2004, pp. 2087-2098, 165(6).

Parsa, K.V.L. et al., Macrophage Pro-Inflammatory Response to *Francisella novicida* Infection is Regulated by SHIP, PLoS Pathogens, Jul. 2006, pp. 0681-0690, 2(7).

Parsa, K.V.L. et al., The tyrosine kinase Syk promotes phagocytosis of *Francisella* through the activation of Erk, Mol Immunol, May 2008, pp. 3012-3021, 45(10).

Parsa, K.V.L. et al., *Francisella* gains a survival advantage within mononuclear phagocytes by suppressing the host IFNγ response, Mol Immunol., Jul. 2008, pp. 3428-3437, 45(12).

Patel, V.J. et al., Schedule-dependent Activity of Temozolomide plus CPT-11 against a Human Central Nervous System Tumor-derived Xenograft, Clinical Cancer Research, Oct. 2000, pp. 4154-4157, 6.

Pawlik, T.M. et al., Oncolysis of Diffuse Hepatocellular Carcinoma by Intravascular Administration of a Replication-competent, Genetically Engineered Herpesvirus, Cancer Research, Jun. 1, 2000, pp. 2790-2795, 60.

Pawlik, T.M. et al., Prodrug Bioactivation and Oncolysis of Diffuse Liver Metastases by a Herpes Simplex Virus 1 Mutant that Expresses the CYP2B1 Transgene, Cancer, Sep. 1, 2002, pp. 1171-1181, 95(5).

Pecora, A.L. et al., Phase I Trial of Intravenous Administration of PV701, an Oncolytic Virus, in Patients With Advanced Solid Cancers, Journal of Clinical Oncology, May 1, 2002, pp. 2251-2266, 20(9).

Pendurthi, U.R. et al., Proteolysis of CCN1 by Plasmin: Functional Implications, Cancer Res, Nov. 1, 2005, pp. 9705-9711, 65(21).

Pengal, R.A. et al., SHIP-2 Inositol Phosphatase is Inducibly Expressed in Human Monocytes and Serves to Regulate Fcγ Receptor-mediated Signaling, The Journal of Biological Chemistry, Jun. 20, 2003, pp. 22657-22663, 278(25).

Pengal, R.A. et al., Lipopolysaccharide-induced production of interleukin-10 is promoted by the serine/threonine kinase Akt, Molecular Immunology, 2006, pp. 1557-1564, 43.

Peng, K-W. et al., Non-invasive in vivo monitoring of trackable viruses expressing soluble marker peptides, Nature Medicine, May 2002, pp. 527-531, 8(5).

Phuangsab, A. et al., Newcastle disease virus therapy of human tumor xenografts: antitumor effects of local or systemic administration, Cancer Letters, 2001, pp. 27-36, 172.

Pike, S.E. et al., Vasostatin, a Calreticulin Fragment, Inhibits Angiogenesis and Suppresses Tumor Growth, The Journal of Experimental Medicine, Dec. 21, 1998, pp. 2349-2356, 188(12).

Pluchino, S. et al., Neurosphere-derived multipotent precursors promote neuroprotection by an immunomodulatory mechanism, Nature, Jul. 14, 2005, pp. 266-271, 436.

Post, D.E. et al., Cancer Therapy with a Replicating Oncolytic Adenovirus Targeting the Hypoxic Microenvironment of Tumors, Clinical Cancer Research, Dec. 15, 2004, pp. 8603-8612, 10.

Potter, P.M. et al., Isolation and Partial Characterization of a cDNA Encoding a Rabbit Liver Carboxylesterase That Activates the Prodrug Irinotecan (CPT-11), Cancer Research, Jun. 15, 1998, pp. 2646-2651, 58.

Potter, P.M. et al., Cellular Localization Domains of a Rabbit and a Human Carboxylesterase: Influence on Irinotecan (CPT-11) Metabolism by the Rabbit Enzyme, Cancer Research, Aug. 15, 1998, pp. 3627-3632, 58.

Purifoy, D.J.M. et al., Herpes Simplex Virus DNA Polymerase as the Site of Phosphonoacetate Sensitivity: Temperature-Sensitive Mutants, Journal of Virology, Nov. 1977, pp. 470-477, 24(2).

Qiao, J. et al., Purging metastases in lymphoid organs using a combination of antigen-nonspecific adoptive T cell therapy, oncolytic virotherapy and immunotherapy, Nature Medicine, Jan. 2008, pp. 37-44, 14(1).

Rainov, N.G. et al., Selective Uptake of Viral and Monocrystalline Particles Delivered Intra-Arterially to Experimental Brain Neoplasms, Human Gene Therapy, Dec. 1995, pp. 1543-1552, 6.

Rajaram, M.V.S. et al., Akt/Protein Kinase B Modulates Macrophage Inflammatory Response to *Francisella* Infection and Confers a Survival Advantage in Mice, The Journal of Immunology, 2006, pp. 6317-6324.

Rajčáni, J. et al., Peculiarities of Herpes Simplex Virus (HSV) Transcription: An overview, Virus Genes, 2004, pp. 293-310, 28(3).

Rampling, R. et al., Toxicity evaluation of replication-competent herpes simplex virus (ICP 34.5 null mutant 1716) in patients with recurrent malignant glioma, Gene Therapy, 2000, pp. 859-866, 7.

Ranki, T. et al., A heparan sulfate-targeted conditionally replicative adenovirus, Ad5.pk7-Δ24, for the treatment of advanced breast cancer, Gene Therapy, 2007, pp. 58-67, 14.

Ravichandran, K.S. et al., Engulfment of apoptotic cells: signals for a good meal, Nature Reviews, Dec. 2007, pp. 964-974, 7.

Raykov, Z. et al., Carrier Cell-Mediated Delivery of Oncolytic Parvoviruses for Targeting Metastases, Int. J. Cancer, 2004, pp. 742-749, 109.

Raykov, Z. et al., Potential of tumour cells for delivering oncolytic viruses, Gene Therapy, 2008, pp. 704-710, 15.

Reddy, P.S. et al., Development of adenovirus serotype 35 as a gene transfer vector, Virology, 2003, pp. 384-393, 311.

Reid, T. et al., Hepatic Arterial Infusion of a Replication-selective Oncolytic Adenovirus (dl1520): Phase II Viral, Immunologic, and Clinical Endpoints, Cancer Research, Nov. 1, 2002, pp. 6070-6079, 62.

Rein, D.T. et al., Gene Transfer to Cervical Cancer With Fiber-Modified Adenoviruses, Int. J. Cancer, 2004, pp. 698-704, 111.

Rhodes, K.E. et al., Chondroitin sulphate proteoglycans: preventing plasticity or protecting the CNS?, J. Anat., 2004, pp. 33-48, 204.

Ribatti, D. et al., The gelatin sponge—chorioallantoic membrane assay, Nature Protocols, 2006, pp. 85-91, 1(1).

Roda, J.M. et al., Interleukin-21 Enhances NK Cell Activation in Response to Antibody-Coated Targets, The Journal of Immunology, 2006, pp. 120-129.

Roda, J.M. et al., Natural Killer Cells Produce T Cell-Recruiting Chemokines in Response to Antibody-Coated Tumor Cells, Cancer Res, Jan. 1, 2006, pp. 517-526, 66(1).

Roda, J.M. et al., The Activation of Natural Killer Cell Effector Functions by Cetuximab-Coated, Epidermal Growth Factor Receptor-Positive Tumor Cells is Enhanced by Cytokines, Clin Cancer Res, Nov. 1, 2007, pp. 6419-6428, 13(21).

Roizman, B., The function of herpes simplex virus genes: A primer for genetic engineering of novel vectors, Proc. Natl. Acad. Sci. USA, Oct. 1996, pp. 11307-11312, 93.

Roizman, B. et al., The Nine Ages of Herpes Simplex Virus, Herpes, 2001, pp. 23-27, 8(1).

Rolls, A. et al., A sulfated disaccharide derived from chondroitin sulfate proteoglycan protects against inflammation-associated neurodegeneration, The FASEB Journal, Jan. 5, 2006, pp. 547-549, 20.

Rosenberg, G.A. et al., TIMP-2 reduces proteolytic opening of blood-brain barrier by type IV collagenase, Brain Research, 1992, pp. 203-207, 576.

Russell, S.J. et al., RNA viruses as virotherapy agents, Cancer Gene Therapy, 2002, pp. 961-966, 9.

Saeki, Y. et al., Herpes Simplex Virus Type 1 DNA Amplified as Bacterial Artificial Chromosome in *Escherichia coli*: Rescue of Replication-Competent Virus Progeny and Packaging of Amplicon Vectors, Human Gene Therapy, Dec. 10, 1998, pp. 2787-2794, 9.

Saeki, Y. et al., Improved Helper Virus-Free Packaging System for HSV Amplicon Vectors Using an ICP27-Deleted, Oversized HSV-1 DNA in a Bacterial Artificial Chromosome, Molecular Therapy, Apr. 2001, pp. 591-601, 3(4).

Saeki, Y. et al., Improved HSV-1 Amplicon Packaging System Using ICP27-Deleted, Oversized HSV-1 BAC DNA, Methods in Molecular Medicine, 2003, pp. 51-59, 76.

Sardjono, C.T. et al., Palmitoylation at Cys595 is essential for PECAM-1 localisation into membrane microdomains and for efficient PECAM-1-mediated cytoprotection, Thromb Haemost, 2006, pp. 756-766, 96.

Satoh, T. et al., PILRα is a herpes simplex virus-1 entry co-receptor that associates with glycoprotein B, Cell, 2008, pp. 935-944, 132(6).

Sauer, B. et al., Site-specific DNA recombination in mammalian cells by the Cre recombinase of bacteriophage P1, Proc. Natl. Acad. Sci. USA, Jul. 1988, pp. 5166-5170, 85.

Sauer, B., Manipulation of Transgenes by Site-Specific Recombination: Use of Cre Recombinase, Method in Enzymology, 1993, pp. 890-900, 225.

Schang, L.M. et al., Transcription of Herpes Simplex Virus Immediate-Early and Early Genes is Inhibited by Roscovitine, an Inhibitor Specific for Cellular Cyclin-Dependent Kinases, Journal of Virology, Mar. 1999, pp. 2161-2172, 73(3).

Schang, L.M. et al., Roscovitine, a Specific Inhibitor of Cellular Cyclin-Dependent Kinases, Inhibits Herpes Simplex Virus DNA Synthesis in the Presence of Viral Early Proteins, Journal of Virology, Mar. 2000, pp. 2107-2120, 74(5).

Schellingerhout, D. et al., Quantitation of HSV mass distribution in a rodent brain tumor model, Gene Therapy, 2000, pp. 1648-1655, 7.

Schiffer, C.A. et al., Opportunities for the Use of Thrombopoietic Growth Factors, Stem Cells, 1998, pp. 249-253, 16 (suppl 2).

Seth, P., Vector-Mediated Cancer Gene Therapy, Cancer Biology & Therapy, May 2005, pp. 512-517, 4(5).

Shah, K. et al., Real-time imaging of TRAIL-induced apoptosis of glioma tumors in vivo, Oncogene, 2003, pp. 6865-6872, 22.

Shen, Q. et al., Endothelial Cells Stimulate Self-Renewal and Expand Neurogenesis of Neural Stem Cells, Science, May 28, 2004, pp. 1338-1340, 304.

Simpson, S.A. et al., Nectin-1/HveC mediates herpes simplex virus type 1 entry into primary human sensory neurons and fibroblasts, Journal of NeuroVirology, 2005, pp. 208-218, 11.

Singh, S.K. et al., Identification of human brain tumour initiating cells, Nature, Nov. 18, 2004, pp. 396-401, 432.

Sonabend, A.M. et al., Mesenchymal Stem Cells Effectively Deliver an Oncolytic Adenovirus to Intracranial Glioma, Stem Cells, 2008, pp. 831-841, 26.

Spaeth, E. et al., Inflammation and tumor microenvironments: defining the migratory itinerary of mesenchymal stem cells, Gene Therapy, 2008, pp. 730-738, 15.

Stark, W.M. et al., Catalysis by site-specific recombinases, TIG, 1992, pp. 432-439, 8(12).

Sternberg, N. et al., Bacteriophage P1 Site-specific Recombination, I. Recombination Betweem loxP Sites, J. Mol. Biol., 1981, pp. 467-486, 150.

Sterman, D.H. et al., Adenovirus-Mediated Herpes Simplex Virus Thymidine Kinase/Ganciclovir Gene Therapy in Patients with Localized Malignancy: Results of a Phase I Clinical Trial in Malignant Mesothelioma, Human Gene Therapy, May 1, 1998, pp. 1083-1092, 9.

Stoff-Khalili, M.A. et al., Mesenchymal stem cells as a vehicle for targeted delivery of CRAds to lung metastases of breast carcinoma, Breast Cancer Res Treat, 2007, pp. 157-167, 105.

Stojdl, D.F. et al., Exploiting tumor-specific defects in the interferon pathway with a previously unknown oncolytic virus, Nature Medicine, Jul. 2000, pp. 821-825, 6(7).

Strojnik, T. et al., Neural stem cell markers, nestin and musashi proteins, in the progression of human glioma: correlation of nestin with prognosis of patient survival, Surgical Neurology, 2007, pp. 133-144, 68.

Struve, J. et al., Disruption of the Hyaluronan-Based Extracellular Matrix in Spinal Cord Promotes Astrocyte Proliferation, GLIA, 2005, pp. 16-24, 52.

Studeny, M. et al., Bone Marrow-derived Mesenchymal Stem Cells as Vehicles for Interferon-β Delivery into Tumors, Cancer Research, Jul. 1, 2002, pp. 3603-3608, 62.

Studeny, M. et al., Mesenchymal Stem Cells: Potential Precursors for Tumor Stroma and Targeted-Delivery Vehicles for Anticancer Agents, Journal of the National Cancer Institute, Nov. 3, 2004, pp. 1593-1603, 96(21).

Stupp, R. et al., Radiotherapy plus Concomitant and Adjuvant Temozolomide for Glioblastoma, N Engl J Med, Mar. 10, 2005, pp. 987-996, 352(10).

Sugimura, T. et al., Experimental Chemonucleolysis With Chondroitinase ABC in Monkeys, Spine, Jan. 15, 1996, pp. 161-165, 21(2).

Sun, X. et al., Disulfides Modulate RGD-inhibitable Cell Adhesive Activity of Thrombospondin, The Journal of Cell Biology, 1992, pp. 693-701, 118.

Sundaresan, P. et al., Attenuated, Replication-Competent Herpes Simplex Virus Type 1 Mutant G207: Safety Evaluation in Mice, Journal of Virology, Apr. 2000, pp. 3832-3841, 74(8).

Suzuki, M. et al., Early STAT1 Activation After Systemic Delivery of HSV Amplicon Vectors Suppresses Transcription of the Vector-encoded Transgene, Molecular Therapy, Nov. 2007, pp. 2017-2026, 15(11).

Suzuki, M. et al., Stable Transgene Expression From HSV Amplicon Vectors in the Brain: Potential Involvement of Immunoregulatory Signals, Molecular Therapy, Oct. 2008, pp. 1727-1736, 16(10).

Sweeney, M.C. et al., Decoding Protein-Protein Interactions through Combinatorial Chemistry: Sequence Specificity of SHP-1, SHP-2, and SHIP SH2 Domains, Biochemistry, 2005, pp. 14932-14947, 44.

Terada, K. et al., Development of a rapid method to generate multiple oncolytic HSV vectors and their in vivo evaluation using syngeneic mouse tumor models, Gene Therapy, 2006, pp. 705-714, 2006.

Toda, M. et al., Treatment of Human Breast Cancer in a Brain Metastatic Model by G207, a Replication-Competent Multimutated Herpes Simplex Virus 1, Human Gene Therapy, Oct. 10, 1998, pp. 2177-2185, 9.

Todo, T. et al., In Situ Expression of Soluble B7-1 in the Context of Oncolytic Herpes Simplex Virus Induces Potent Antitumor Immunity, Cancer Research, Jan. 1, 2001, pp. 153-161, 61.

Toyoizumi, T. et al., Combined Therapy with Chemotherapeutic Agents and Herpes Simplex Virus Type 1 ICP34.5 Mutant (HSV-1716) in Human Non-Small Cell Lung Cancer, Human Gene Therapy, Dec. 10, 1999, pp. 3013-3029, 10.

Tridandapan, S. et al., Negative Signaling in B Cells Causes Reduced Ras Activity byReducing Shc-Grb2 Interactions, The Journal of Immunology, 1997, pp. 1125-1132.

Tridandapan, S. et al., Recruitment and Phosphorylation of SH2-Containing Inositol Phosphatase and Shc to the B-Cell Fcg Immunoreceptor Tyrosine-Based Inhibition Motif Peptide Motif, Molecular and Cellular Biology, Aug. 1997, pp. 4305-4311, 17(8).

Tridandapan, S. et al., Negative signaling in B cells: SHIP Grbs Shc, Immunology Today, Sep. 1997, pp. 424-427, 18(9).

Tridandapan, S. et al., Role of Ship in FcyRIIb-mediated inhibition of Ras activation in B cells, Molecular Immunology, 1998, pp. 1135-1146, 35.

Tridandapan, S. et al., Protein Interactions of Src Homology 2 (SH2) Domain-Containing Inositol Phosphatase (SHIP): Association with Shc Displaces SHIP from FcyRIIb in B Cells, The Journal of Immunology, 1999, pp. 1408-1414.

Tridandapan, S. et al., The Adapter Protein LAT Enhances Fcg Receptor-mediated Signal Transduction in Myeloid Cells, The Journal of Biological Chemistry, Jul. 7, 2000, pp. 20480-20487, 275(27).

Tridandapan, S. et al., Src Homology 2 Domain-Containing Inositol Polyphosphate Phosphatase Regulates NF-κb-Mediated Gene Transcription by Phagocytic FcyRs in Human Myeloid Cells, The Journal of Immunology, 2002, pp. 4370-4378.

Tridandapan, S. et al., Regulated Expression and Inhibitory Function of FcyRIIb in Human Monocytic Cells, The Journal of Biological Chemistry, Feb. 15, 2002, pp. 5082-5089, 277(7).

Tridandapan, S. et al., TGF-β1 Suppresses Myeloid Fcy Receptor Function by Regulating the Expression and Function of the Common y-Subunit, The Journal of Immunology, 2003, pp. 4572-4577.

Trotta, R. et al., Differential expression of SHIP1 in CD56bright and CD56dim NK cells provides a molecular basis for distinct functional responses to monokine costimulation, Blood, Apr. 15, 2005, pp. 3011-3018, 105(8).

Tyler, M.A. et al., Neural stem cells target intracranial glioma to deliver an oncolytic adenovirus in vivo, Gene Therapy, 2009, pp. 262-278, 16.

Tyminski, E. et al., Brain Tumor Oncolysis with Replication-Conditional Herpes Simplex Virus Type 1 Expressing the Prodrug-Activating Genes, CYP2B1 and Secreted Human Intestinal Carboxylesterase, in Combination with Cyclophosphamide and Irinotecan, Cancer Res, Aug. 1, 2005, pp. 6850-6857, 65(15).

Ulbricht, U. et al., RNA interference targeting protein tyrosine phosphatase Vreceptor-type protein tyrosine phosphatase β suppresses glioblastoma growth in vitro and in vivo, Journal of Neurochemistry, 2006, pp. 1497-1506, 98.

Utomo, A.R.H. et al., Temporal, spatial, and cell type—specific control of Cre-mediated DNA recombination in transgenic mice, Nature Biotechnology, Nov. 17, 1999, pp. 1091-1096, 17.

Varghese, S. et al., Oncolytic herpes simplex virus vectors for cancer virotherapy, Cancer Gene Therapy, 2002, pp. 967-978, 9.

Vargová, L. et al., Diffusion Parameters of the Extracellular Space in Human Gliomas, GLIA, 2003, pp. 77-88, 42.

Vetter, D. et al., Site-specific recombination of yeast 2-μm DNA in vitro, Proc. Natl. Acad. Sci. USA, Dec. 1983, pp. 7284-7288, 80.

Viapiano, M.S. et al., Novel Tumor-Specific Isoforms of BEHAB/Brevican Identified in Human Malignant Gliomas, Cancer Res, Aug. 1, 2005, pp. 6726-6733, 65(15).

Viapiano, M.S. et al., From barriers to bridges: chondroitin sulfate proteoglycans in neuropathology, Trends in Molecular Medicine, 2006, pp. 488-496, 12(10).

Volpert, O.V. et al., Inducer-stimulated Fas targets activated endothelium for destruction by anti-angiogenic thrombospondin-1 and pigment epithelium-derived factor, Nature Medicine, Apr. 2002, pp. 349-357, 8(4).

Vredenburgh, J.J. et al., Phase II Trial of Bevacizumab and Irinotecan in Recurrent Malignant Glioma, Clin Cancer Res, Feb. 15, 2007, pp. 1253-1595, 13(4).

Wade-Martins, R. et al., An infectious transfer and expression system for genomic DNA loci in human and mouse cells, Nature Biotechnology, Nov. 2001, pp. 1067-1070, 19.

Wakimoto, H. et al., The Complement Response Against an Oncolytic Virus Is Species-Specific in Its Activation Pathways, Molecular Therapy, Mar. 2002, pp. 275-282, 5(3).

Wakimoto, H. et al., Effects of innate immunity on herpes simplex virus and its ability to kill tumor cells, Gene Therapy, 2003, pp. 983-990, 10.

Wakimoto, H. et al., Altered expression of antiviral cytokine mRNAs associated with cyclophosphamide's enhancement of viral oncolysis, Gene Therapy, 2004, pp. 214-223, 11.

Wang, Y. et al., SHIP2 is Recruited to the Cell Membrane upon Macrophage Colony-Stimulating Factor (M-CSF) Stimulation and Regulates M-CSF-Induced Signaling, The Journal of Immunology, 2004, pp. 6820-6830.

Wang, Y. et al., The Role of the NADPH Oxidase Complex, p38 MAPK, and Akt in Regulating Human Monocyte/Macrophage Survival, American Journal of Respiratory Cell and Molecular Biology, 2007, pp. 68-77, 36.

Wei, M.X. et al., Experimental Tumor Therapy in Mice Using the Cyclophosphamide-Activating Cytochrome P450 2B1 Gene, Human Gene Therapy, Aug. 1994, pp. 969-978, 5.

Weir, N.M. et al., Curcumin Induces G2/M Arrest and Apoptosis in Cisplatin-Resistant Human Ovarian Cancer Cells by Modulating Akt and p38 MAPK, Cancer Biol Ther., Feb. 2007, pp. 178-184, 6(2).

Weissleder, R. et al., In vivo magnetic resonance imaging of transgene expression, Nature Medicine, Mar. 2000, pp. 351-354, 6(3).

Wierdl, M. et al., Sensitization of Human Tumor Cells to CPT-11 via Adenoviral-mediated Delivery of a Rabbit Liver Carboxylesterase, Cancer Research, Jul. 1, 2001, pp. 5078-5082, 61.

Wierdl, M. et al., Carboxylesterase-Mediated Sensitization of Human Tumor Cells to CPT-11 Cannot Override ABCG2-Mediated Drug Resistance, Molecular Pharmacology, 2003, pp. 279-288, 64(2).

Wilcox, M.E. et al., Reovirus as an Oncolytic Agent Against Experimental Human Malignant Gliomas, Journal of the National Cancer Institute, Jun. 20, 2001, pp. 903-912, 93(12).

Willmon, C. et al., Cell Carriers for Oncolytic Viruses: Fed Ex for Cancer Therapy, Molecular Therapy, Oct. 2009, pp. 1667-1676, 17(10).

Xie, D. et al., Breast Cancer, The Journal of Biological Chemistry, Apr. 27, 2001, pp. 14187-14194, 276(17).

Xie, D. et al., Cyr61 is Overexpressed in Gliomas and Involved in Integrin-Linked Kinase-Mediated Akt and β-Catenin-TCF/Lef Signaling Pathways, Cancer Research, Mar. 15, 2004, pp. 1987-1996, 64.

Xie, D. et al., Levels of Expression of CYR61 and CTGF Are Prognostic for Tumor Progression and Survival of Individuals with Gliomas, Clinical Cancer Research, Mar. 15, 2004, pp. 2072-2081, 10.

Xiong, Z. et al., Imaging Chemically Modified Adenovirus for Targeting Tumors Expressing Integrin αvβ3 in Living Mice with Mutant Herpes Simplex Virus Type 1 Thymidine Kinase PET Reporter Gene, The Journal of Nuclear Medicine, Jan. 2006, pp. 130-139, 47(1).

Yamagata, T. et al., Purification and Properties of Bacterial Chondroitinases and Chondrosulfatases, The Journal of Biological Chemistry, Apr. 10, 1968, pp. 1523-1535, 243(7).

Yamamoto, S. et al., Imaging immediate-early and strict-late promoter activity during oncolytic herpes simplex virus type 1 infection and replication in tumors, Gene Therapy, 2006, pp. 1731-1736, 13.

Yang, G.P. et al., Cyr6I, Product of a Growth Factor-inducible Immediate Early Gene, is Associated with the Extracellular Matrix and the Cell Surface, Cell Growth & Differentiation, Jul. 1991, pp. 351-357, 2.

Yang, W.Q. et al., Reovirus Prolongs Survival and Reduces the Frequency of Spinal and Leptomeningeal Metastases from Medulloblastoma, Cancer Research, Jun. 15, 2003, pp. 3162-3172, 63.

Yong, R.L. et al., Human Bone Marrow—Derived Mesenchymal Stem Cells for Intravascular Delivery of Oncolytic Adenovirus Δ24-RGD to Human Gliomas, Cancer Res, Dec. 1, 2009, pp. 8932-8940, 69(23).

Zamecnik, J., The extracellular space and matrix of gliomas, Acta Neuropathol, 2005, pp. 435-442, 110.

Zeh, H.J. et al., Development of a replication-selective, oncolytic poxvirus for the treatment of human cancers, Cancer Gene Therapy, 2002, pp. 1001-1012, 9.

Zhang, M. et al., Nestin and CD133: valuable stem cell-specific markers for determining clinical outcome of glioma patients, Journal of Experimental & Clinical Cancer Research, 2008, 7 pages, 27(85).

Zhang, S-C. et al., In vitro differentiation of transplantable neural precursors from human embryonic stem cells, Nature Biotechnology, Dec. 2001, pp. 1129-1133, 19.

Zhang, Y. et al., Inducible site-directed recombination in mouse embryonic stem cells, Nucleic Acids Research, 1996, pp. 543-548, 24(4).

Zhao, D. et al., Neural Stem Cell Tropism to Glioma: Critical Role of Tumor Hypoxia, Mol Cancer Res, Dec. 2008, pp. 1819-1829, 6(12).

Zhao, X. et al., Targeting CD37-positive lymphoid malignancies with a novel engineered small modular immunopharmaceutical, Blood, Oct. 2007, pp. 2569-2577, 110(7).

Zheng, S. et al., Fiber-knob modifications enhance adenoviral tropism and gene transfer in malignant glioma, The Journal of Gene Medicine, 2007, pp. 151-160, 9.

Zhou, G. et al., Separation of receptor-binding and profusogenic domains of glycoprotein D of herpes simplex virus 1 interacting proteins, PNAS, Mar. 6, 2007, pp. 4142-4146, 104(10).

\* cited by examiner

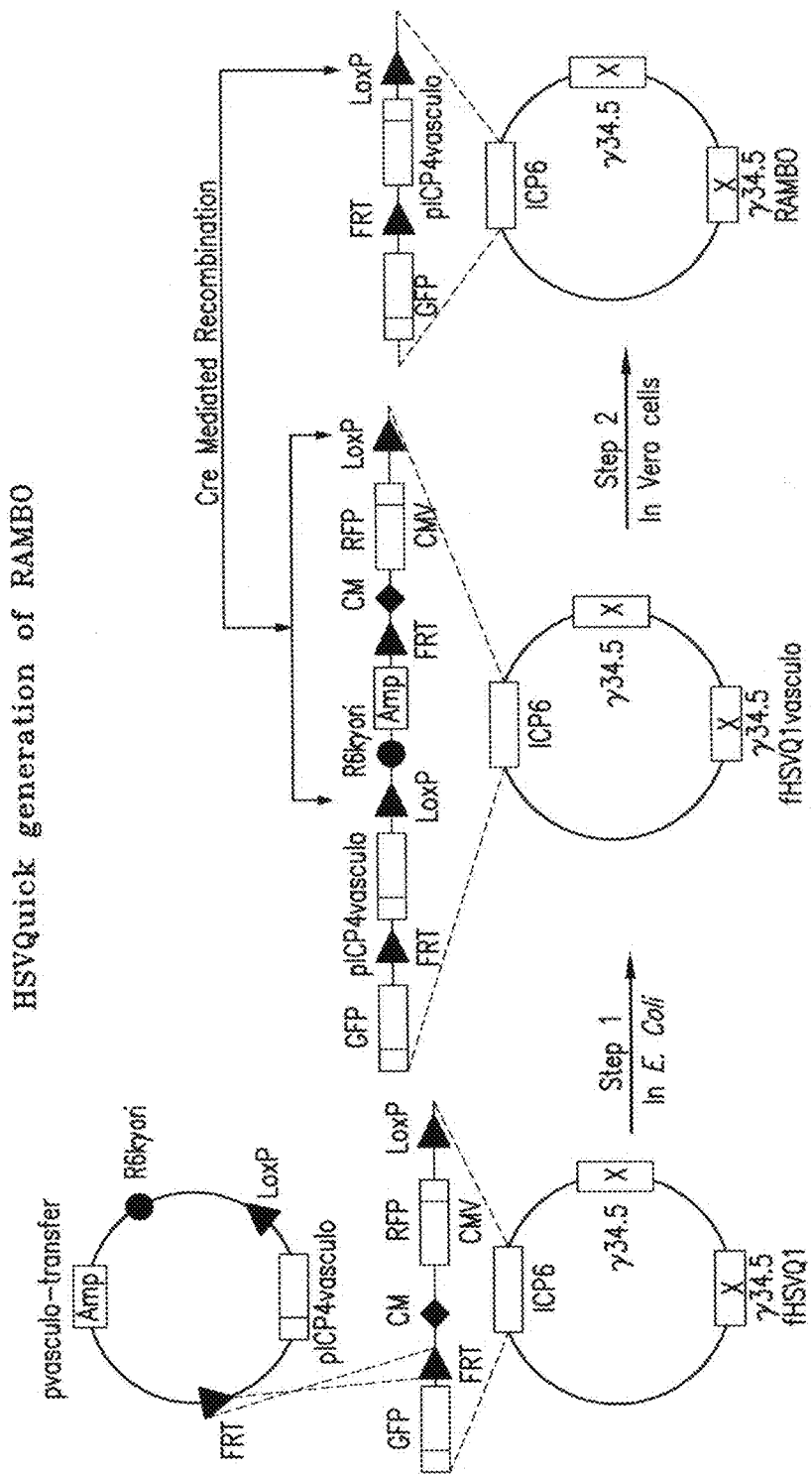

FIG-3

Overview of the steps involved in the construction of RAMBO. Step 1: Flp-mediated site specific recombination of fHSVQ1 with pvasculo-transfer in E. Coli results in the incorporation of entire pvasculo transfer into fHSVQ1 BAC. Step 2: Cre-mediated recombination in Vero cells results in excision of the bacterial sequences from fHSVQ1vasculo resulting in the generation of GFP positive and RFP negative RAMBO virus.

ONCOLYTIC VIRUS

CROSS-REFERENCE TO RELATED APPLICATIONS

This non-provisional application claims the priority benefit of U.S. Provisional Patent Application No. 61/256,644, filed Oct. 30, 2009 and U.S. Provisional Patent Application No. 61/148,870, filed Jan. 30, 2009. This non-provisional application is also a continuation of International Patent Application No. PCT/US2008/080367, filed Oct. 17, 2008, which claims the priority benefit of U.S. Provisional Patent Application No. 60/980,664, filed Oct. 17, 2007. All of the above referenced applications are hereby incorporated by reference in their entirety.

TECHNICAL FIELD

The present invention is directed to the fields of virology, cancer biology, and medicine. More particularly, it concerns compositions and methods of treating cancer of the brain in a patient using oncolytic herpes simplex virus 1(HSV-1) armed with therapeutic transgenes.

BACKGROUND OF THE ART

Malignant tumors that are intrinsically resistant to conventional therapies are significant therapeutic challenges. Such malignant tumors include, but are not limited to malignant gliomas and recurrent systemic solid tumors such as lung cancer. Malignant gliomas are the most abundant primary brain tumors having an annual incidence of 6.4 cases per 100,000 (CBTRUS, 2002-2003). These neurologically devastating tumors are the most common subtype of primary brain tumors and are one of the deadliest human cancers. In the most aggressive cancer, manifestation glioblastoma multiforme (GBM), median survival duration for patients is 14 months, despite maximum treatment efforts. A prototypic disease, malignant glioma is inherently resistant to current treatment regimens. In fact, in approximately ⅓ of patients with GBM the tumor will continue to grow despite treatment with radiation and chemotherapy. Median survival even with aggressive treatment including surgery, radiation, and chemotherapy is less than 1 year (Schiffer, 1998). Because few good treatment options are available for many of these refractory tumors, the exploration of novel and innovative therapeutic approaches is essential.

Gene therapy is a promising treatment for tumors including gliomas because conventional therapies typically fail and are toxic. In addition, the identification of genetic abnormalities contributing to malignancies is providing crucial molecular genetic information to aid in the design of gene therapies. Genetic abnormalities indicated in the progression of tumors include the inactivation of tumor suppressor genes and the overexpression of numerous growth factors and oncogenes. Tumor treatment may be accomplished by supplying a polynucleotide encoding a therapeutic polypeptide or other therapeutic that target the mutations and resultant aberrant physiologies of tumors. It is these mutations and aberrant physiology that distinguishes tumor cells from normal cells. A tumor-selective virus would be a promising tool for gene therapy. Recent advances in the knowledge of how viruses replicate have been used to design tumor-selective oncolytic viruses.

In gliomas, several kinds of conditionally replication competent viruses have been shown to be useful in animal models for example: reoviruses that can replicate selectively in tumors with an activated ras pathway (Coffey et al., 1998); genetically altered herpes simplex viruses (Martuza et al., 1991; Mineta et al., 1995; Andreanski et al., 1997), including those that can be activated by the different expression of proteins in normal and cancer cells (Chase et al., 1998); and mutant adenoviruses that are unable to express the E1B55 kDa protein and are used to treat p53-mutant tumors (Bischof et al., 1996; Heise et al., 1997; Freytag et al., 1998; Kim et al., 1998). Taken together, these reports confirm the relevance of oncolytic viruses as anti-cancer agents. In all three systems, the goal is the intratumoral spread of the virus and the ability to selectively kill cancer cells. Along with directly killing the cancers cells, agents that can also influence the microenvironment surrounding the tumor may enhance the therapeutic effect of the OV.

Replication selective oncolytic viruses have shown great promise as anti-tumor agents for solid tumors. The viruses have been constructed genetically so that they are able to preferentially replicate within tumor cells, while being restricted in their ability to replicate in normal cells. The principal anti-tumor mechanism of oncolytic viruses is through a direct cytopathic effect as they propagate and spread from initially infected tumor cells to surrounding tumor cells, achieving a larger volume of distribution and anticancer effects. Oncolytic herpes simplex virus (HSV) were initially designed and constructed for the treatment of brain tumors. Subsequently, they have been found to be effective in a variety of other human solid tumors, including breast, prostate, lung, ovarian, colon and liver cancers. The safety of oncolytic HSVs has also been extensively tested in mice and primates (Aotus), which are extremely sensitive to HSV.

HSV-1 based oncolytic viruses are particularly exciting because of: 1) their ability to infect a wide variety of tumors; 2) their inherent cytolytic nature; 3) their well characterized large genome (152 Kb) that provides ample opportunity for genetic manipulations wherein many of the non-essential genes (up to 30 kb) can be replaced by therapeutic genes; 4) their ability to remain as episomes that avoid insertional mutagenesis in infected cells; and 5) the availability of anti-herpetic drugs to keep in check possible undesirable replication.

Despite these encouraging preclinical studies, results from early clinical trials have suggested that the current versions of oncolytic viruses, although safe, may only have limited anti-tumor activity on their own. One of the main reasons for the sub-optimal oncolytic efficacy is probably because viral gene deletions that confer tumor selectivity also result in reduced potency of the virus in tumors. For example, the complete elimination of endogenous γ34.5 function from HSV, one of the common approaches for the construction of oncolytic HSV, significantly reduces viral replication potential and therefore may compromise the ability of the virus to spread within the targeted tumors (Kramm et al., 1997). Therefore, strategies designed to further enhance the potency of oncolytic viruses will likely increase their chance of clinical success.

The tumor microenvironment is also recognized as an important determinant for tumor progression. Vasculature is a major component of the microenvironment of solid tumors such as malignant gliomas. Solid tumors depend on the development of a vasculature to provide them with nutrients. While tumor oncolysis is thought to set the stage for activating a systemic adaptive immune surveillance, innate defense mechanisms elicited upon OV infection are thought to be responsible for rapid viral clearance from tumor. Thus, OV-induced inflammation and its attendant increased vasculature may be counterproductive to the goal of killing cancer cells.

Therefore, there is an unmet need for an OV therapy that is tumor selective yet robust enough to kill tumor cells over an organism's natural defenses.

SUMMARY

Embodiments address a long-felt need in the art by providing a potent oncolytic virus for therapy of undesirable cells, such as malignant cells.

A preferred embodiment provides an oncolytic virus capable of killing target cells, such as a tumor cells. In preferred embodiments, the conditionally replicating HSV comprises at least two mechanisms to rid a culture, tissue or organism of at least some undesirable cells, to inhibit proliferation of at least some undesirable cells, to prevent proliferation of at least some desirable cells, or a combination thereof. A preferred embodiment may not only directly act on the cancer itself, but also may enhance tumor cell killing by influencing the microenvironment around the physical tumor.

In various embodiments presented herein, the oncolytic virus is armed or encodes a therapeutic polypeptide. "Armed" is a term that indicates that the virus contains a heterologous nucleic acid sequence encoding a polypeptide of interest or a nucleic acid comprising a polynucleotide of interest. In certain embodiments, the nucleic acid encoding a therapeutic polypeptide may encode an angiostatic factor. In various embodiments, the nucleic acid encoding a therapeutic polypeptide encodes the polypeptide Vasculostatin. In an alternative embodiment, the transgene encodes an enzyme that can depolymerize at least a portion of the extracellular matrix scaffold. Preferably, the transgene encodes a chondroitinase ABC 1 (Chase ABC), a bacterial enzyme. In yet another embodiment, the oncolytic virus may be armed with multiple heterologous nucleic acid sequences, for example, the oncolytic virus may contain transgenes encoding both Vasculostatin and Chase ABC.

In various embodiments, the OV comprises a transcriptionally targeted OV wherein at least one of the deleted ICP34.5 genes may be reinserted into the HSVQ backbone, under the transcriptional control of a glioma specific nestin enhancer element. In at least one such exemplary embodiment, the OV is a Vasculostatin expressing virus within the rQnestin34.5 virus backbone. In another such exemplary embodiment, the OV is a Chase ABC expressing virus within the rQnestin34.5 virus backbone.

Oncolytic viruses expressing angiostatic factors using a CMV promoter have demonstrated limited efficacy in rodent models of glioma (for example, US Pub. No. 2006/0147420 and US Pub. No. 2004/0009604, incorporated herein by reference). Given the rapid lytic cycle of HSV, the challenge has been to ensure robust expression of the therapeutic protein before lysis of the infected cell.

Disclosed herein, a preferred embodiment overcomes this challenge by utilizing the immediate early HSV promoter IE4/5 operably linked to a therapeutic transgene. In at least one embodiment, the transgene is angiostatic. In a preferred embodiment, the transgene is a novel, brain specific angiostatic polypeptide, Vasculostatin. In another embodiment, the transgene is Chase ABC, a bacterial enzyme. In a preferred embodiment, robust expression of a therapeutic gene can be seen at least as early as 4 hours.

In various embodiments, the transgene encodes an enzyme that can depolymerize at least a portion of the extracellular matrix scaffold. Preferably, the transgene encodes a chondroitinase ABC 1 (Chase ABC), a bacterial enzyme. The ECM forms an inhibitory scaffold organized by CSPGs that bind the HA scaffold, other key matrix molecules (tenascins and link proteins) and cellular receptors (CD44, NCAM, integrins, etc). This scaffold inhibits the spread of infectious OV particles from one infected cell (bottom) to the next (top). A preferred embodiment overcomes this obstacle by utilizing the immediate early HSV promoter IE4/5 operably linked to a nucleic acid that encodes a chondroitinase ABC 1 (Chase ABC). An exemplary embodiment gains increased therapeutic efficacy by delivering Chondroitinase ABC in tumors to increase dispersal of a large therapeutic molecule(s). Furthermore, an exemplary embodiment combines the use of an oncolytic virus (OV) with an HSV immediate early IE 4/5 viral promoter that drives expression of a secreted glycosidase as a means of increasing viral dispersal in tumors. The oncolytic virus of an exemplary embodiment can be delivered by a number routes including, but not limited to intracranial (into the skull cavity) intra-tumoral or intravenous administration. The tumor may be a primary tumor or it may be a tumor resulting from a metastasis to the skull or brain.

In an exemplary embodiment, a recombinant oncolytic virus has been generated that can specifically replicate in cancer cells leading to their destruction and at the same time secrete robust amounts of an angiostatic factor to inhibit the regrowth of residual disease. Such a dually armed OV destroys cancer cells through its tumor specific replication potential and also targets tumor vasculature to enhance therapeutic efficacy.

In a preferred embodiment, a dually armed OV has been generated and shown that it does express and secrete the therapeutic anti-angiogenic factor (Vasculostatin), a novel brain specific anti-angiogenic factor, even at early time points after infection. One embodiment, an embodiment referred to herein as RAMBO (Rapid Anti-angiogenesis Mediated By Oncolytic virus) is a Vasculostatin expressing virus within a HSVQ backbone. In another embodiment, an embodiment referred to herein as Nested-RAMBO, is a Vasculostatin expressing virus within the rQnestin34.5 virus backbone (see Kambara, H.; Okano, H.; Chiocca, E. A. Saeki, Y. An oncolytic HSV-1 mutant expressing ICP34.5 under control of a nestin enhancer element increases survival of animals even when symptomatic from a brain tumor. *Cancer Res* 2005, 65, 2832-9, expressly incorporated by reference in its entirety.) In various embodiments, Vasculostatin is operably linked to and expressed under the control of an HSV immediate early IE4/5 promoter.

In order to maximize the expression of Vasculostatin, at least one embodiment exploits the robust transgene expression from an early viral promoter to maximize the expression of Vasculostatin. The expression profile of a preferred embodiment allows for maximal expression of therapeutic transgenes before the lytic phase. At least one embodiment has shown efficacy in mice with established brain tumors. Compositions and methods disclosed herein have broad therapeutic applicability to most solid cancers.

Accordingly, embodiments include a recombinant expression vector comprising a nucleic acid comprising a nucleotide sequence encoding a therapeutic polypeptide operably linked to an immediate early HSV promoter IE4/5. In some embodiments the vector is a modified herpes simplex virus. In various embodiments, the modified herpes simplex virus is a mutant herpes simplex virus deficient for both copies of its native $\gamma_1 34.5$ gene. In exemplary embodiments, the therapeutic polypeptide may comprise Vasculostatin, a proteolytic polypeptide fragment of BAI1. In alternative embodiments, the therapeutic polypeptide comprises a Chase ABC polypeptide.

Various embodiments comprise a recombinant Herpes Simplex Virus, comprising: a nucleic acid comprising a nucleotide sequence of SEQ ID NO: 1 or SEQ ID NO: 6, or of a degenerate variant of SEQ ID NO: 1 or SEQ ID NO: 6, operably linked to an expression control sequence. The expression control sequence may be an immediate early HSV promoter IE4/5. In various embodiments, the expression control sequence comprises the nucleotide sequence of SEQ ID NO: 5.

In some embodiments, the recombinant Herpes Simplex Virus is deficient for both copies of its native $\gamma_1 34.5$ gene. However, various embodiments include a nucleic acid comprising a nucleotide sequence encoding a replacement $\gamma_1 34.5$ gene to conditionally restore this deficiency. In preferred embodiments, the replacement $\gamma_1 34.5$ gene is operably linked to a tumor specific promoter.

Exemplary embodiments include a method of killing intracranial tumor cells in a mammal comprising introducing into the vicinity of the tumor cells an expression vector, the vector comprises a modified herpes virus deficient for both copies of its native $\gamma_1 34.5$ gene; a nucleic acid comprising a nucleotide sequence of SEQ ID NO: 1, or of a degenerate variant of SEQ ID NO: 1, operably linked to an expression control sequence; and a nucleic acid encoding a replacement $\gamma_1 34.5$ gene, the replacement $\gamma_1 34.5$ gene is operably linked to a nestin enhancer element. In some embodiments, the expression control sequence comprises an immediate early HSV promoter IE4/5. In various embodiments, the method further comprises the step of mixing a pharmacologically acceptable carrier with the expression vector prior to the introducing step.

Embodiments include compositions comprising a vector comprising: a nucleic acid encoding the polypeptide Vasculostatin operably linked to an immediate early HSV IE4/5 promoter. In alternative embodiments, the composition comprises a vector comprising: a nucleic acid encoding the polypeptide Chase ABC operably linked to an immediate early HSV IE4/5 promoter. In various embodiments, the vector is a mutant Herpes Simplex Virus comprising a nucleic acid encoding a replacement $\gamma_1 34.5$ gene inserted into an otherwise $\gamma_1 34.5$-deleted viral genome, the replacement $\gamma_1 34.5$ gene is operably linked to a tumor specific promoter. Preferably, the tumor specific promoter comprises a nestin enhancer element.

Embodiments comprises a recombinant expression vector comprising a nucleic acid comprising a nucleotide sequence encoding a Chase ABC polypeptide operably linked to an immediate early HSV promoter IE4/5. In various embodiments the vector is a modified herpes simplex virus. In some embodiments, the modified herpes simplex virus is deficient for both copies of its native $\gamma_1 34.5$ gene. In exemplary embodiments, the nucleic acid sequence encoding a Chase ABC polypeptide comprises the nucleotide sequence of SEQ ID NO: 6 or of a degenerate variant of SEQ ID NO: 6.

In exemplary embodiments, expression of the therapeutic transgene (e.g., Vasculostatin and/or Chase ABC) is functional and does not interfere with the virus's cytotoxicity toward tumor cells (e.g., glioma cells). Additionally, the generated OV has therapeutic advantage over the control virus for the treatment of mice with established brain tumors.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of a preferred embodiment. The invention may be better understood by reference to one or more of these drawings in combination with the detailed description of specific embodiments presented herein:

FIG. 3 provides a schematic illustration of the steps utilized to generate the OV, rHSVQvasculo (also called "RAMBO")

DETAILED DESCRIPTION

Figure 1:
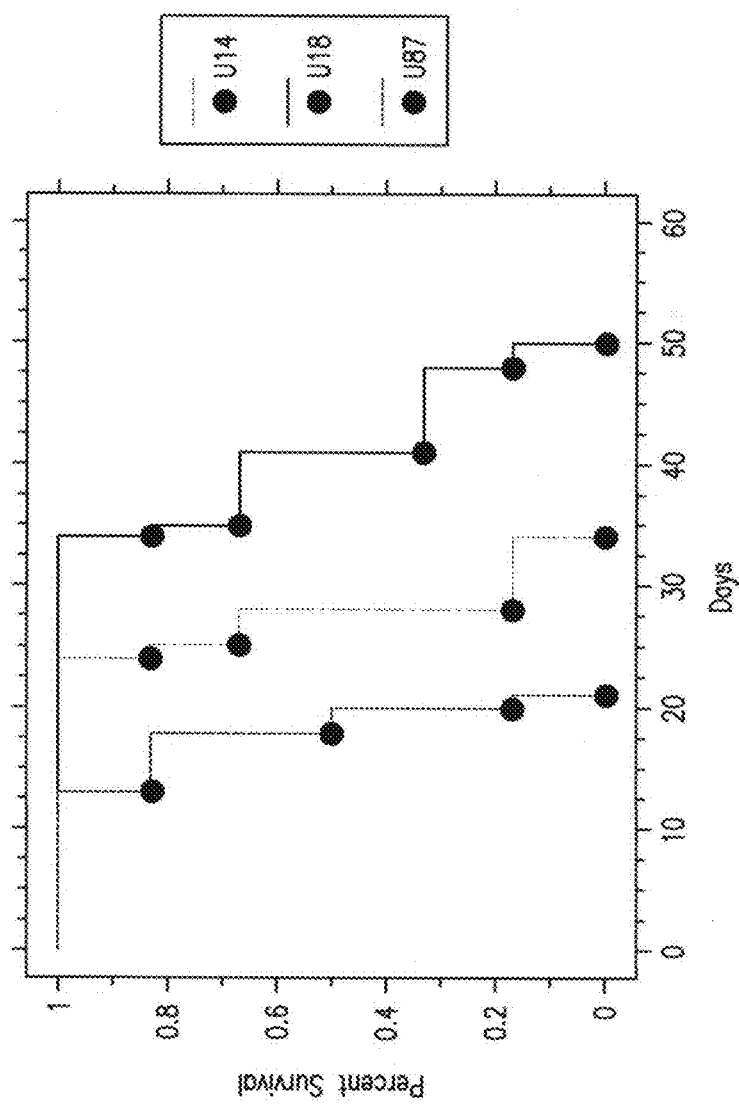
FIG. 1 shows the survival of rats implanted with U87 human glioma cells stably expressing Vasculostatin (clones U14 and U18) with parental untransfected glioma cells (U87). Note that survival of rats implanted with cells expressing Vasculostatin was significantly greater than that of rats implanted with control parental U87MG cells ($P<0.05$). (Kaur et al., unpublished results).

Gliomas are the most common primary tumors of the central nervous system (CNS). Glioblastoma multiforme (GBM), the most aggressive form (WHO grade IV) of malignant astrocytoma, is highly invasive and vascularized [40] and characterized by 1) rapidly proliferating endothelial cells that form tufted aggregates referred to as glomeruloid bodies and 2) multiple hypoxic-necrotic areas within the tumor that drive hypoxia-mediated activation of hypoxia inducible factor (HIF), which thereby leads to increased transcription of factors, such as vascular endothelial growth factor (VEGF), that heralds a phase of more malignant tumor growth [41]. Their very aggressive growth and highly vascular nature makes malignant gliomas an attractive target for testing the effects of anti-angiogenic gene therapy. The increased vascularization essential for malignant progression is triggered by disruption of the normal homeostasis between angiogenic and angiostatic factors within the tumor microenvironment. It has been shown that expression of angiogenesis inhibitors is reduced in GBMs but not in normal brain and benign gliomas. Although not to be limited by theory, physiologically occurring factors that inhibit angiogenesis which are lost during tumor progression should represent molecules of choice for restoration by gene therapy.

Vasculostatin, a fragment of Brain Angiogenesis inhibitor 1 (BAI1) (GenBank Accession No. AB005297), can inhibit angiogenesis, permeability, and subcutaneous as well as intracerebral tumor growth. Vasculostatin 1) is expressed at high levels primarily in normal brain but not in most GBMs and 2) has potent anti-angiogenic, anti-tumorigenic, and anti-permeability properties and 3) the ability to target multiple receptors on endothelial cells ($\alpha v \beta 3$, $\alpha v \beta 5$, and CD36), and 4) its over expression is well tolerated in brain tissue. Hence, Vasculostatin may be a better candidate than other more popular and not so novel anti-angiogenic factors for therapy of GBMs.

HSV-1-derived OVs that express endostatin and, more recently, oncolytic viruses that express platelet factor IV and dominant negative FGF receptor under the control of a CMV promoter have been described. However, at least one embodiment disclosed herein is better for GBM therapy because of its combination with an IE4/5 promoter (SEQ ID NO: 5) that drives the expression of the transgene to levels unseen with a CMV promoter. More particularly, in certain embodiments disclosed herein Vasculostatin, a novel angiostatic factor, has been successfully expressed as part of an oncolytic viral strategy and shown to successfully counter anti-therapeutic changes in residual disease after oncolysis.

Specific replication within tumor cells can be achieved by OVs genetically engineered for that purpose or by naturally occurring strains of some viruses that have such propensity [25]. Specific embodiments utilize one such mutant, designated G207, which comprises an F-strain derived HSV-1 with deletions in both copies of the $\gamma_1 34.5$ gene (encoding for the viral ICP34.5 protein) and an inactivating insertion of *Escherichia coli* (*E. coli*) lacZ into the viral ICP6/RR gene (encoding for the large subunit of ribonucleotide reductase). The available human evidence shows that the injection of HSV-1 with $\gamma_1 34.5$ deletion (and intact vhs) does not lead to the reactivation of wild-type HSV-1, produce toxicity from infection of neurons surrounding the glioma cavity, or lead to encephalitis or meningitis.

HSV-1 infection of cells activates, a cellular "stress" or "defense" response consisting of activation of the PKR (double stranded RNA protein kinase) enzyme, ultimately leading to blockage of protein synthesis. HSV1 gene product ICP34.5 ($\gamma_1 34.5$) activates a cellular phosphatase (PP1$\alpha$) that dephosphorylates eiF2$\alpha$, thus allowing for viral protein translation and replication to occur. Complete deletion of ICP34.5 severely attenuates the replication potential of oncolytic HSV, and this has been deleted in clinical viruses tested to date. Various embodiments overcome this replication deficiency using tumor specific promoters to drive viral potency. More specifically, various embodiments include a transcriptionally targeted OV, wherein at least one copy of the $\gamma_1 34.5$ gene may be conditionally expressed under the governance of a nestin enhancer element when this expression cassette is reinserted into a $\gamma_1 34.5$ null OV backbone.

Angiogenesis is critical for the development and maintenance of glioblastomas, the most malignant and common form of primary brain tumors. Combining oncolysis with anti-angiogenesis may produce a synergistic effect since the anti-cancer mechanisms are different but complementary. A preferred embodiment allows an anti-angiogenic nucleic acid or polypeptide, such as, but not limited to a Vasculostatin protein, to be produced, ultimately favoring delivery to the extracellular compartment. For that reason, the oncolytic HSV-1 is used as an improved HSV vector to deliver high and continuous levels of Vasculostatin to the tumor.

Angiogenesis refers to vessel formation by remodeling the primary vascular network or by sprouting from existing vessels (reviewed in Yancopoulos et al., 2000). The "angiogenesis switch" is "off" when the effect of pro-angiogenic molecules is balanced by the activity of anti-angiogenic molecules, and is "on" when the net balance between the molecules is tipped in favor of angiogenesis (reviewed in Carmeliet and Jain, 2000). Angiogenesis has an essential role in the development and maintenance of solid tumors, including malignant gliomas.

One of the major barriers for effective drug delivery within the tumor parenchyma is the ubiquitous extracellular matrix (ECM) secreted by glioma cells. This matrix forms a complex scaffold that modulates tumor cell proliferation, cell adhesion, and motility. Glioma ECM is based on a scaffold of hyaluronic acid (HA) with associated glycoproteins and proteoglycans, which resemble the composition of the normal brain ECM. However, the ECM of gliomas also includes mesenchymal proteins that are absent in normal brain and that make the matrix of these tumors distinct from the ECM of normal neural tissue and of other solid tumors. Increased expression and extracellular accumulation of ECM reduces the interstitial spaces and increases the internal pressure in the tumor. This leads to an increase in the fractional volume and tortuosity of the extracellular space, which are the major biophysical factors that limit passive molecular diffusion in the tumor tissue and are limiting for spread of therapeutics.

Inefficient viral dispersal through the tumor interstitium can lead to poor viral spread hence not permitting efficient tumor cell infection and oncolysis. Efforts to increase viral spread within the tumor should lead to improved efficacy. Glioma extracellular matrix (ECM) poses a significant barrier for efficient viral spread through the tumor, and hence limits its efficacy. Chondroitin sulfate proteoglycans (CSPG) are one of the major inhibitory components of glioma ECM. A specific bacterial glycosidase, such as Chondroitinase ABC 1 (Chase ABC) can depolymerize this ECM scaffold to provide a long-lasting "loosening" effect on the inhibitory scaffold. Accordingly, in various exemplary embodiments, Chase ABC mediated digestion of glioma CSPG may enhance OV dissemination and efficacy.

Embodiments of this invention may include multiple other heterologous genes. For example, they may include therapeutic genes, pro-drug converting enzymes, cytosine deaminase (to convert 5-FC to 5-FU), a yeast cytosine deaminase, a humanized yeast cytosine deaminase, an image enhancing polypeptides, a sodium-iodide symporter, anti-sense or inhibitory VEGF, Bcl-2, Ang-2, or interferons alpha, beta or gamma.

In describing the exemplary embodiments, the following terms will be employed, and are intended to be defined as indicated below.

The term "recombinant HSV-1 vector" as used herein defines a recombinant HSV-1 vector comprising: (a) the DNA of, or corresponding to, at least a portion of the genome of an HSV-1 which portion is capable of transducing into a target cell at least one selected gene and is capable of promoting replication and packaging; and (b) at least one selected gene (or transgene) operatively linked to regulatory sequences directing its expression, the gene flanked by the DNA of (a) and capable of expression in the target cell in vivo or in vitro. Thus, when referring to a "recombinant HSV" (rHSV) it is meant the HSV that has been genetically altered, e.g., by the addition or insertion of a selected gene.

A "gene," or a "sequence which encodes" a particular protein, is a nucleic acid molecule which is transcribed (in the case of DNA) and translated (in the case of mRNA) into a polypeptide in vitro or in vivo when placed under the control of appropriate regulatory sequences. The boundaries of the gene are determined by a start codon at the 5' (amino) terminus and a translation stop codon at the 3' (carboxy) terminus. A gene can include, but is not limited to, cDNA from eukaryotic mRNA, genomic DNA sequences from eukaryotic DNA, and even synthetic DNA sequences. A transcription termination sequence will usually be located 3' to the gene sequence. Typically, polyadenylation signal is provided to terminate transcription of genes inserted into a recombinant virus.

As is known to those of skill in the art, the term "polypeptide" or "protein" means a linear polymer of amino acids joined in a specific sequence by peptide bonds. As used herein, the term "amino acid" refers to either the D or L stereoisomer form of the amino acid, unless otherwise specifically designated.

The term "transgene" refers to a particular nucleic acid sequence encoding a polypeptide or a portion of a polypeptide to be expressed in a cell into which the nucleic acid sequence is inserted. The term "transgene" is meant to include (1) a nucleic acid sequence that is not naturally found in the cell (i.e., a heterologous nucleic acid sequence); (2) a nucleic acid sequence that is a mutant form of a nucleic acid sequence naturally found in the cell into which it has been inserted; (3) a nucleic acid sequence that serves to add additional copies of the same (i.e., homologous) or a similar nucleic acid sequence naturally occurring in the cell into which it has been inserted; or (4) a silent naturally occurring or homologous nucleic acid sequence whose expression is induced in the cell into which it has been inserted. By "mutant form" is meant a nucleic acid sequence that contains one or more nucleotides that are different from the wild-type or naturally occurring sequence, i.e., the mutant nucleic acid sequence contains one or more nucleotide substitutions, deletions, and/or insertions. In some cases, the transgene may also include a sequence encoding a leader peptide or signal sequence such that the transgene product may be secreted from the cell.

In a preferred embodiment, a proteolytic fragment of BAI1, Vasculostatin (also referred to herein as Vstat120), is utilized as the anti-angiogenic transgene. A preferred embodiment comprises a polypeptide having the angiostatic activity of Vasculostatin, including, but not limited to the polypeptide of SEQ ID NO:2 that is encoded by the nucleic acid sequence of SEQ ID NO:1. Additionally, the transgene may optionally include nucleotides encoding a his and/or myc tag as in SEQ ID NO:3.

In various embodiments, the OV may contain a heterologous transgene encoding an enzyme that can depolymerize at least a portion of the extracellular matrix scaffold. Preferrably, the OV comprises a heterologous nucleic acid encoding a chondroitinase ABC 1 (Chase ABC), a bacterial enzyme (SEQ ID NOS: 6 or 8), or a degenerate variant. In yet another embodiment, the oncolytic virus may be armed with multiple heterologous nucleic acid sequences, for example, the oncolytic virus may contain transgenes encoding both Vasculostatin and Chase ABC. The nucleic acid and amino acid sequence of Chase ABC enzyme provided herein is provided as SEQ ID NO: 6 and SEQ ID NO: 7, respectively. Additionally, also provided are polypeptides that comprise the amino acid sequence of SEQ ID NO: 7, and fragments thereof. The fragment can be of any size greater than 15 amino acids in length. In some embodiments the fragment is at least 20, 30, 50, 75, 125, 100, 150, 200, 250, 300, 350, 400, 450, 500, 600, 700, 800, 900, 950, 975, 990 or more amino acids in length.

The Chase ABC enzymes provided also include modified Chase ABC enzymes. Such enzymes include those that can contain amino acid substitutions (e.g., at one or more of the important amino acid residues) of native Chase ABC as provided herein. The Chase ABC enzymes provided can have altered enzymatic activity and/or substrate specificity as compared to a native Chase ABC. In some embodiments, the Chase ABC enzymes have increased enzymatic activity. In others, the Chase ABC enzymes have diminished enzymatic activity. "Modified Chase ABC enzymes", are Chase ABC enzymes that are not as they would be found in nature and are somehow altered or modified. As used herein the "sequence of a modified Chase ABC" is intended to include the sequences of the modified enzymes provided with conservative substitutions therein and functional equivalents thereof, including, but not limited to fragments of the enzymes. The nucleic acid and amino acid sequence of an exemplary modified Chase ABC is provided herein is provided as SEQ ID NO: 8 and SEQ ID NO: 9, respectively. These modified sequences in some embodiment include a heterologous signal sequence, such as a secretion signal (SEQ ID NO: 8). In other embodiments, a signal sequence is not included. Modified Chase ABC enzymes can be produced using conservative substitutions, nonconservative substitutions, deletions, additions or a multiple mutant combination. In various exemplary embodiments, nucleic acids encoding modified Chase ABC enzymes may include mutations to prevent cryptic signals in the bacterial sequence from causing inappropriate modifications in animal cells. Such mutations may be made to prevent eukaryotic N-glycosylation systems from interfering with folding and secretion of active Chase ABC, a protein whose sequence has not naturally been adapted for glycosylation in structurally appropriate locations. (See Elizabeth M. Muir, et al., Modification of N-glycosylation sites allows secretion of bacterial chondroitinase ABC from mammalian cells, Journal of Biotechnology. 2009 (article in press)); see also, U.S. Pat. No. 7,553,950, incorporated by reference herein.

The promoter operably linked to heterologous transgenes in exemplary embodiments is preferably the immediate early promoter IE4/5 (SEQ ID NO:5). However, the use of other viral or mammalian cellular or bacterial phage promoters which are well-known in the art to achieve expression of a coding sequence of interest is contemplated as well, provided that the levels of expression are sufficient for a given purpose.

A preferred embodiment provides a method for treating a neoplastic disease in a subject, the subject being an animal or human, comprising administering to the subject a therapeutically effective amount of a recombinant tumor-specific conditional replication oncolytic activity, the vector comprising a DNA sequence encoding an anti-angiogenic agent, the DNA is operably linked to a promoter. Preferably, the anti-angiogenic agent is vasculostatin (which is a fragment of brain angiogenesis inhibitor 1 (BAI1)) or a biologically active variant thereof.

The term "operably linked" refers to the arrangement of various nucleic acid molecule elements relative to each other such that the elements are functionally connected and are able to interact with each other. Such elements may include, without limitation, a promoter, an enhancer, a polyadenylation sequence, one or more introns and/or exons, and a coding sequence of a gene of interest to be expressed (i.e., the transgene). The nucleic acid sequence elements, when operably linked, act together to modulate the activity of one another, and ultimately may affect the level of expression of the transgene. By modulate is meant increasing, decreasing, or maintaining the level of activity of a particular element. Typically, transduction of the transgene of the invention increases the expression of the transgene, preferably that of the angiostatic polypeptide Vasculostatin. The position of each element relative to other elements may be expressed in terms of the 5' terminus and the 3' terminus of each element.

The term "transfection" is used to refer to the uptake of foreign DNA by a mammalian cell. A cell has been "transfected" when exogenous DNA has been introduced inside the cell membrane. A number of transfection techniques are known in the art. See, Graham et al. (1973) Virology, 52:456; and Sambrook et al. (1989) Molecular Cloning, a laboratory manual, Cold Spring Harbor Laboratories, New York. Such techniques can be used to introduce one or more exogenous DNA moieties, such as a viral vector and other nucleic acid molecules, into suitable host cells. The term refers to both stable and transient uptake of the genetic material.

The vectors of the preferred embodiments may be useful for the introduction of additional genes in gene therapy. Thus, for example, the HSV vector of this invention can contain an additional exogenous gene for the expression of a protein effective in regulating the cell cycle, such as p53, Rb, or mitosin, or a biologically active variant thereof, or in inducing cell death, such as the conditional suicide gene thymidine kinase, the latter must be used in conjunction with a thymidine kinase metabolite in order to be effective, or any other anti-tumor gene, such as for example a toxin.

As used hereafter, the terms "neoplasm" and "neoplastic" refer to a tumor and/or to an abnormal tissue, including metastatic disease, that grows by cellular proliferation more rapidly than normal, continues to grow after the stimuli that initiated the new growth cease, shows partial or complete lack of structural organization and functional coordination with normal tissue, and usually forms a distinct mass of tissue which may be either benign or malignant.

A wide variety of neoplastic diseases can be treated by the same therapeutic strategy of exemplary embodiments. Neoplastic diseases include, but are not limited to, benign solid tumors, malignant solid tumors, benign proliferative diseases of the blood, and malignant proliferative diseases of the blood. Representative examples include colon carcinoma, prostate cancer, breast cancer, lung cancer, skin cancer, liver cancer, bone cancer, ovary cancer, pancreas cancer, brain cancer, head and neck cancer, and lymphoma.

As used throughout this application, the term animal is intended to be synonymous with mammal and is to include, but not be limited to, bovine, porcine, feline, simian, canine, equine, murine, rat or human. Host cells include, but are not limited to, any neoplastic or tumor cell, such as osteosarcoma, ovarian carcinoma, breast carcinoma, melanoma, hepatocarcinoma, lung cancer, brain cancer, colorectal cancer, hematopoietic cell, prostate cancer, cervical carcinoma, retinoblastoma, esophageal carcinoma, bladder cancer, neuroblastoma, or renal cancer.

When used pharmaceutically, OVs embodiments discussed herein can be combined with various pharmaceutically acceptable carriers. Suitable pharmaceutically acceptable carriers are well known to those of skill in the art. The compositions can then be administered therapeutically or prophylactically, in effective amounts, described in more detail below.

As used herein, the term "therapeutically effective amount" is intended to mean the amount of vector or of transformed cells, which exerts oncolytic activity, causing attenuation or inhibition of tumor cell proliferation leading to tumor regression. An effective amount will vary on the pathology or condition to be treated, by the patient and his status, and other factors well known to those of skill in the art. Effective amounts are easily determined by those of skill in the art.

The term "oncolytic activity" as used herein refers to cytotoxic effects in vitro and/or in vivo exerted on tumor cells without any appreciable or significant deleterious effects to normal cells under the same conditions. The cytotoxic effects under in vitro conditions are detected by various means as known in prior art, for example, by staining with a selective stain for dead cells, by inhibition of DNA synthesis, or by apoptosis. Detection of the cytotoxic effects under in vivo conditions is performed by methods known in the art.

Methods of treating a neoplastic disease may include administration of the compounds of exemplary embodiments as a single active agent, or in combination with additional methods of treatment including, but not limited to, irradiation therapy, therapy with immunosuppressive agents, chemotherapeutic or anti-proliferative agents, including cytokines. The methods of treatment of the invention may be in parallel to, prior to, or following additional methods of treatment.

Any of the vectors described herein are useful for the treatment of a neoplastic disease. When used pharmaceutically, the vectors of the invention can be combined with one or more pharmaceutically acceptable carriers. Pharmaceutically acceptable carriers are well known in the art and include aqueous solutions such as physiologically buffered saline or other solvents or vehicles such as glycols, glycerol, vegetable oils (e.g., olive oil) or injectable organic esters. A pharmaceutically acceptable carrier can be used to administer the compositions of the invention to a cell in vitro or to a subject in vivo.

A pharmaceutically acceptable carrier can contain a physiologically acceptable compound that acts, for example, to stabilize the composition or to increase the absorption of the agent. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. One skilled in the art would know that the choice of a pharmaceutically acceptable carrier, including a physiologically acceptable compound, depends, for example, on the route of administration of the polypeptide. For example, a physiologically acceptable compound such as aluminum monosterate or gelatin is particularly useful as a delaying agent, which prolongs the rate of absorption of a pharmaceutical composition administered to a subject. Further examples of carriers, stabilizers or adjutants can be found in Martin, Remington's Pharm. Sci., 15th Ed. (Mack Publ. Co., Easton, 1975), incorporated herein by reference.

As used herein, "pharmaceutical composition" or "composition" refers to any of the compositions of matter described herein. The compositions can then be administered therapeutically or prophylactically. They can be contacted with the host cell in vivo, ex vivo, or in vitro, in a therapeutically effective amount. In vitro and in vivo means of transfecting the vectors of the invention are provided below.

According to the invention, any suitable route of administration of the vectors may be adapted, including but not limited to, intravenous, oral, buccal, intranasal, inhalation, topical application to a mucosal membrane or injection, including intratumoral, intradermal, intrathecal, intracisternal, intralesional or any other type of injection. Administration can be effected continuously or intermittently and will vary with the subject and the condition to be treated.

An exemplary embodiment includes an oncolytic HSV, such as created by methods described herein, for example random mutagenesis, and further comprises a nucleic acid encoding an angiostatic polypeptide, such as Vasculostatin.

Nucleic Acid-Based Expression Systems

An exemplary embodiment is directed to an HSV vector. In specific embodiments, the vector comprises some or all of the following components.

The term "vector" is used to refers to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

Promoters and Enhancers

In exemplary embodiments, an HSV immediate early viral promoter is operably linked to the transgene in order to drive the expression of the heterologous transgene. More preferably, the early viral promoter utilized is the HSV immediate early viral promoter IE4/5 (SEQ ID NO:5).

Various embodiments employ a tumor specific promoter element to achieve tumor specific replication of the mutant oncolytic virus. In various embodiments, the tumor specific promoter comprises a nestin enhancer element (6454 bp-7082 bp of SEQ ID NO: 12). In an exemplary embodiment, the nestin enhancer element may be operably linked to a suitable promoter, for example, a heat shock protein 68 (hsp68) promoter (5576 bp-6412 bp of SEQ ID NO: 12). Various embodiments comprise a mutant HSV-1 vector in which a nestin enhancer element (6454 bp-7082 bp of SEQ ID NO: 12) drives expression of a replacement $\gamma_1 34.5$ gene, in an otherwise $\gamma_1 34.5$-deleted viral genome. In this manner, exemplary embodiments achieve increased tumor selectivity, particularly with respect to glioma cells. This promoter/enhancer arrangement was previously described by Kambara, et al. (See reference 15, below, incorporated by reference in its entirety).

The term "promoter" refers to a nucleic acid sequence that regulates, either directly or indirectly, the transcription of a corresponding nucleic acid coding sequence to which it is operably linked. The promoter may function alone to regulate transcription, or, in some cases, may act in concert with one or more other regulatory sequences such as an enhancer or silencer to regulate transcription of the transgene. The promoter comprises a DNA regulatory sequence, wherein the regulatory sequence is derived from a gene, which is capable of binding RNA polymerase and initiating transcription of a downstream (3'-direction) coding sequence.

A promoter generally comprises a sequence that functions to position the start site for RNA synthesis. The best-known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages may be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the .beta.-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

The nucleic acid molecules of the invention are not limited strictly to molecules including the sequences set forth as SEQ ID NO: 1, SEQ ID NO: 3, SEQ ID NO: 6, SEQ ID NO: 8. Rather, specific embodiments encompasses nucleic acid molecules carrying modifications such as substitutions, small deletions, insertions, or inversions, which nevertheless encode proteins having substantially the biochemical activity of the polypeptide according to the specific embodiments, and/or which can serve as hybridization probes for identifying a nucleic acid with one of the disclosed sequences. Included in the invention are nucleic acid molecules, the nucleotide sequence of which is at least 95% identical (e.g., at least 96%, 97%, 98%, or 99% identical) to the nucleotide sequence shown as SEQ ID NOS: 1, 3, 5, 6, 8, and 10-12 in the Sequence Listing.

The determination of percent identity or homology between two sequences is accomplished using the algorithm of Karlin and Altschul (1990) Proc. Nat'l Acad. Sci. USA 87: 2264-2268, modified as in Karlin and Altschul (1993) Proc. Nat'l Acad. Sci. USA 90:5873-5877. Such an algorithm is incorporated into the NBLAST and XBLAST programs of Altschul et al. (1990) J. Mol. Biol. 215:403-410. BLAST nucleotide searches are performed with the NBLAST program, score=100, wordlength=12 to obtain nucleotide sequences homologous to the nucleic acid molecules of the invention. BLAST protein searches are performed with the XBLAST program, score=50, wordlength=3 to obtain amino acid sequences homologous to the protein molecules of the invention. To obtain gapped alignments for comparison purposes, Gapped BLAST is utilized as described in Altschul et al. (1997) Nucleic Acids Res. 25: 3389-3402. When utilizing BLAST and Gapped BLAST programs, the default parameters of the respective programs (e.g., XBLAST and NBLAST) are used. See http://www.ncbi.nlm.nih.gov.

The term "stringent hybridization conditions" is known in the art from standard protocols (e.g., Current Protocols in Molecular Biology, editors F. Ausubel et al., John Wiley and Sons, Inc. 1994) and is to be understood as conditions as stringent as those defined by the following: hybridization to filter-bound DNA in 0.5 M $NaHPO_4$ (pH 7.2), 7% sodium dodecyl sulfate (SDS), 1 mM EDTA at +65.degree. C., and washing in 0.1.times.SSC/0.1% SDS at +68.degree. C.

Also included in the invention is a nucleic acid molecule that has a nucleotide sequence which is a degenerate variant of a nucleic acid disclosed herein, e.g., SEQ ID NOS: 1, 3, 6, and 8. A sequential grouping of three nucleotides, a "codon," encodes one amino acid. Since there are 64 possible codons, but only 20 natural amino acids, most amino acids are encoded by more than one codon. This natural "degeneracy" or "redundancy" of the genetic code is well known in the art. It will thus be appreciated that the nucleic acid sequences shown in the Sequence Listing provide only an example within a large but definite group of nucleic acid sequences that will encode the polypeptides as described above.

The invention also includes an isolated polypeptide encoded by a nucleic acid of the invention. An "isolated" polypeptide is a polypeptide that is substantially free from the proteins and other naturally occurring organic molecules with which it is naturally associated. Purity can be measured by any art-known method, e.g., column chromatography, polyacrylamide gel electrophoresis, or HPLC. An isolated polypeptide may be obtained, for example, by extraction from a natural source (e.g., a human cell); by expression of a recombinant nucleic acid encoding the polypeptide; or by chemical synthesis of the polypeptide. In the context of a polypeptide obtained by extraction from a natural source, "substantially free" means that the polypeptide constitutes at least 60% (e.g., at least 75%, 90%, or 99%) of the dry weight of the preparation. A protein that is chemically synthesized, or produced from a source different from the source from which the protein naturally originates, is by definition substantially free from its naturally associated components. Thus, an isolated polypeptide includes recombinant polypeptides synthesized, for example, in vivo, e.g., in the milk of transgenic animals, or in vitro, e.g., in a mammalian cell line, in *E. coli* or another single-celled microorganism, or in insect cells.

In various embodiments, the polypeptide of the invention include an amino acid sequence as set forth in SEQ ID NOS: 2, 4, 7 and 9. However, polypeptides of the exemplary embodiments are not to limited to those having an amino acid sequence identical to one of SEQ ID NOS: 2, 4, 7 and 9 in the Sequence Listing. Rather, the invention also encompasses conservative variants of the disclosed sequences. "Conservative variants" include substitutions within the following groups: glycine and alanine; valine, alanine, isoleucine, and leucine; aspartic acid and glutamic acid; asparagine, glutamine, serine, and threonine; lysine, arginine, and histidine; and phenylalanine and tyrosine.

Also included in the invention are polypeptides carrying modifications such as substitutions, small deletions, insertions, or inversions, which polypeptides nevertheless have substantially the biological activities of the Vasculostatin polypeptide. Consequently, included in the invention is a polypeptide, the amino acid sequence of which is at least 95% identical (e.g., at least 96%, 97%, 98%, or 99% identical) to an amino acid sequence set forth as SEQ ID NOS: 2, 4, 7 and 9 in the Sequence Listing. "Percent identity" is defined in accordance with the algorithm described above.

Also included in the invention are polypeptides of the invention that have been post-translationally modified, e.g., by cleavage of an N-terminal signal sequence, which can be, e.g., 1 to 25 amino acids long.

EXAMPLES

The following examples are included to demonstrate preferred embodiments of the invention. It should be appreciated by those skilled in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Oncolytic HSV

Recent developments in the use of gene therapy vectors have utilized viral and nonviral vectors to transduce cancer or stem cells [18-20]. Oncolytic viral treatment exploits tumor-specific conditional replication of viruses to lyse tumor cells [21-23]. Genetic modifications of viral proteins to infect tumor cells specifically has been exploited to enhance tumor-specific viral tropism [24]. Specific replication within tumor cells can be achieved by OVs genetically engineered for that purpose or by naturally occurring strains of some viruses that have such propensity [25]. In a preferred embodiment, an HSV-1 derived OV deleted for both copies of the γ34.5 gene and additionally disrupted for the ICP6/RR genes that expresses Vasculostatin under the control of an early viral promoter, IE4/5, was constructed.

Example 1

Vasculostatin is Anti-Tumorigenic

We have recently discovered Vasculostatin, a fragment of brain angiogenesis inhibitor 1 (BAI1), which inhibits angiogenesis, tumor growth, and vascular permeability. We have found that BAI1 is differentially expressed in normal and neoplastic brain. This is consistent with its reduced expression in pulmonary adenocarcinoma and pancreatic and gastric cancers, we and others have found it to be absent from brain tumors, but present in normal brain and benign gliomas. The protein's brain specific expression along with its absence in a majority of human GBM specimens implies that loss of BAI1 during tumor progression may give the tumors a growth advantage.

Previous work has demonstrated that BAI1 is processed at a conserved GPS site through proteolysis, and this processing leads to the secretion of the extracellular domain of the protein. The cleaved extracellular domain yields a 120-kDa secreted fragment called Vasculostatin.

To investigate if Vasculostatin could inhibit the growth of intracranial tumors, we compared the survival of rats implanted with U87 human glioma cells stably expressing Vasculostatin (clones U14 and U18) with parental untransfected glioma cells. Referring to FIG. 1, $1 \times 10^6$ cells, derived from parental U87MG and Vasculo-expressing clones U14 and U18 were implanted stereotactically in the brains of athymic nude rats as described. Animals were carefully monitored for signs of necropsy and were sacrificed according to our IACUC guidelines. Survival of rats implanted with cells expressing Vasculostatin was significantly greater than that of rats implanted with control parental U87MG cells (P<0.05).

Therefore, Vasculostatin is a novel and potent inhibitor of angiogenesis tumor growth and vascular permeability. However, because of the many variables involved with oncolytic viral expression, it was unknown whether or not it would make an effective therapeutic factor in the context of an oncolytic virus. Furthermore, it was unknown whether or not the presence of vasculostatin would interfere with the cytoxic ability of the virus.

Example 2

Creation of rHSVQvasculo

In order to produce an oncolytic virus expressing vasculostatin HSVQuick methodology was employed [1]. The HSVQuik methodology is a novel BAC-based method that utilizes two different site-specific recombination systems to introduce a transgene of interest into the deleted UL39 locus. The fHsvQuik-1 is the BAC DNA with the incorporation of the entire HSV-1 genome lacking a functional ICP6 gene and deleted in both copies of the γ34.5 gene incorporated in it. ICP34.5 allows the virus to replicate in non-dividing cells and dephosphorylates the cellular translation initiation factor (eIF-2α) that is phosphorylated in response to activation of double-stranded RNA activated protein kinase (PKR). These modifications allow the virus to replicate selectively in cancer cells. Additionally, fHsvQuik-1 has an insertion of a red fluorescent protein (RFP) in the middle of the BAC (bacterial artificial chromosome) backbone and thereby allows for efficient monitoring of the presence of BAC sequences in the vector genome.

Using this methodology, one OV embodiment was created and named rHSVQvasculo (also named "RAMBO," Rapid Anti-angiogenesis Mediated By Oncolysis virus). In that OV, a Vasculostatin transgene is driven by the viral immediate early IE4/5 promoter.

Figure 2:
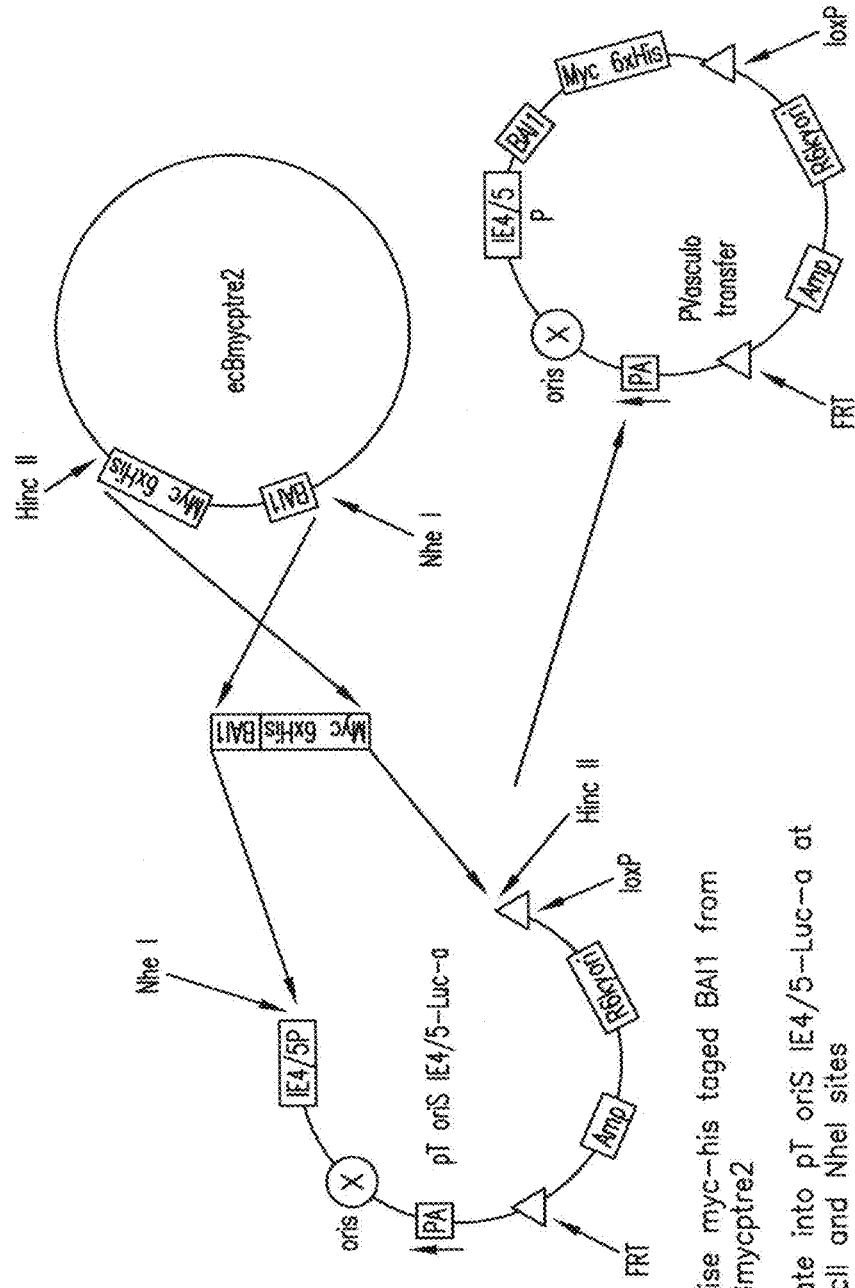
FIG. 2 provides a schematic illustration of the steps utilized to first clone the cDNA encoding for Vasculostatin under IE4/5 promoter into a shuttle plasmid (ptransferIE4/5) in order to generate pVasculo-transfer (SEQ ID NO: 10)

Referring to FIG. 2, to construct rHSVQvasculo, we used standard molecular biology approaches to first clone the cDNA encoding for Vasculostatin under IE4/5 promoter into a shuttle plasmid (ptransferIE4/5 which is published in Yamamoto et al, *Gene Therapy* 13, 1731-1736 (2006), incorporated herein by reference) to generate the pVasculo-transfer plasmid (SEQ ID NO: 10). The generated pVasculo-transfer plasmid is a replication-conditional plasmid (cannot replicate at 43° C.) in which the Vasculostatin gene is flanked by one loxP site and an FRT site. The early viral promoter IE4/5 was selected to drive Vasculostatin expression because it has an early and robust expression profile in the context of an oncolytic herpes simplex virus [1]. The generated plasmid was verified by restriction digest analysis and confirmed by sequencing (not shown).

Referring to FIG. 3, the Vasculostatin cassette along with the entire shuttle plasmid is inserted by Flp-mediated recombination into the disrupted ICP6 locus of the mutant HSV (Deleted for both copies of the γ34.5 gene) genome in the fHSVQuik-1 BAC DNA. To accomplish this pVasculo-transfer (ampicillin [Amp] resistant), along with fHSVQuik-1 (Chloramphenicol [Cm] resistant) and an Flp-expressing plasmid (pFTP-T) is electroporated into bacteria carrying fHSVQuik-1 DNA and grown at 43° C. The pCMVvasculotransfer and pFTP-T cannot replicate at this temperature, and 80% of the Cm- and Amp-resistant recombinants have the correct recombination to generate fHSVQ1-Vasculo. The harvested BACs are analyzed by PCR and restriction analysis for integration of pVasculo.

Again referring to FIG. 3, the selected recombinant fHSVQ1-Vasculo BAC is then transfected into Vero cells with a Cre-expressing helper plasmid. The Cre-mediated recombination results in the excision of the bacterial plasmid sequences flanked by LoxP sites. HSV recombinants generated by this process are easily identified because they express GFP, but not the RFP (excised by Cre-mediated recombination) in infected Vero cells. The isolated recombinants are purified through subsequent plaque purifications or serial dilutions, and confirmed by further southern blot analysis. The generated rHSVQvasculo from at least 2 isolates may be confirmed for correct insertion of IE4/5-Vasculostatin by Southern blot analysis. Briefly, viral DNA isolated from infected Vero cells was digested with XhoI, resolved by agarose gel electrophoresis, and transferred to nylon membranes. Probes specific for IE4/5-Vasculostatin were used to confirm its correct size and insertion [15]. The selected virus was confirmed for correct insertion and recombination events by sequencing both of the sites of recombination.

Example 3

Confirmation of Expression of Vasculostatin by the Recombinant Viral Isolates

Figure 4:
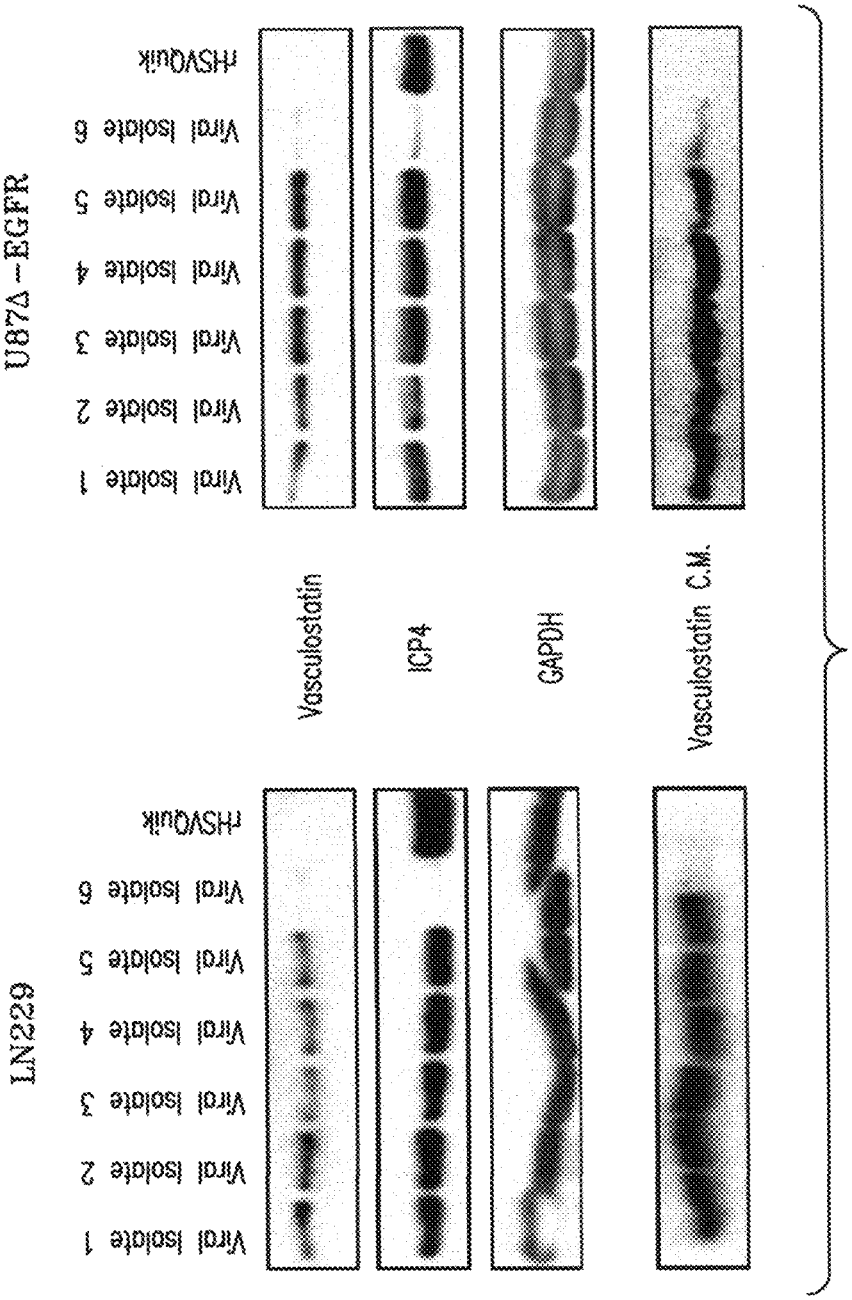
FIG. 4 shows a western blot analysis confirming the expression of Vasculostatin by the recombinant viral isolates.

Referring to FIG. 4, three viral isolates from each recombinant BAC ((fHSVQ1vasulo1, and fHSVQ1 vasulo2) were selected for further analysis. The resulting six viral isolates were used to infect two different glioma cell lines (LN229, and U87ΔEGFR) to evaluate Vasculostatin and viral ICP4 expression (FIG. 1). The indicated glioma cells were infected with the six viruses, 3 isolated from fHSVQ1vasculo1 (lanes 1-3) and with 3 isolated from fHSVQ1vasulo2 (lanes 4-6).

The infected cells and conditioned media were harvested 10 hours post infection and the cell lysate and TCA precipitated conditioned media was analyzed for Vasculostatin protein expression by western blot analysis. Note the presence of Vasculostatin in infected cell lysate and harvested conditioned media from infected cells but not in the control rHSVQ infected cells (bottom panel).

Example 4

Initial Characterization of Two Selected Viral Isolates

Figure 5:
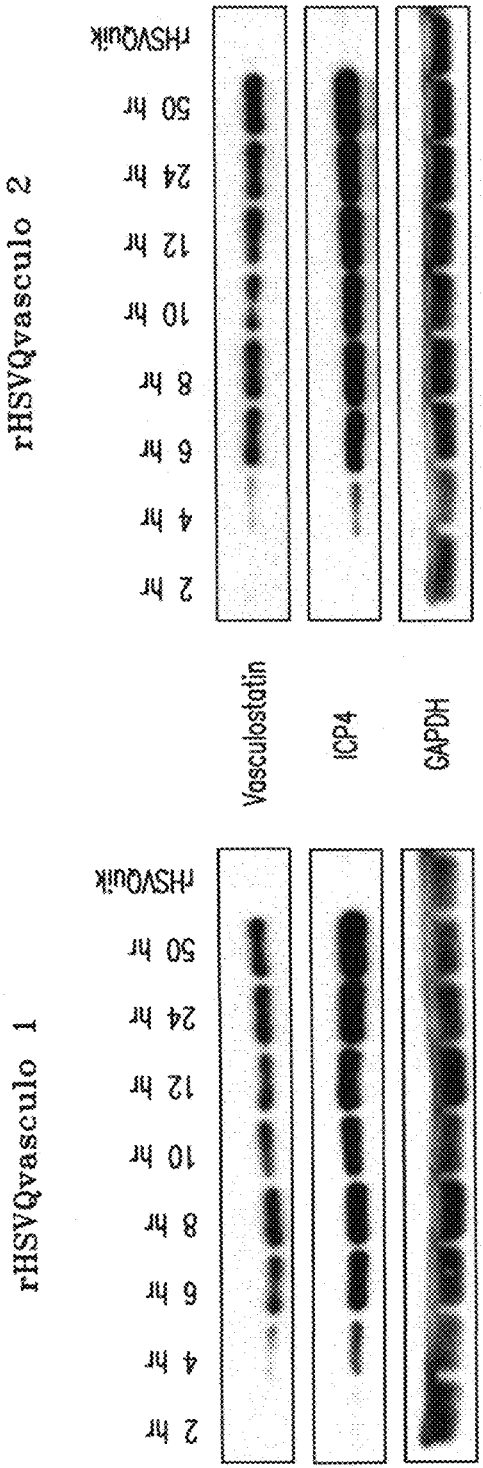
FIG. 5 shows a time course western analysis of Vasculostatin production by both OV isolates in LN229 cells

Referring to FIG. 5, from this initial screen we selected two viruses rHSVQvasculo 1 (lane 3), and rHSVQvasculo 2 (lane 5). We have purified both of these viruses. Since Vasculostatin expression in this recombinant virus is under the control of ICP4 promoter we checked the temporal pattern of expression of Vasculostatin and ICP4 in LN229 cells transfected with these viruses (FIG. 5). Briefly, LN229 glioma cells were transfected with the indicated viral isolate at an MOI of 0.1. Cells were harvested at the indicated times after infection and analyzed for expression of Vasculostatin and ICP4 by western blot analysis. Note the expression of both Vasculostatin and ICP4 come up as early as 4 hours after infection.

These results confirm that a recombinant oncolytic HSV which also expresses vasculostatin was generated.

Example 5

Figure 6:
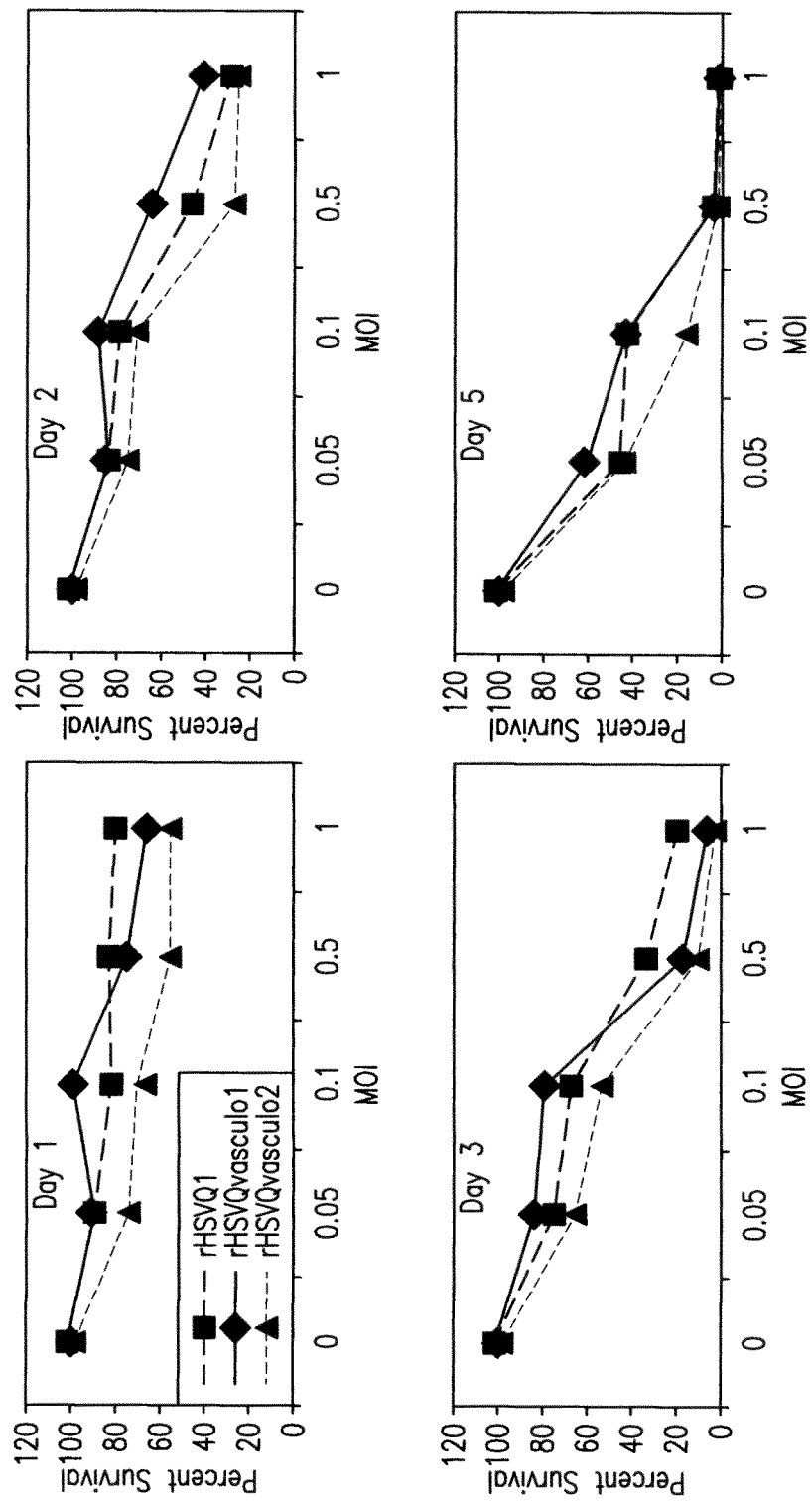
FIG. 6 shows a cytotoxicity assay for both viral isolates with U87ΔEGFR cells. Note that there is no significant difference in cytotoxicity between the control rHSVQ virus and the isolated rHSVQvasculo1, and rHSVQvasculo2 expressing Vasculostatin.

Vasculostatin does not Affect the Cytotoxicity of the Recombinant Oncolytic Virus Referring to FIG. 6, to compare the effect of Vasculostatin expression on oncolytic virus replication we compared the cytotoxicity of the control rHSVQ virus with the 2 selected viral isolates rHSVQvasculo1, and rHSVQvasculo2. Six thousand U87ΔEGFR glioma cells were infected with the indicated virus at MOI of 1, 0.5, 0.1, 0.01, and 0.05, on day zero. The number of viable cells was measured by a standard crystal violet assay on day 1, day, 2, day, 3 and day 5. Briefly, the cells at the indicated time point were fixed with 1% glutaraldehyde for 15 minutes and then stained with 5% crystal violet (dissolved in 4.75% ethanol) for 15 minutes. The plates were washed to remove unbound stain and the crystal violet crystals were dissolved in Sorensen's buffer prior to reading absorbance read at 590 nm. Note that there is no significant difference in cytotoxicity between the control rHSVQ virus and the isolated rHSVQvasculo1, and rHSVQvasculo2 expressing Vasculostatin.

Example 6

DIVAA Assay Confirms the In Vivo Anti-Angiogenic Capability of an Embodiment

Figure 7:
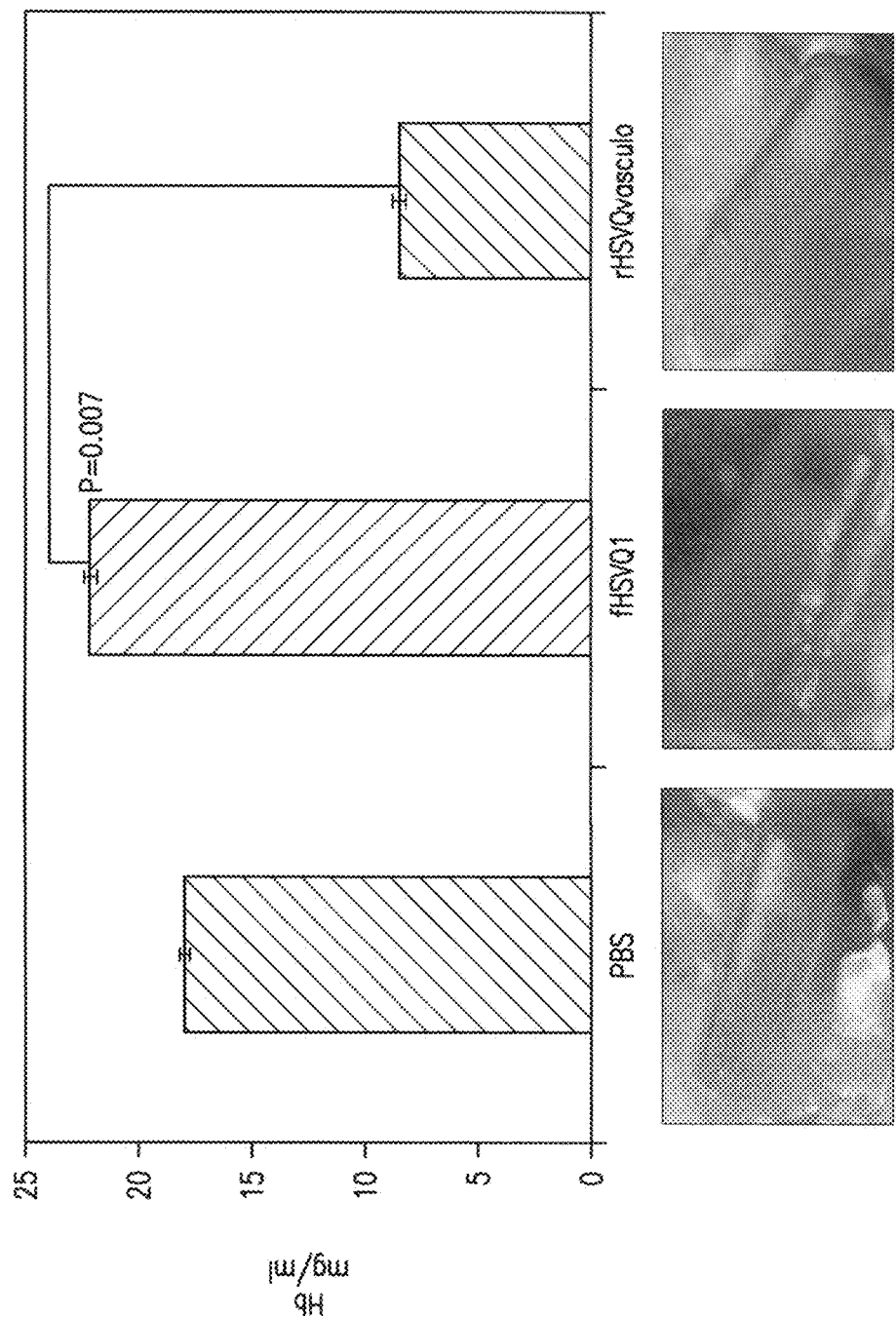
FIG. 7 demonstrates the anti-angiogenic capabilities of rHSVQvasculo. The experiment was performed using the Trevigen Direct In Vivo Angiogenesis Assay (DIVAA™) Inhibition Kit.

Referring to FIG. 7, the anti-angiogenic capabilities of rHSVQvasculo was tested using the Trevigen Direct In Vivo Angiogenesis Assay (DIVAA™) Inhibition Kit (Cat #: 3450-048-IK). Briefly, 2.5×105 U87ΔEGFR cells treated with PBS or infected with rHSVQ, rHSVQvasculo was mixed with basement membrane. The samples were then pipette into angioreactors and allowed to polymerize for 1 hour at 37° C. The tubes were then implanted into the rear flanks of nu/nu mice and 12 days later the mice were sacrifice and angioreactors removed. The amount of angiogenesis that occurred in the angioreactors was quantified using the Wako Hemoglobin B kit. Angiogenesis is initiated into the tubes from the one open end in the tubes. Note both visually and graphically the significant reduction in angiogenesis for samples infected with RAMBO compared to rHSVQ (n=10/group, and p=0.07) and PBS control (FIG. 6).

Example 7

The Oncolytic Virus rHSVQvasculo is Therapeutically Effective

We have tested the therapeutic potential of rHSVQvasculo in human glioma cells grown in a mouse brain tumor model. U87ΔEGFR human glioma cells were implanted intracranially in mice. Later, Mice were treated with direct intratumoral injection of rHSVQ or rHSVQvasculo. Animals were carefully monitored for any signs of morbidity and were sacrificed in accordance with our IACUC guidelines.

Figure 8:
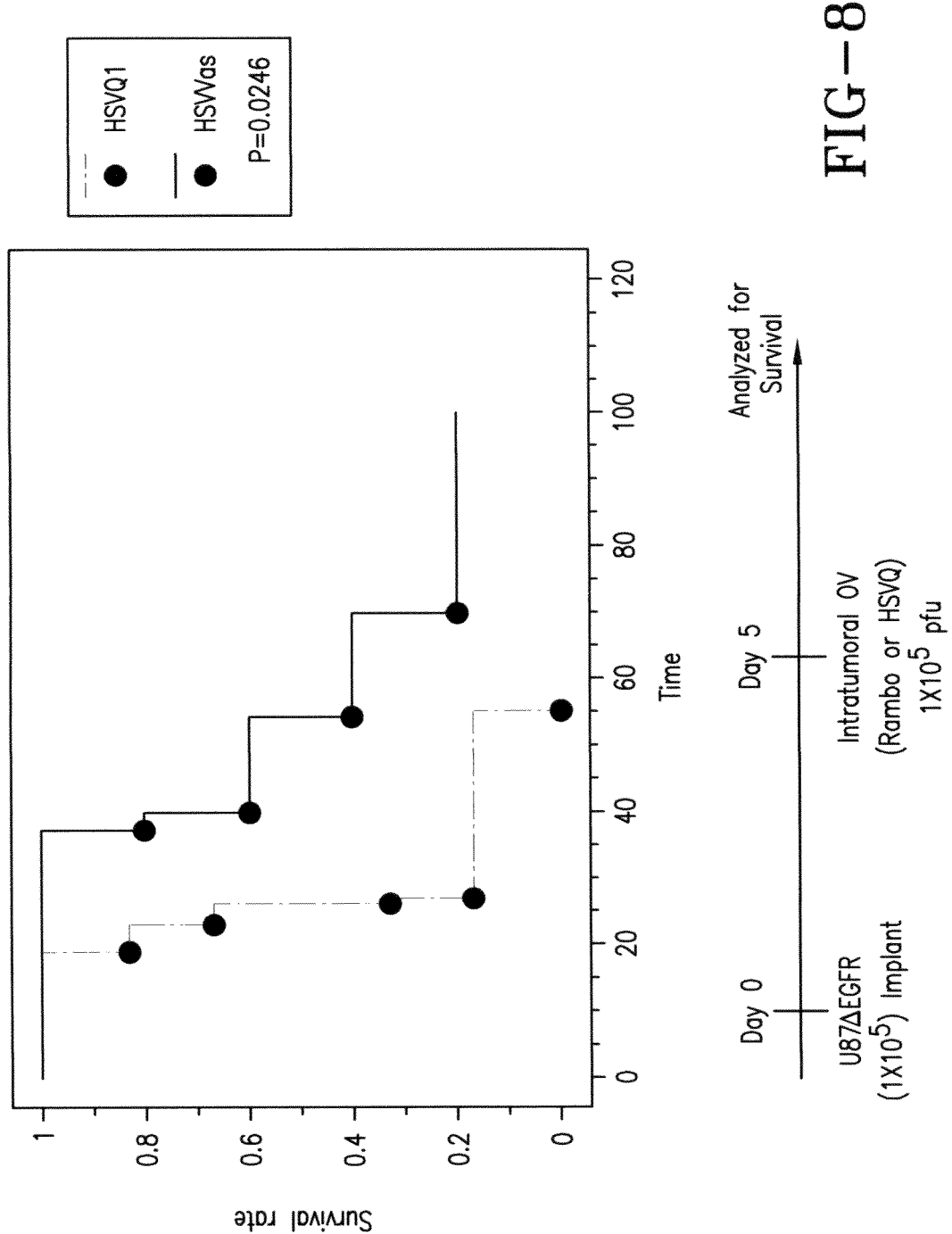
FIG. 8 shows a Kaplan-Meier survival analysis of mice treated with rHSVQ control virus or rHSVQvasculo (the virus generated to express Vasculostatin). In this experiment mice were treated by direct intratumoral injection on day 5 after tumor implantation.

FIG. 8 shows a Kaplan-Meier survival analysis of mice treated with rHSVQ control virus or rHSVQvasculo (the virus generated to express Vasculostatin). Briefly, Mice with intracranial tumors (U87ΔEGFR) were treated with a single dosage (1×10$^5$ pfu) of the control rHSVQ or the rHSVQvasculo at day 5 after tumor implantation. As can be observed from the figure, all of the rHSVQ mice died of tumor burden by day 55. However, there were 20% survivors in rHSVQvasculo treated animals. Survival of mice treated with rHSVQvasculo was significantly greater than that of mice treated with the rHSVQ virus (P=0.0246). Hence, rHSVQvasculo has potent anti-tumor efficacy compared to the parent control oncolytic virus.

Example 8

Comparison of rHSVQvasculo and rHSVQ Mediated Cytotoxicity to Normal Human Astrocytes (NHA)

Figure 9:
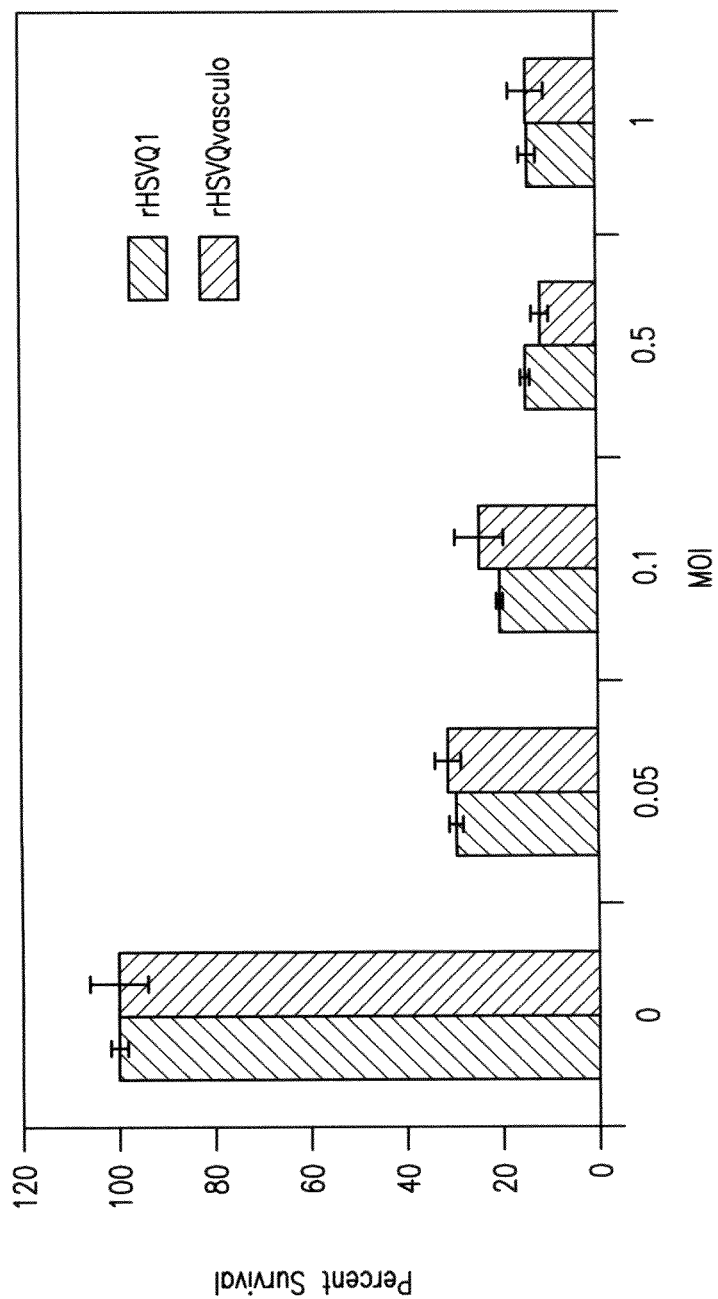
FIG. 9 shows the results of an experiment to compare the cytotoxicity of rHSVQvasculo to rHSVQ (an OV equivalent to the G207 being tested in clinical trials) toward normal human astrocytes. Normal human astrocytes (NHA, CellSciences Canton, Mass.) were infected at different multiplicities of infection (MOI) with rHSVQ and rHSVQvasculo to evaluate potential cytotoxicity of OV produced Vasculostatin towards NHA.

Referring to FIG. 9, to evaluate the cytotoxicity of rHSVQvasculo produced by the recombinant OV, we infected normal human astrocytes (NHA, CellSciences Canton, Mass.) at different multiplicities of infection (MOI) with rHSVQ and rHSVQvasculo to evaluate potential cytotoxicity of OV produced Vasculostatin towards NHA. Briefly NHA: cells were plated into 96 well plates (10,000 cells/well). The cells were infected with the indicated virus at MOI of 1, 0.5, 0.1, 0.01, and 0.05. Forty-eight hours post infection the number of viable cells measured by a standard Colorimetric crystal violet assay. Note no significant difference in the cytotoxicity to NHA at any of the indicated multiplicity of infection between rHSVQVasculo and rHSVQ. This indicated that rHSVQvasculo was as cytotoxic to NHA cells as rHSVQ.

Example 9

Viral Replication of rHSVQvasculo is Similar to rHSVQ Control Virus

Referring to Table 1 below, glioma cell lines: LN229, and U87ΔEGFR were infected with rHSVQ and rHSVQvasculo at an MOI 0.05. Seventy-two hours post infection the cells and supernatants were harvested and the number of infectious viral particles (pfu) in each cell line was assessed by a standard viral titration assay. Table 1 below shows the results of viral titration in each indicated cell line. Note: The results indicate no significant difference in the replication ability of rHSVQvasculo compared to rHSVQ.

TABLE 1

| LN229 | | U87ΔEGFR | |
|---|---|---|---|
| rHSVQ | rHSVQvasculo | rHSVQ | rHSVQvasculo |
| 7500 pfu/mL | 8125 pfu/mL | 56250 pfu/mL | 31250 pfu/mL |

Example 10

Figure 10A:
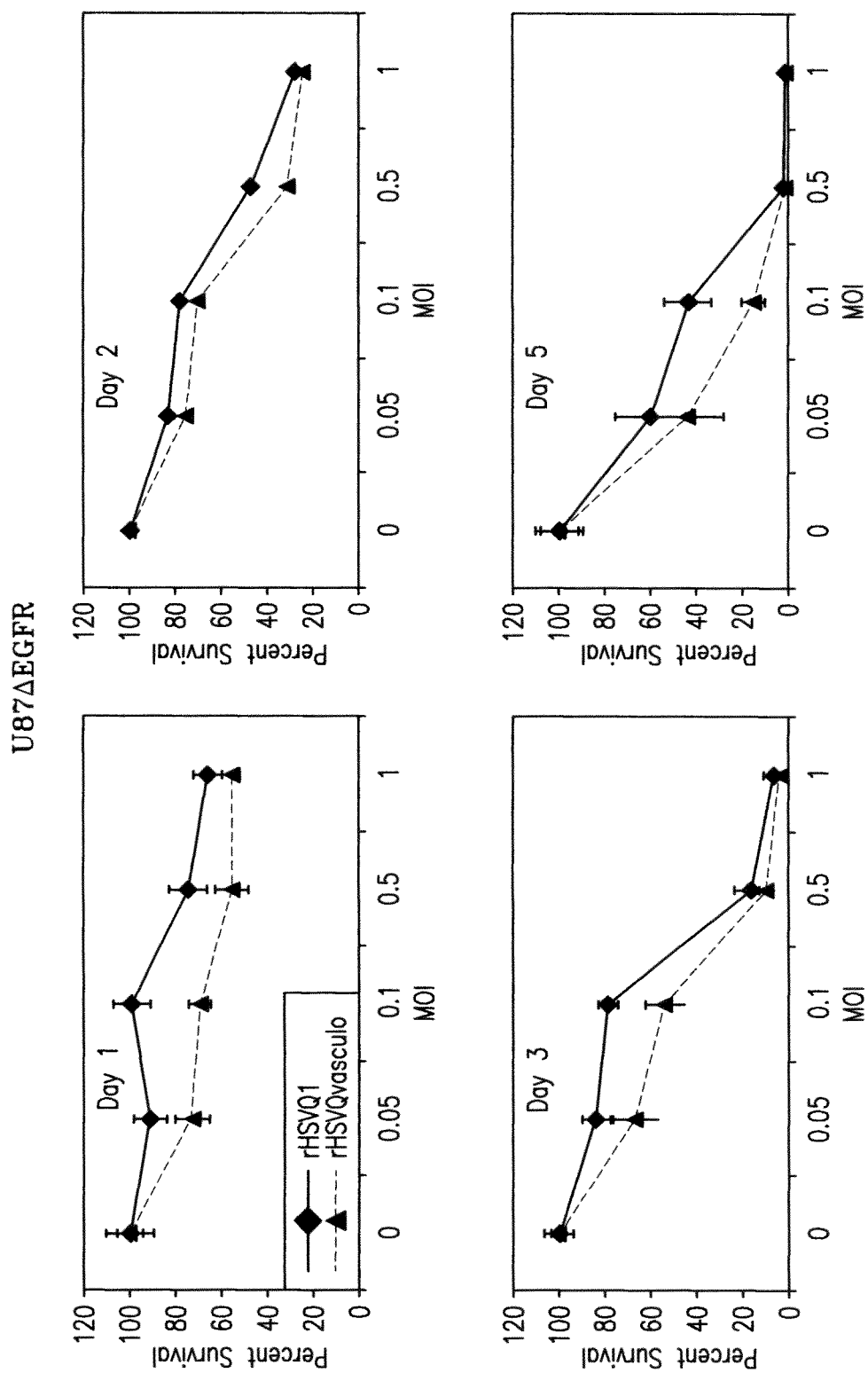
FIG. 10 shows a comparison of the effect of Vasculostatin expression on ability of OV to be cytotoxic to glioma cells in the glioma cells LN229, U87ΔEGFR, and U343, using a standard colorimetric assay. Note that there are no significant differences in the cytotoxicity for the two viruses.
Figure 10B:
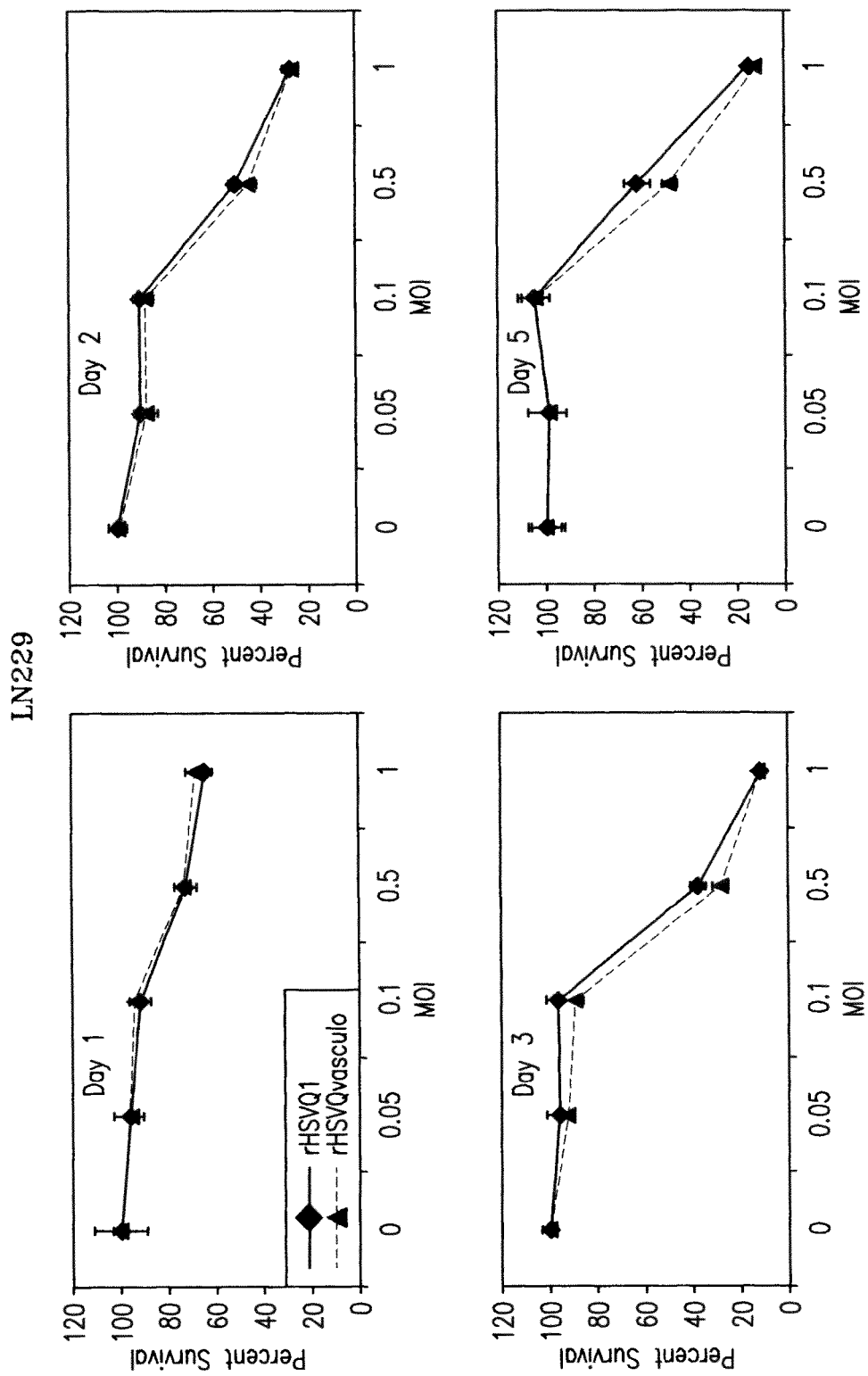
Figure 10C:
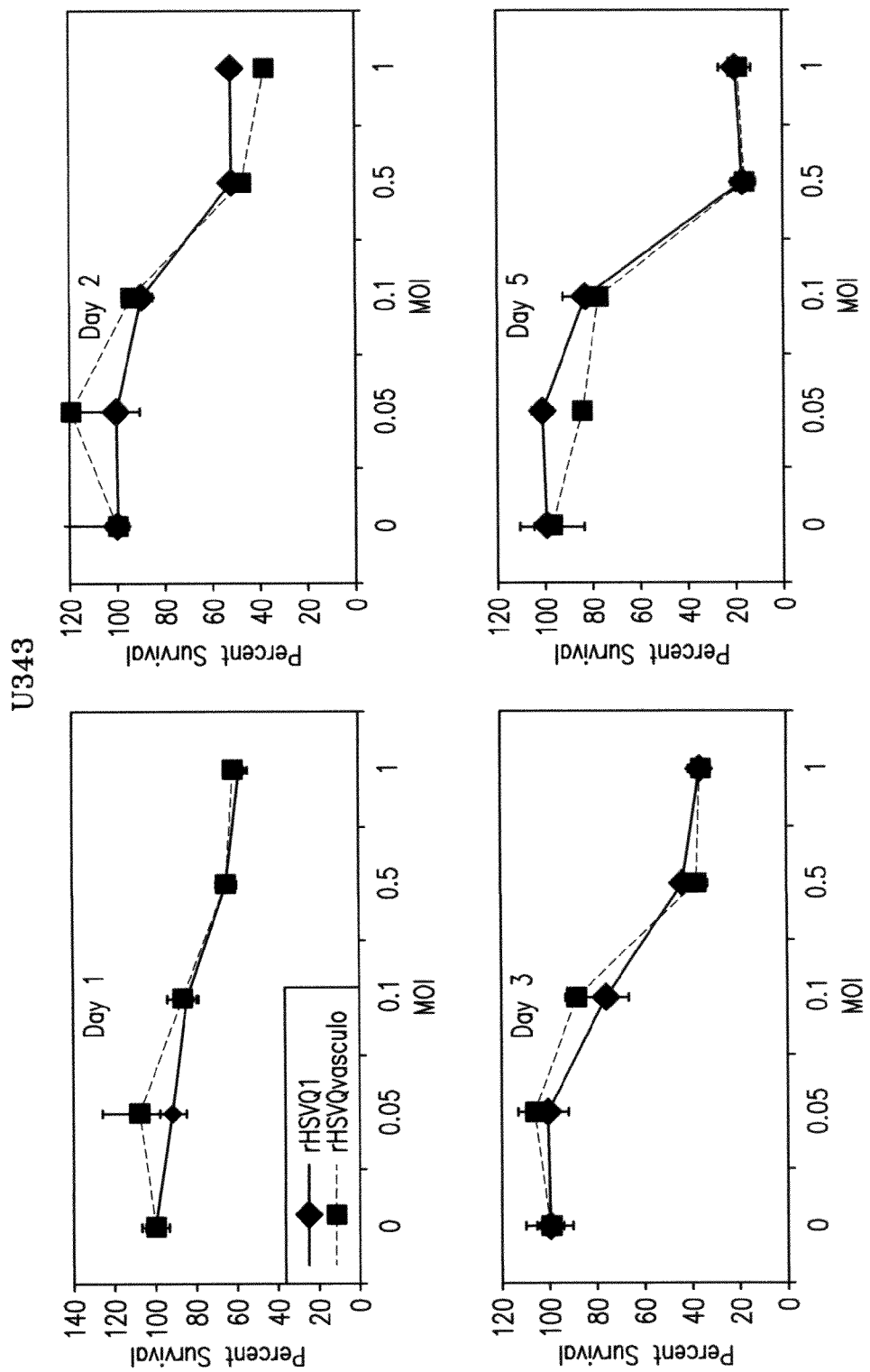

Cellular Cytotoxicity Results in Multiple Glioma Cell Lines Demonstrating the Ability of the rHSVQvasculo to be Cytotoxic to Multiple Glioma Cells In Vitro Referring to FIG. 10, the effect of Vasculostatin expression on ability of OV to be cytotoxic to glioma cells was compared in the glioma cells LN229, U87ΔEGFR, and U343, using a standard colorimetric assay. All cell lines were infected with control rHSVQ virus or rHSVQvasculo at indicated MOIs (1, 0.5, 0.1, 0.01, or 0.05). The number of viable cells was measured by a standard Colorimetric crystal violet assay on day 1, day, 2, day, 3 and day 5. Note that there are no significant differences in the cytotoxicity for the two viruses.

Example 11

Figure 11:
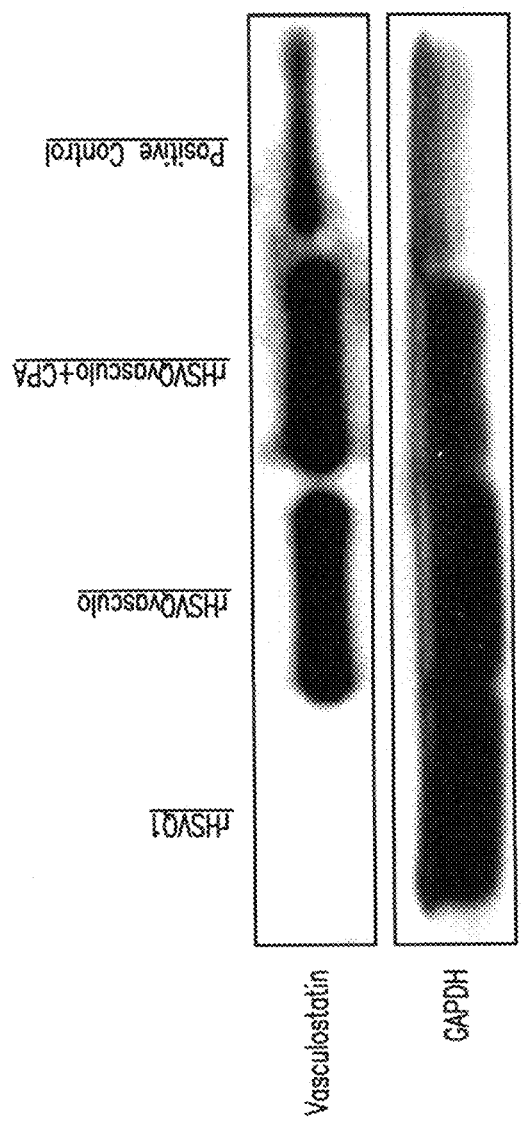
FIG. 11 is a Western blot demonstrating that cyclophosphamide (CPA) pretreatment enhances the anti-tumor ability of Vasculostatin.

Cyclophosphamide (CPA) Pretreatment Further Enhances the Anti-Tumor Ability of Vasculostatin Referring to FIG. 11, Athymic nude mice were injected with $2.5 \times 10^6$ U87ΔEGFR cells. Seventeen days later, when the tumors were of sufficient size (>750 mm$^3$), the mice were treated with PBS or CPA (200 mg/kg) by intraperitoneal injection. Two days after CPA/PBS treatment the animals were anesthetized and tumors were injected with $1 \times 10^6$ pfu rHSVQvasculo, or control rHSVQ. Animals were sacrificed 48 hrs after OV treatment and the tumors were explanted sectioned into small pieces, and snap frozen. The tumors were lysed and equal amounts of lysate was then assayed for the presence of Vasculostatin by western blot analysis. Western blot analysis for expression of Vasculostatin in subcutaneous tumors (U87ΔEGFR glioma) injected with rHSVQvasculo or control rHSVQ OV. Positive control is cell lysate from LN229 cells infected with rHSVQvasculo, (MOI 0.05) for 48 hours. Note the presence of vasculostatin in the rHSVQvasculo treated tumors indicating the ability of rHSVQvasculo to express Vasculostatin in vivo. Note also the increase in Vasculostatin expression in the CPA treated animals.

Example 12

Creation of "Nested" RAMBO Vector

The HSVQuik methodology was employed to engineer a Nested-RAMBO Oncolytic virus. See Edyta Tyminski, et al; Brain Tumor Oncolysis with Replication-Conditional Herpes Simplex Virus Type 1 Expressing the Prodrug-Activating Genes, CYP2B1 and Secreted Human Intestinal Carboxylesterase, in Combination with Cyclophosphamide and Irinotecan; Cancer Res 2005 Aug. 1; 65(15):6850-6857, (this reference incorporated by reference in its entirety). HSVQuik methodology is a BAC-based method which utilizes two different site specific recombination systems to introduce a transgene of interest into the deleted UL39 locus. The fHsvQuik-1 is lacking a functional ICP6 gene and is deleted in both the copies of the γ34.5 gene. Additionally fHsvQuik-1 has an insertion of RFP in frame and downstream of a truncated ICP6 coding sequence resulting in the loss of ICP6 (large subunit of viral ribonucleotide reductase) viral protein and an RFP (red fluorescent protein) in the middle of the BAC backbone to monitor the presence of BAC sequences in the vector genome.

The pTnestin34.5 plasmid (SEQ ID NO: 11) containing the nestin enhancer driven ICP34.5 (RL1 gene) in it was used as a starting material. Initially, a fragment (BstBI and XbaI) corresponding to Vasculostatin under the control of HSV-1 IE4/5 derived from pVasculo transfer plasmid (2276 bp-6641 bp of SEQ ID NO: 10) was inserted into the BstB1 and XbaI site of pT nestin34.5 plasmid (SEQ ID NO: 11). This step allowed for most of the Vasculostatin gene and HSV-1 IE4/5 promoter sequence to be inserted into the pTnestin 34.5 plasmid. Subsequently, a PCR fragment comprising of C-terminal region of Vasculostatin tagged with myc-His and a polyA site was inserted into XbaI site, resulting in complete Vasculostatin cDNA formed in the plasmid PNested-RAMBO-BGH. The primers were designed to recreate the disrupted FRT site. The Vasculostain and ICP34.5 expressing cassette along with the entire shuttle plasmid is inserted by Flp mediated recombination, into the fHSVQuik-1 BAC plasmid into the disrupted ICP6 locus of the mutant HSV (deleted for both copies of γ34.5 gene) genome in the BAC. pNested-RAMBO- BGH (ampicillin (Amp) resistant), along with fHSVQuik-1 (Chloramphenicol (Cm) resistant) and a Flp-expressing plasmid (pFTP-T) is electroporated into bacteria carrying fHS-VQuik-1 DNA and grown at 43° C. The pNested-RAMBO-BGH, and pFTP-T can not replicate at this temperature and 80% of the Cm and Amp resistant recombinants have the correct recombination to generate fHSVQ1-vasculo. The harvested BACs were analyzed by PCR, and restriction analysis for integration of PNested-RAMBO-BGH.

The selected recombinant fHSVQ1-Nested-RAMBO was transfected into Vero cells with a Cre expressing helper plasmid. The Cre mediated recombination results in the excision of the bacterial plasmid sequences flanked by LoxP sites. HSV Recombinants generated by this process are easily identified as they express EGFP but not the RFP (excised by Cre-mediated recombination) in infected Vero cells. The isolated recombinants are purified through subsequent plaque purifications or serial dilutions.

Figure 12:
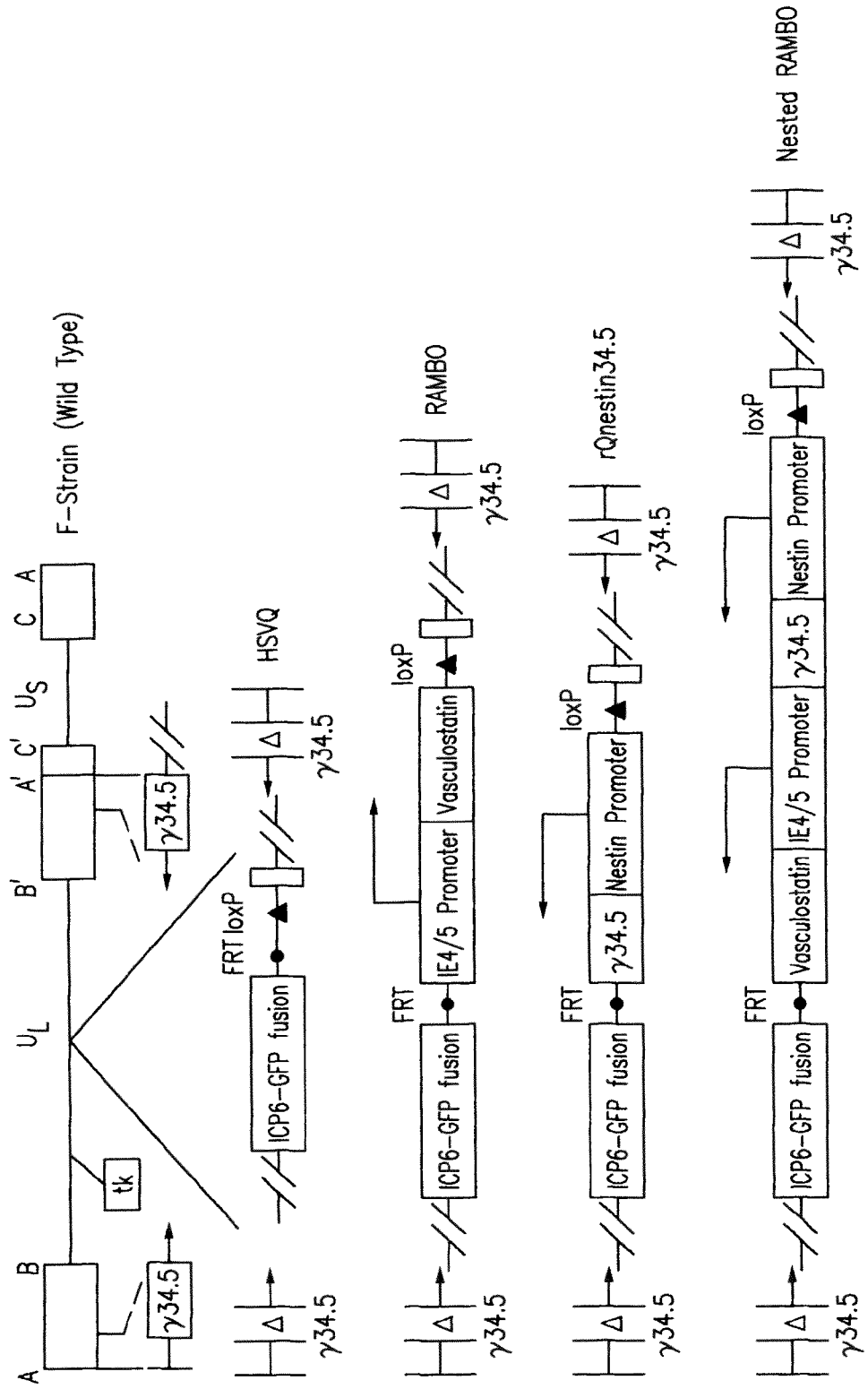
FIG. 12 is a schematic representation of the maps of various oncolytic virus embodiments, included Nested-RAMBO. Nested-RAMBO is a Vasculostatin expressing virus within the rQnestin34.5 virus backbone.

The final insertion in the virus corresponds to the sequences 9278-7344 of the plasmid p-Nested RAMBO BGH (9278-7344 of SEQ ID No. 12). A map of the Nested RAMBO virus is provided in FIG. 12.

Example 13

Expression of Vstat120 and Suppression of eIF2α Phosphorylation

Figure 13:
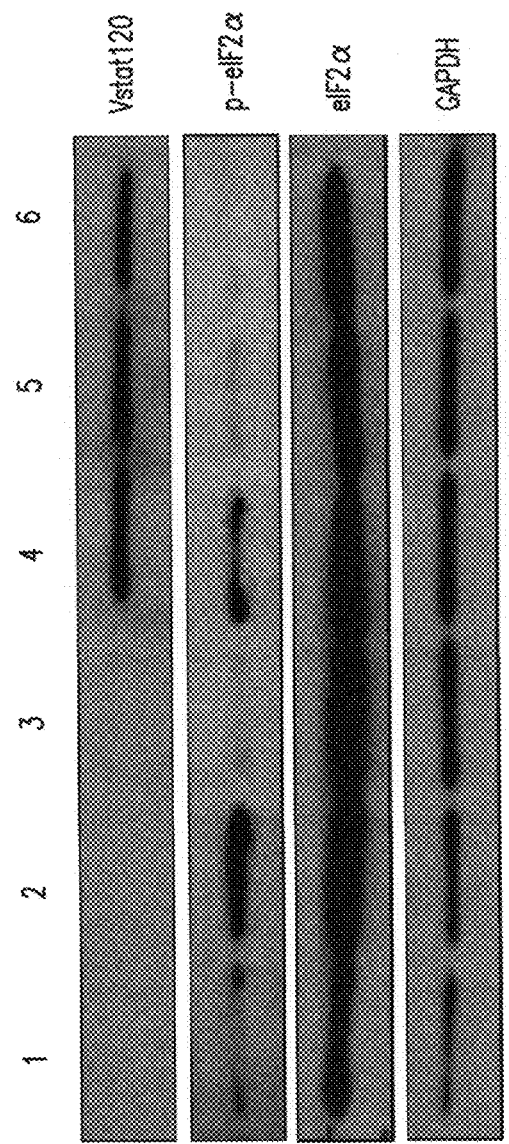
FIG. 13 is a Western blot of U251 glioma cells treated with PBS (lane 1), HSVQ (Lane 2), rQnestin34.5 (lane 3), RAMBO (lane 4), or 2 different isolates of Nested-Rambo (lanes 5 and 6) showing expression of Vstat120, eIF2α, and phospho-eIF2α in cell lysate 14 hrs after OV infection.

Having engineered Nested-RAMBO, an OV expressing Vstat120 in the backbone of rQnestin34.5 (FIG. 12), the correct insertion of Vstat120 was confirmed by restriction digest and PCR (not shown). The ability of this virus to express Vstat120 and to suppress eIF2α phosphorylation was tested in U251 glioma cells following infection (FIG. 13). U251 glioma cells express high levels of nestin and so permit efficient expression of ICP34.5 from its nestin promoter from rQnestin34.5 and Nested-RAMBO. Note the production of Vstat120 in cells infected with RAMBO (lane 4) and two different isolates of Nested-RAMBO (lane 5 and 6). Note also increased phosphorylation of eIF2α in HSVQ and RAMBO infected cells (Lanes 2 and 4) but not in rQnestin34.5 and Nested-RAMBO cells (Lanes 3, 5, and 6). This indicates that Nested RAMBO has both ICP34.5 and Vstat120 expression in glioma cells expressing high levels of nestin. The expression of Vstat120 (ICP4 driven) in Qnestin negative cells was also confirmed (data not shown).

Example 14

Specificity of Nested-RAMBO

Figure 14:
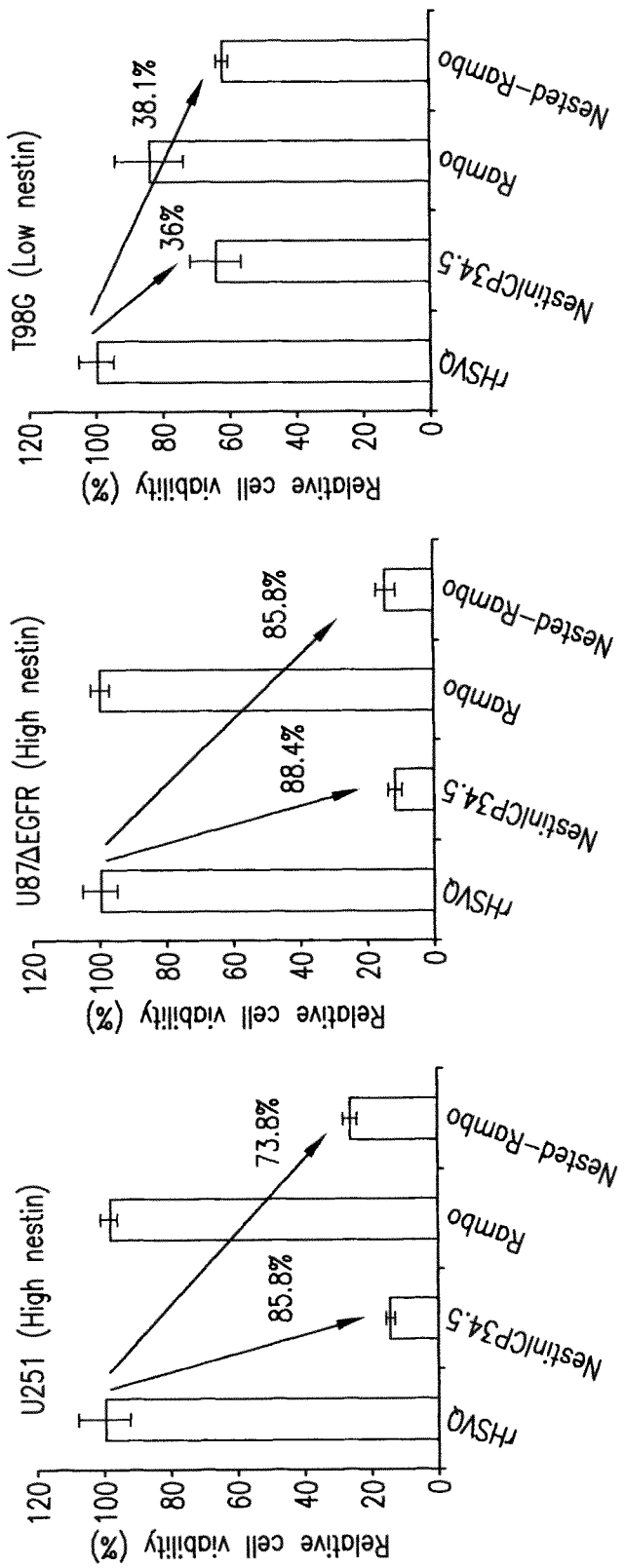
FIG. 14 is a graph of the results from an experiment comparing the cytolytic ability of Nested-RAMBO, to rQnestin34.5 in glioma cells with high and low nestin expression.

With reference to FIG. 14, to test the specificity of nestin enhancer element driven ICP34.5 in Nested-RAMBO, the cytolytic ability of Nested-RAMBO, to rQnestin34.5 in glioma cells with high and low nestin expression was compared. U251 and U87ΔEGFR cells express high levels of nestin, and T98G cells express low levels of nestin (8). Percent of cell survival relative to HSVQ cells was measured in these cells by a standard crystal violet assay.

The indicated cells were infected with the indicated virus (MOI=0.1) and the relative cell killing was measured. Briefly, the indicated glioma cells were seeded on 96-well plates. The following day, cells were infected with HSVQ, rQnestin 34.5, Rambo, or Nested-Rambo. After 2 days of incubation, cells were stained with crystal violet and the percentage of viable cells relative to HSVQ infected cells was measured at $A_{560}$ nm. The level of endogenous nestin expression in each cell is indicated in brackets. FIG. 14 shows the % cell survival relative to HSVQ infected cells. Both rQnestin34.5 and Nested-RAMBO showed increased levels of cell killing relative to HSVQ infected cells in both U251 and U87ΔEGFR cells (74%-86%). In contrast, in T98G cells which express much lower levels of nestin (8) the difference between HSVQ and rQnestin34.5/Nested-RAMBO mediated cell killing was reduced to about 36-38%. This indicated that transcriptional control of ICP34.5 by the nestin enhancer element in Nested-RAMBO was similar to that in rQnestin34.5 in vitro (FIG. 14). There was no significant difference between HSVQ and RAMBO mediated glioma cell killing in vitro in any of the cell lines.

Example 15

Figure 15:
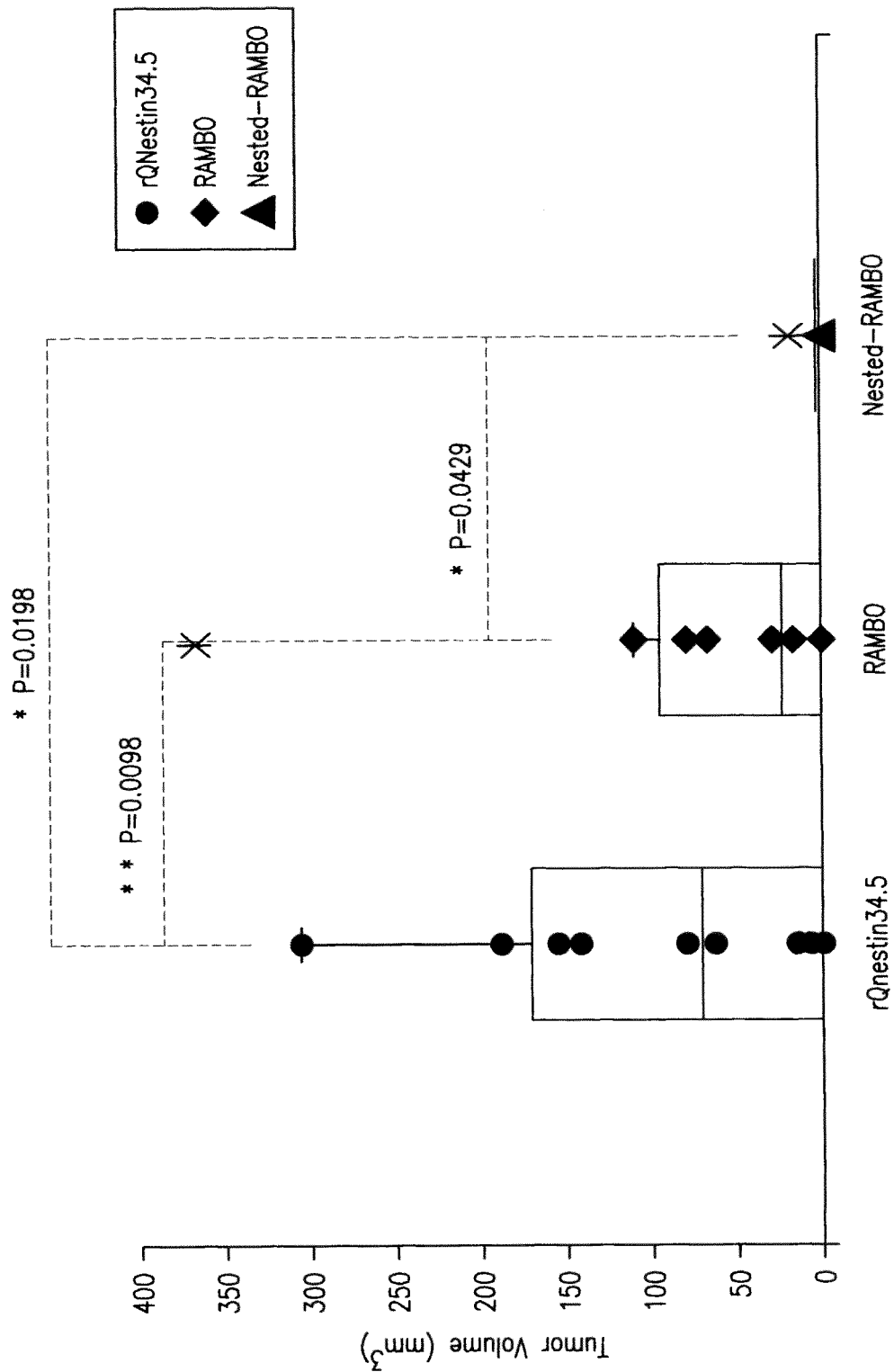
FIG. 15 is a graph detailing the results from an experiment comparing the antitumor efficacy of rQnestin34.5, RAMBO, and Nested-RAMBO against subcutaneous glioma in athymic nude mice.

Dramatically Improved Antitumor Efficacy of Nested RAMBO, Compared to rQnestin34.5 and RAMBO Against Subcutaneous Glioma In Vivo Referring to FIG. 15, U251T3 tumor bearing mice were treated with the indicated virus or PBS (not shown) once the tumors reached an average size of 200 mm³. The mice were treated by direct intratumoral injection of $1 \times 10^5$ pfu of virus on days 0, 2, 4, 6, 8, and 10. Tumor volume was measured over a period of time. The tumor volume of individual mice in each group on day 21 after initiation of treatment is shown. PBS treated mice had to be all sacrificed by day 21 due to tumor burden in accordance with our IACUC protocol (not shown). Not the significant reduction in tumor volume in mice treated with Nested-RAMBO compared to rQnestin34.5 and RAMBO treated mice.

Example 16

Creation of OV Expressing Chase ABC

The HSVQuik methodology was also used to engineer OV-Chase oncolytic virus (Tyminski, et al. 2005).

Step 1: Generation of Chase transfer plasmid: The cDNA encoding for Chase ABC was PCR amplified from DNA prepared from *P. Vulgaris* cells (ATCC). The resulting DNA was cloned into psecTAG/FRT/V5 plasmid (Invitrogen), which incorporated cDNA encoding for a secretion signal at the 5' terminus of Chase ABC cDNA. This was then subcloned into a shuttle plasmid under the control of viral IE4/5 promoter to generate pChase-transfer. The generated pChase-transfer plasmid is a replication-conditional plasmid (cannot replicate at 43° C.) in which the Chase ABC gene (from *P. vulgaris*) under the control of IE4/5 promoter is flanked by one loxP site and an FRT site. The generated plasmid was verified by restriction digest analysis and confirmed by sequencing (not shown).

Step 2: Generation of the recombinant BAC fChase: Next, the Chase ABC expression cassette along with the entire shuttle plasmid is inserted by Flp-mediated recombination into the disrupted ICP6 locus of the mutant HSVQ (Deleted for both copies of the γ34.5 gene) genome in the fHSVQuik-1 BAC DNA. To accomplish this pChase-transfer (ampicillin [Amp] resistant), along with fHSVQuik-1 (Chloramphenicol [Cm] resistant) and an Flp-expressing plasmid (pFTP-T) is electroporated into bacteria carrying fHSVQuik-1 DNA and grown at 43° C. The Chasetransfer plasmid and pFTP-T cannot replicate at this temperature, and 80% of the Cm- and Amp-resistant recombinants have the correct recombination to generate Bac fChase. The harvested BACs are analyzed by PCR and restriction analysis for integration of Chase-transfer plasmid. The resulting Bac DNA was confirmed by restriction digest and PCR to confirm correct insertion of the transgene plasmid.

Step 3: Generation of OV-Chase: The selected recombinant Bac fChase is then transfected into Vero cells with a Cre-expressing helper plasmid. The Cre-mediated recombination results in the excision of the bacterial plasmid sequences flanked by LoxP sites. HSV recombinants generated by this process are easily identified because they express GFP, but not the RFP (excised by Cre-mediated recombination) in infected Vero cells. The isolated recombinants are purified through subsequent plaque purifications or serial dilutions, and confirmed by further southern blot analysis. The generated ChaseQ from at least 2 isolates has been confirmed for correct insertion of Chase ABC by PCR analysis.

Example 17

Confirmation of Active Chase ABC Provided by OV-Chase

Figure 16:
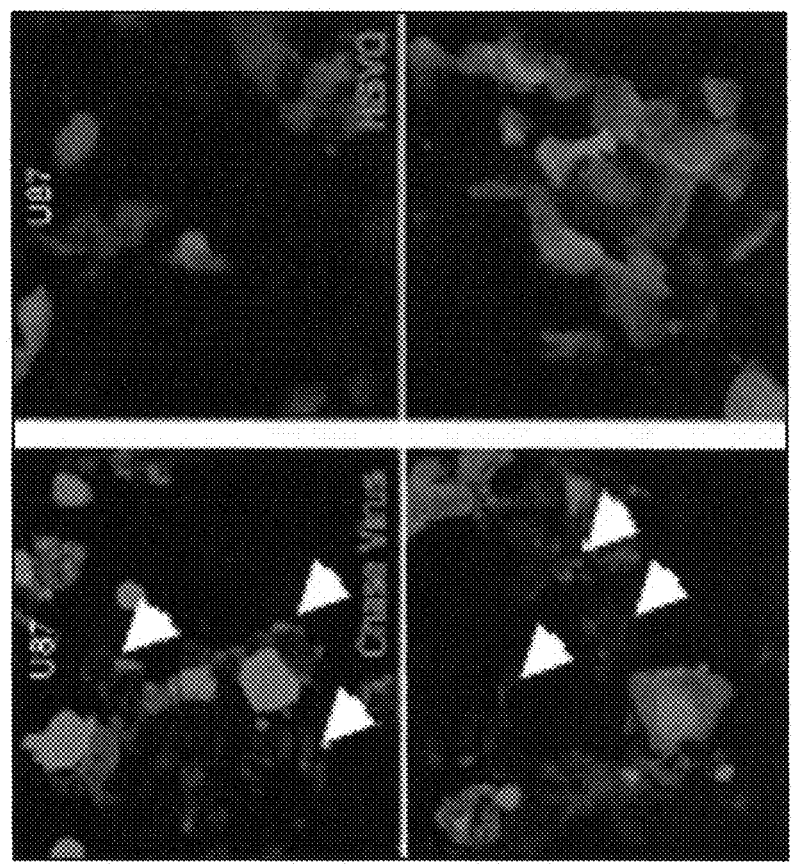
FIG. 16 shows representative fluorescent images of glioma spheres infected with HSVQ (right panel) or OV-Chase (left panel). Human glioma spheres infected with HSVQ or OV-Chase (green cells are GFP positive infected cells) were stained for the appearance of immunoreactive sugar stubs (red staining, white arrows) obtained by Chase ABC mediated digestion of cell secreted CSPG.

To confirm functionality of the secreted Chase ABC produced by OV-Chase we tested for the appearance of immunoreactive stubs in cells treated with OV-Chase compared to cells infected with HSVQ. FIG. 16 shows representative fluorescent images of glioma spheres infected with HSVQ (control OV) or Chase HSVQ. Human glioma spheres, were infected with HSVQ or OV-Chase and were stained for the appearance of immunoreactive sugar stubs (red staining, white arrows) obtained by Chase mediated digestion of CSPG. Infected cells are made obvious by the presence of virally encoded GFP. Note the presence of red staining sugar stubs (arrows) in Chase-HSVQ infected glioma cells around infected green cells, indicating functionality of ChaseABC produced OV-Chase.

Example 18

Figure 17:
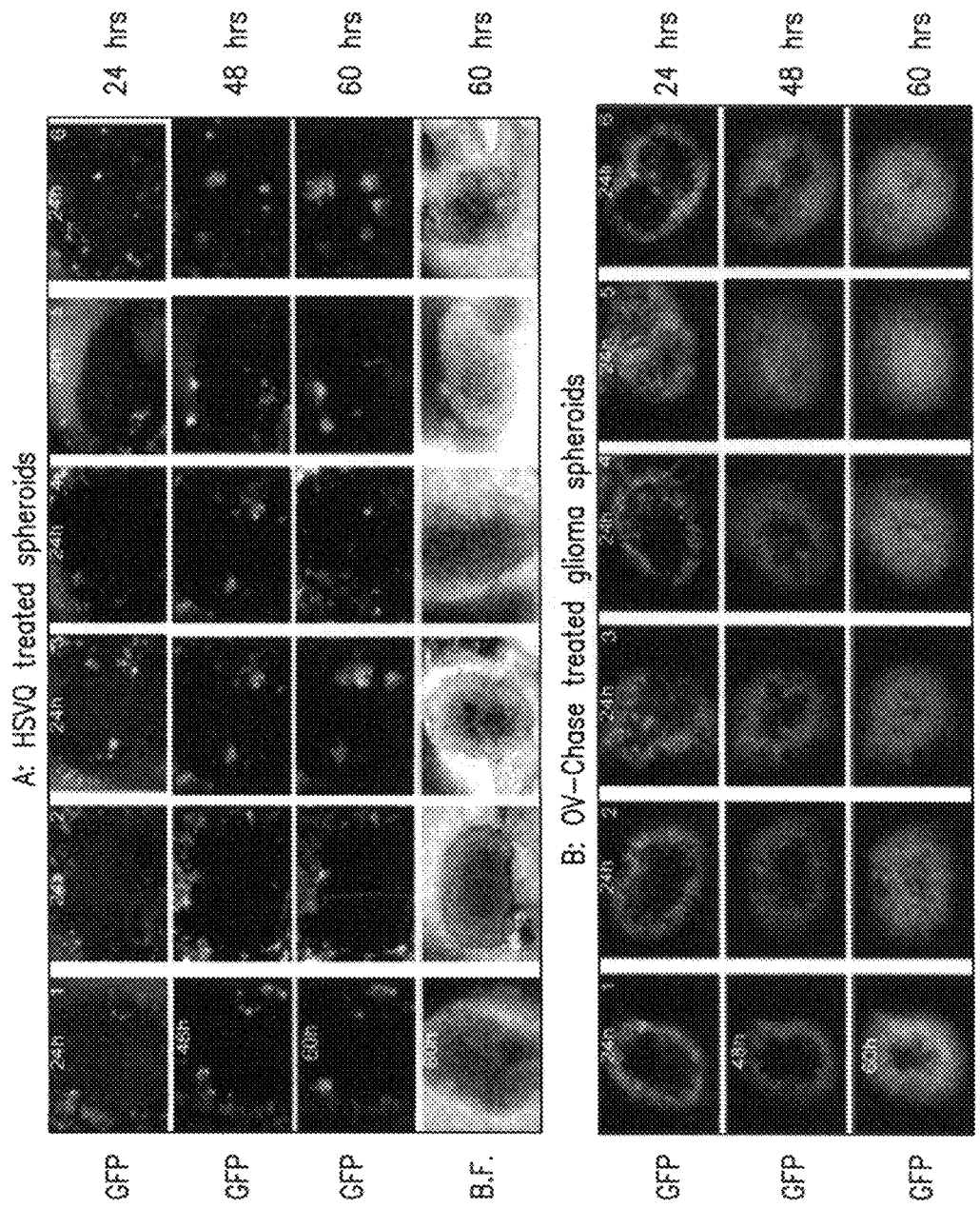
FIG. 17 shows fluorescent images of glioma spheroids infected with HSVQ or OV-Chase (n=6/group). Human glioma spheres grown on mouse brain slices, were infected with HSVQ (A) or OV-Chase (B) (n=6/group), and followed over a period of time (24 hrs: top row, 48 hrs: middle row, 60 hrs: bottom row). Only the rim of the spheres was infected with HSVQ treated spheres (bottom panel is bright field image showing the intact sphere at 60 hrs post infection). Note the spread of infectious virus particles into the sphere in all 6 spheroids treated with OV-Chase.

Enhanced OV Spread in Ex Vivo Cultures of Glioma Infected with OV-Chase Compared to Glioma Spheres Infected with HSVQ Referring to FIG. 17, U87ΔEGFR human glioma spheroids (hanging drop method) were placed on organotypic brain slice cultures (from 5-7-day-old mice). The spheroids were infected with $1\times10^4$ pfu of HSVQ or OV-Chase (as described above). We have previously worked and published with this ex vivo model Spread of OV in the sphere was visualized by fluorescent imaging of OV encoded GFP in infected cells over a period of time (24 hrs: top row, 48 hrs: middle row, 60 hrs: bottom row). Infection was apparent only in the rim of the spheres infected with HSVQ, compared to the increased spread to the core of spheres infected with OV-Chase (FIG. 17).

PUBLICATIONS

The following references and others cited herein but not listed here, to the extent that they provide exemplary procedural and other details supplementary to those set forth herein, are specifically incorporated herein by reference.

1. Terada, K.; Wakimoto, H.; Tyminski, E.; Chiocca, E. A. Saeki, Y. Development of a rapid method to generate multiple oncolytic hsv vectors and their in vivo evaluation using syngeneic mouse tumor models. *Gene Ther* 2006, 13, 705-14.
2. Yang, G. P. Lau, L. F. Cyr61, product of a growth factor-inducible immediate early gene, is associated with the extracellular matrix and the cell surface. *Cell Growth Differ* 1991, 2, 351-7.
3. Pendurthi, U. R.; Tran, T. T.; Post, M. Rao, L. V. Proteolysis of ccn1 by plasmin: Functional implications. *Cancer Res* 2005, 65, 9705-11.
4. Jackson, J. R.; Seed, M. P.; Kircher, C. H.; Willoughby, D. A. Winkler, J. D. The codependence of angiogenesis and chronic inflammation. *Faseb J* 1997, 11, 457-65.
5. Kunstfeld, R.; Hirakawa, S.; Hong, Y. K.; Schacht, V.; Lange-Asschenfeldt, B.; Velasco, P.; Lin, C.; Fiebiger, E.; Wei, X.; Wu, Y.; Hicklin, D.; Bohlen, P. Detmar, M. Induction of cutaneous delayed-type hypersensitivity reactions in vegf-a transgenic mice results in chronic skin inflammation associated with persistent lymphatic hyperplasia. *Blood* 2004, 104, 1048-57.
6. Lange-Asschenfeldt, B.; Weninger, W.; Velasco, P.; Kyriakides, T. R.; Von Andrian, U. H.; Bornstein, P. Detmar, M. Increased and prolonged inflammation and angiogenesis in delayed-type hypersensitivity reactions elicited in the skin of thrombospondin-2-deficient mice. *Blood* 2002, 99, 538-45.
7. Pike, S. E.; Yao, L.; Jones, K. D.; Cherney, B.; Appella, E.; Sakaguchi, K.; Nakhasi, H.; Teruya-Feldstein, J.; Wirth, P.; Gupta, G. Tosato, G. Vasostatin, a calreticulin fragment, inhibits angiogenesis and suppresses tumor growth. *J Exp Med* 1998, 188, 2349-56.
8. Park, Y. W.; Kang, Y. M.; Butterfield, J.; Detmar, M.; Goronzy, J. J. Weyand, C. M. Thrombospondin 2 functions as an endogenous regulator of angiogenesis and inflammation in rheumatoid arthritis. *Am J Pathol* 2004, 165, 2087-98.
9. Babic, A. M.; Kireeva, M. L.; Kolesnikova, T. V. Lau, L. F. Cyr61, a product of a growth factor-inducible immediate early gene, promotes angiogenesis and tumor growth. *Proc Natl Acad Sci USA* 1998, 95, 6355-60.
10. Koh, J. T.; Kook, H.; Kee, H. J.; Seo, Y. W.; Jeong, B. C.; Lee, J. H.; Kim, M. Y.; Yoon, K. C.; Jung, S. Kim, K. K. Extracellular fragment of brain-specific angiogenesis inhibitor 1 suppresses endothelial cell proliferation by blocking alphavbeta5 integrin. *Exp Cell Res* 2004, 294, 172-84.
11. Hellums, E. K.; Markert, J. M.; Parker, J. N.; He, B.; Perbal, B.; Roizman, B.; Whitley, R. J.; Langford, C. P.; Bharara, S. Gillespie, G. Y. Increased efficacy of an interleukin-12-secreting herpes simplex virus in a syngeneic intracranial murine glioma model. *Neuro-oncol* 2005, 7, 213-24.
12. Chiocca, E. A. Oncolytic viruses. *Nat Rev Cancer* 2002, 2, 938-50.
13. Wakimoto, H.; Fulci, G.; Tyminski, E. Chiocca, E. A. Altered expression of antiviral cytokine mrnas associated with cyclophosphamide's enhancement of viral oncolysis. *Gene Ther* 2004, 11, 214-23.
14. Aghi, M. Martuza, R. L. Oncolytic viral therapies—the clinical experience. *Oncogene* 2005, 24, 7802-16.
15. Kambara, H.; Okano, H.; Chiocca, E. A. Saeki, Y. An oncolytic HSV-1 mutant expressing ICP34.5 under control of a nestin promoter increases survival of animals even when symptomatic from a brain tumor. *Cancer Res* 2005, 65, 2832-9.
16. Ikeda, K.; Ichikawa, T.; Wakimoto, H.; Silver, J. S.; Deisboeck, T. S.; Finkelstein, D.; Harsh, G. R. T.; Louis, D. N.; Bartus, R. T.; Hochberg, F. H. Chiocca, E. A. Oncolytic virus therapy of multiple tumors in the brain requires suppression of innate and elicited antiviral responses. *Nat Med* 1999, 5, 881-7.
17. Ikeda, K.; Wakimoto, H.; Ichikawa, T.; Jhung, S.; Hochberg, F. H.; Louis, D. N. Chiocca, E. A. Complement depletion facilitates the infection of multiple brain tumors by an intravascular, replication-conditional herpes simplex virus mutant. *J Virol* 2000, 74, 4765-75.
18. Li, S. Electroporation gene therapy: New developments in vivo and in vitro. *Current gene therapy* 2004, 4, 309-316.
19. Kurre, P.; Anandakumar, P.; Harkey, M. A.; Thomasson, B. Kiem, H. P. Efficient marking of murine long-term repopulating stem cells targeting unseparated marrow cells at low lentiviral vector particle concentration. *Mol Ther* 2004, 9, 914-22.
20. Seth, P. Vector-mediated cancer gene therapy: An overview. *Cancer Biology Therapy* 2005, 4, 512-517.
21. Liu, T. C. Kirn, D. Viruses with deletions in antiapoptotic genes as potential oncolytic agents. *Oncogene* 2005, 24, 6069-79.
22. Liu, T. C.; Wang, Y.; Hallden, G.; Brooks, G.; Francis, J.; Lemoine, N. R. Kirn, D. Functional interactions of antiapoptotic proteins and tumor necrosis factor in the context of a replication-competent adenovirus. *Gene Ther* 2005, 12, 1333-46.
23. Conrad, C.; Miller, C. R.; Ji, Y.; Gomez-Manzano, C.; Bharara, S.; Mcmurray, J. S.; Lang, F. F.; Wong, F.; Sawaya, R.; Yung, W. K. Fueyo, J. Delta24-hycd adenovirus suppresses glioma growth in vivo by combining oncolysis and chemosensitization. *Cancer Gene Ther* 2005, 12, 284-94.
24. Mathis, J. M.; Stoff-Khalili, M. A. Curiel, D. T. Oncolytic adenoviruses—selective retargeting to tumor cells. *Oncogene* 2005, 24, 7775-91.
25. Mohr, I. To replicate or not to replicate: Achieving selective oncolytic virus replication in cancer cells through translational control. *Oncogene* 2005, 24, 7697-709.
26. Markert, J. M.; Medlock, M. D.; Rabkin, S. D.; Gillespie, G. Y.; Todo, T.; Hunter, W. D.; Palmer, C. A.; Feigenbaum, F.; Tornatore, C.; Tufaro, F. Martuza, R. L. Conditionally replicating herpes simplex virus mutant, g207 for the treatment of malignant glioma: Results of a phase i trial. *Gene Ther* 2000, 7, 867-74.
27. Rampling, R.; Cruickshank, G.; Papanastassiou, V.; Nicoll, J.; Hadley, D.; Brennan, D.; Petty, R.; Maclean, A.; Harland, J.; Mckie, E.; Mabbs, R. Brown, M. Toxicity evaluation of replication-competent herpes simplex virus (icp 34.5 null mutant 1716) in patients with recurrent malignant glioma. *Gene Ther* 2000, 7, 859-66.
28. Harrow, S.; Papanastassiou, V.; Harland, J.; Mabbs, R.; Petty, R.; Fraser, M.; Hadley, D.; Patterson, J.; Brown, S. M. Rampling, R. Hsv1716 injection into the brain adjacent to tumour following surgical resection of high-grade glioma: Safety data and long-term survival. *Gene Ther* 2004, 11, 1648-58.
29. Chiocca, E. A.; Abbed, K. M.; Tatter, S.; Louis, D. N.; Hochberg, F. H.; Barker, F.; Kracher, J.; Grossman, S. A.; Fisher, J. D.; Carson, K.; Rosenblum, M.; Mikkelsen, T.; Olson, J.; Markert, J.; Rosenfeld, S.; Nabors, L. B.; Brem, S.; Phuphanich, S.; Freeman, S.; Kaplan, R. Zwiebel, J. A phase i open-label, dose-escalation, multi-institutional trial of injection with an e1b-attenuated adenovirus, onyx-015, into the peritumoral region of recurrent malignant gliomas, in the adjuvant setting. *Mol Ther* 2004, 10, 958-66.
30. Hallak, L. K.; Merchan, J. R.; Storgard, C. M.; Loftus, J. C. Russell, S. J. Targeted measles virus vector displaying echistatin infects endothelial cells via alpha(v)beta3 and leads to tumor regression. *Cancer Res* 2005, 65, 5292-300.
31. Hedley, S. J.; Auf Der Maur, A.; Hohn, S.; Escher, D.; Barberis, A.; Glasgow, J. N.; Douglas, J. T.; Korokhov, N. Curiel, D. T. An adenovirus vector with a chimeric fiber incorporating stabilized single chain antibody achieves targeted gene delivery. *Gene Ther* 2005.
32. Borovjagin, A. V.; Krendelchtchikov, A.; Ramesh, N.; Yu, D. C.; Douglas, J. T. Curiel, D. T. Complex mosaicism is a novel approach to infectivity enhancement of adenovirus type 5-based vectors. *Cancer Gene Ther* 2005, 12, 475-86.
33. Nakano, K.; Asano, R.; Tsumoto, K.; Kwon, H.; Goins, W. F.; Kumagai, I.; Cohen, J. B. Glorioso, J. C. Herpes simplex virus targeting to the egf receptor by a gd-specific soluble bridging molecule. *Mol Ther* 2005, 11, 617-26.
34. Biglari, A.; Bataille, D.; Naumann, U.; Weller, M.; Zirger, J.; Castro, M. G. Lowenstein, P. R. Effects of ectopic decorin in modulating intracranial glioma progression in vivo, in a rat syngeneic model. *Cancer Gene Ther* 2004, 11, 721-32.
35. Mahendra, G.; Kumar, S.; Isayeva, T.; Mahasreshti, P. J.; Curiel, D. T.; Stockardt, C. R.; Grizzle, W. E.; Alapati, V.; Singh, R.; Siegal, G. P.; Meleth, S. Ponnazhagan, S. Antiangiogenic cancer gene therapy by adeno-associated virus 2-mediated stable expression of the soluble fms-like tyrosine kinase-1 receptor. *Cancer Gene Ther* 2005, 12, 26-34.
36. Kikuchi, E.; Menendez, S.; Ohori, M.; Cordon-Cardo, C.; Kasahara, N. Bochner, B. H. Inhibition of orthotopic human bladder tumor growth by lentiviral gene transfer of endostatin. *Clin Cancer Res* 2004, 10, 1835-42.
37. Finger, C.; Sun, Y.; Sanz, L.; Alvarez-Vallina, L.; Buchholz, C. J. Cichutek, K. Replicating retroviral vectors mediating continuous production and secretion of therapeutic gene products from cancer cells. *Cancer Gene Ther* 2005, 12, 464-74.
38. Lawler, S. E.; Peruzzi, P. P. Chiocca, E. A. Genetic strategies for brain tumor therapy. *Cancer Gene Ther* 2005.
39. Varghese, S. Rabkin, S. D. Oncolytic herpes simplex virus vectors for cancer virotherapy. *Cancer Gene Ther* 2002, 9, 967-78.
40. Gillespie, G. Y.; Soroceanu, L.; Manning, T. J., Jr.; Gladson, C. L. Rosenfeld, S. S. Glioma migration can be blocked by nontoxic inhibitors of myosin ii. *Cancer Res* 1999, 59, 2076-82.
41. Brat, D. J.; Kaur, B. Van Meir, E. G. Genetic modulation of hypoxia induced gene expression and angiogenesis: Relevance to brain tumors. *Front Biosci* 2003, 8, D100-16.
42. Nyberg, P.; Xie, L. Kalluri, R. Endogenous inhibitors of angiogenesis. *Cancer Res* 2005, 65, 3967-79.
43. Kaur, B.; Brat, D. J.; Calkins, C. C. Van Meir, E. G. Brain angiogenesis inhibitor 1 is differentially expressed in normal brain and glioblastoma independently of p53 expression. *Am J Pathol* 2003, 162, 19-27.
44. Nam, D. H.; Park, K.; Suh, Y. L. Kim, J. H. Expression of vegf and brain specific angiogenesis inhibitor-1 in glioblastoma: Prognostic significance. *Oncol Rep* 2004, 11, 863-9.
45. Kaur, B.; Brat, D. J.; Devi, N. S. Van Meir, E. G. Vasculostatin, a proteolytic fragment of brain angiogenesis inhibitor 1, is an antiangiogenic and antitumorigenic factor. *Oncogene* 2005.
46. Kaur, B.; Sandberg, E.; Khwaja, F.; Brat, D. J.; Devi, N. S.; Olson, J. J.; Zhang, Z. Van Meir, E. G. Vasculostatin, a 120 kda bai1 fragment can efficiently inhibit intracranial angiogenesis and tumorigenesis, despite a proangiogenic stimulus. *In preparation unpublished results.*

47. Mullen, J. T.; Donahue, J. M.; Chandrasekhar, S.; Yoon, S. S.; Liu, W.; Ellis, L. M.; Nakamura, H.; Kasuya, H.; Pawlik, T. M. Tanabe, K. K. Oncolysis by viral replication and inhibition of angiogenesis by a replication-conditional herpes simplex virus that expresses mouse endostatin. *Cancer* 2004, 101, 869-77.
48. Liu, T. C.; Zhang, T.; Fukuhara, H.; Kuroda, T.; Todo, T.; Canron, X.; Bikfalvi, A.; Martuza, R. L.; Kurtz, A. Rabkin, S. D. Dominant-negative fibroblast growth factor receptor expression enhances antitumoral potency of oncolytic herpes simplex virus in neural tumors. *Clin Cancer Res* 2006, 12, 6791-9.
49. Liu, T. C.; Zhang, T.; Fukuhara, H.; Kuroda, T.; Todo, T.; Martuza, R. L.; Rabkin, S. D. Kurtz, A. Oncolytic hsv armed with platelet factor 4, an antiangiogenic agent, shows enhanced efficacy. *Mol Ther* 2006, 14, 789-97.
50. Aghi, M.; Rabkin, S. D. Martuza, R. L. Angiogenic response caused by oncolytic herpes simplex virus-induced reduced thrombospondin expression can be prevented by specific viral mutations or by administering a thrombospondin-derived peptide. *Cancer Res* 2007, 67, 440-4.
51. Nishimori, H.; Shiratsuchi, T.; Urano, T.; Kimura, Y.; Kiyono, K.; Tatsumi, K.; Yoshida, S.; Ono, M.; Kuwano, M.; Nakamura, Y. Tokino, T. A novel brain-specific p53-target gene, bai1, containing thrombospondin type 1 repeats inhibits experimental angiogenesis. *Oncogene* 1997, 15, 2145-50.
52. Simpson, S. A.; Manchak, M. D.; Hager, E. J.; Krummenacher, C.; Whitbeck, J. C.; Levin, M. J.; Freed, C. R.; Wilcox, C. L.; Cohen, G. H.; Eisenberg, R. J. Pizer, L. I. Nectin-1/hvec mediates herpes simplex virus type 1 entry into primary human sensory neurons and fibroblasts. *J Neurovirol* 2005, 11, 208-18.
53. Goldstein, D. J. Weller, S. K. Herpes simplex virus type 1-induced ribonucleotide reductase activity is dispensable for virus growth and DNA synthesis: Isolation and characterization of an icp6 lacz insertion mutant. *J Virol* 1988, 62, 196-205.
54. Oura, H.; Bertoncini, J.; Velasco, P.; Brown, L. F.; Carmeliet, P. Detmar, M. A critical role of placental growth factor in the induction of inflammation and edema formation. *Blood* 2003, 101, 560-7.
55. Abordo-Adesida, E.; Follenzi, A.; Barcia, C.; Sciascia, S.; Castro, M. G.; Naldini, L. Lowenstein, P. R. Stability of lentiviral vector-mediated transgene expression in the brain in the presence of systemic antivector immune responses. *Hum Gene Ther* 2005, 16, 741-51.
56. Balachandran, S. Barber, G. N. Defective translational control facilitates vesicular stomatitis virus oncolysis. *Cancer Cell* 2004, 5, 51-65.
57. Andreansky, S.; He, B.; Van Cott, J.; Mcghee, J.; Markert, J. M.; Gillespie, G. Y.; Roizman, B. Whitley, R. J. Treatment of intracranial gliomas in immunocompetent mice using herpes simplex viruses that express murine interleukins. *Gene Ther* 1998, 5, 121-30.
58. Bennett, J. J.; Malhotra, S.; Wong, R. J.; Delman, K.; Zager, J.; St-Louis, M.; Johnson, P. Fong, Y. Interleukin 12 secretion enhances antitumor efficacy of oncolytic herpes simplex viral therapy for colorectal cancer. *Ann Surg* 2001, 233, 819-26.
59. Todo, T.; Martuza, R. L.; Dallman, M. J. Rabkin, S. D. In situ expression of soluble b7-1 in the context of oncolytic herpes simplex virus induces potent antitumor immunity. *Cancer Res* 2001, 61, 153-61.
60. Lamfers, M. L.; Fulci, G.; Gianni, D.; Tang, Y.; Kurozomi, K.; Kaur, B.; Moeniralm, S.; Saeki, Y.; Carette, J. E.; Weissleder, R.; Vandertop, W. P.; Van Beusechem, V. W.; Dirven, C. M. Chiocca, E. A. Cyclophosphamide increases transgene expression mediated by an oncolytic adenovirus in glioma-bearing mice monitored by bioluminescence imaging. *Mol Ther* 2006, 14, 779-88.
61. Fulci, G.; Breymann, L.; Gianni, D.; Kurozomi, K.; Rhee, S. S.; Yu, J.; Kaur, B.; Louis, D. N.; Weissleder, R.; Caligiuri, M. A. Chiocca, E. A. Cyclophosphamide enhances glioma virotherapy by inhibiting innate immune responses. *Proc Natl Acad Sci USA* 2006, 103, 12873-8.
62. Xie, D.; Yin, D.; Tong, X.; O'kelly, J.; Mori, A.; Miller, C.; Black, K.; Gui, D.; Said, J. W. Koeffler, H. P. Cyr61 is overexpressed in gliomas and involved in integrin-linked kinase-mediated akt and beta-catenin-tcf/lef signaling pathways. *Cancer Res* 2004, 64, 1987-96.
63. Xie, D.; Miller, C. W.; O'kelly, J.; Nakachi, K.; Sakashita, A.; Said, J. W.; Gornbein, J. Koeffler, H. P. Breast cancer. Cyr61 is overexpressed, estrogen-inducible, and associated with more advanced disease. *J Biol Chem* 2001, 276, 14187-94.
64. Xie, D.; Yin, D.; Wang, H. J.; Liu, G. T.; Elashoff, R.; Black, K. Koeffler, H. P. Levels of expression of cyr61 and ctgf are prognostic for tumor progression and survival of individuals with gliomas. *Clin Cancer Res* 2004, 10, 2072-81.
65. Mo, F. E.; Muntean, A. G.; Chen, C. C.; Stolz, D. B.; Watkins, S. C. Lau, L. F. Cyr61 (ccn1) is essential for placental development and vascular integrity. *Mol Cell Biol* 2002, 22, 8709-20.
66. Menendez, J. A.; Mehmi, I.; Griggs, D. W. Lupu, R. The angiogenic factor cyr61 in breast cancer: Molecular pathology and therapeutic perspectives. *Endocr Relat Cancer* 2003, 10, 141-52.
67. Fukushima, Y.; Oshika, Y.; Tsuchida, T.; Tokunaga, T.; Hatanaka, H.; Kijima, H.; Yamazaki, H.; Ueyama, Y.; Tamaoki, N. Nakamura, M. Brain-specific angiogenesis inhibitor 1 expression is inversely correlated with vascularity and distant metastasis of colorectal cancer. *Int J Oncol* 1998, 13, 967-70.
68. Hatanaka, H.; Oshika, Y.; Abe, Y.; Yoshida, Y.; Hashimoto, T.; Handa, A.; Kijima, H.; Yamazaki, H.; Inoue, H.; Ueyama, Y. Nakamura, M. Vascularization is decreased in pulmonary adenocarcinoma expressing brain-specific angiogenesis inhibitor 1 (bai1). *Int J Mol Med* 2000, 5, 181-3.
69. Lee, J. H.; Koh, J. T.; Shin, B. A.; Ahn, K. Y.; Roh, J. H.; Kim, Y. J. Kim, K. K. Comparative study of angiostatic and anti-invasive gene expressions as prognostic factors in gastric cancer. *Int J Oncol* 2001, 18, 355-61.
70. Kaur, B.; Brat, D. J.; Devi, N. S. Van Meir, E. G. Vasculostatin, a proteolytic fragment of brain angiogenesis inhibitor 1, is an antiangiogenic and antitumorigenic factor. *Oncogene* 2005, 24, 3632-42.
71. Volpert, O. V.; Zaichuk, T.; Zhou, W.; Reiher, F.; Ferguson, T. A.; Stuart, P. M.; Amin, M. Bouck, N. P. Inducer-stimulated fas targets activated endothelium for destruction by anti-angiogenic thrombospondin-1 and pigment epithelium-derived factor. *Nat Med* 2002, 8, 349-57.
72. Sun, X.; Skorstengaard, K. Mosher, D. F. Disulfides modulate rgd-inhibitable cell adhesive activity of thrombospondin. *J Cell Biol* 1992, 118, 693-701.
73. Tyminski, E.; Leroy, S.; Terada, K.; Finkelstein, D. M.; Hyatt, J. L.; Danks, M. K.; Potter, P. M.; Saeki, Y. Chiocca, E. A. Brain tumor oncolysis with replication-conditional herpes simplex virus type 1 expressing the prodrug-activating genes, cyp2b1 and secreted human intestinal carboxylesterase, in combination with cyclophosphamide and irinotecan. *Cancer Res* 2005, 65, 6850-7.
74. Barber, G. N. The dsrna-dependent protein kinase, pkr and cell death. *Cell Death Differ* 2005, 12, 563-70.
75. Jacobs, A.; Breakefield, X. O. Fraefel, C. Hsv-1-based vectors for gene therapy of neurological diseases and brain tumors: Part i. Hsv-1 structure, replication and pathogenesis. *Neoplasia* 1999, 1, 387-401.
76. Galli, R.; Binda, E.; Orfanelli, U.; Cipelletti, B.; Gritti, A.; De Vitis, S.; Fiocco, R.; Foroni, C.; Dimeco, F. Vescovi, A. Isolation and characterization of tumorigenic, stem-like neural precursors from human glioblastoma. *Cancer Res* 2004, 64, 7011-21.
77. Singh, S. K.; Hawkins, C.; Clarke, I. D.; Squire, J. A.; Bayani, J.; Hide, T.; Henkelman, R. M.; Cusimano, M. D. Dirks, P. B. Identification of human brain tumour initiating cells. *Nature* 2004, 432, 396-401.
78. Kambara, H.; Saeki, Y. Chiocca, E. A. Cyclophosphamide allows for in vivo dose reduction of a potent oncolytic virus. *Cancer Res* 2005, 65, 11255-8.
79. Ribatti, D.; Nico, B.; Vacca, A. Presta, M. The gelatin sponge-chorioallantoic membrane assay. *Nature Protocols* 2006, 1, 85-91.
80. Ali, S.; King, G. D.; Curtin, J. F.; Candolfi, M.; Xiong, W.; Liu, C.; Puntel, M.; Cheng, Q.; Prieto, J.; Ribas, A.; Kupiec-Weglinski, J.; Van Rooijen, N.; Lassmann, H.; Lowenstein, P. R. Castro, M. G. Combined immunostimulation and conditional cytotoxic gene therapy provide long-term survival in a large glioma model. *Cancer Res* 2005, 65, 7194-204.
81. Kaur, B.; Tan, C.; Brat, D. J.; Post, D. E. Van Meir, E. G. Genetic and hypoxic regulation of angiogenesis in gliomas. *J Neurooncol* 2004, 70, 229-43.
82. Jain, R. K. Normalization of tumor vasculature: An emerging concept in antiangiogenic therapy. *Science* 2005, 307, 58-62.
83. Kaur, B.; Khwaja, F. W.; Severson, E. A.; Matheny, S. L.; Brat, D. J. Van Meir, E. G. Hypoxia and the hypoxia-inducible-factor pathway in glioma growth and angiogenesis. *Neuro-oncol* 2005, 7, 134-53.
84. Boviatsis, E. J.; Scharf, J. M.; Chase, M.; Harrington, K.; Kowall, N. W.; Breakefield, X. O. Chiocca, E. A. Antitumor activity and reporter gene transfer into rat brain neoplasms inoculated with herpes simplex virus vectors defective in thymidine kinase or ribonucleotide reductase. *Gene Ther* 1994, 1, 323-31.
85. Vredenburgh, J. J.; Desjardins, A.; Herndon, J. E., 2nd; Dowell, J. M.; Reardon, D. A.; Quinn, J. A.; Rich, J. N.; Sathornsumetee, S.; Gururangan, S.; Wagner, M.; Bigner, D. D.; Friedman, A. H. Friedman, H. S. Phase ii trial of bevacizumab and irinotecan in recurrent malignant glioma. *Clin Cancer Res* 2007, 13, 1253-9.
86. Lamfers, M. L.; Fulci, G.; Gianni, D.; Tang, Y.; Kurozumi, K.; Kaur, B.; Moeniralm, S.; Saeki, Y.; Carette, J. E.; Weissleder, R.; Vandertop, W. P.; Van Beusechem, V. W.; Dirven, C. M. Chiocca, E. A. Cyclophosphamide increases transgene expression mediated by an oncolytic adenovirus in glioma-bearing mice monitored by bioluminescence imaging. *Mol Ther* 2006.

Unless otherwise defined, all technical and scientific terms used herein have the same meaning as commonly understood by one of ordinary skill in the art to which this invention pertains. Although methods and materials similar or equivalent to those described herein can be used in the practice or testing of the exemplary embodiments, suitable methods and materials are described above. All publications, patent applications, patents, and other references mentioned herein are incorporated by reference in their entirety. In case of conflict, the present specification, including definitions, will control. In addition, the materials, methods, and examples are illustrative only and not intended to be limiting.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A recombinant expression vector comprising:
a nucleic acid that comprises a nucleotide sequence according to SEQ ID NO: 3 or a degenerate variant thereof, the sequence operably linked to an immediate early HSV promoter IE4/5,
wherein the nucleotide sequence encodes an angiostatic polypeptide.

2. The recombinant expression vector of claim 1, wherein: the nucleic acid is a modified herpes simplex virus characterized by being a mutant deficient for both copies of its native $\gamma_1 34.5$ gene.

3. The recombinant expression vector of claim 1, wherein: the nucleic acid further comprises a nucleotide sequence encoding a Chase ABC polypeptide.

4. The recombinant expression vector of claim 2, wherein: the nucleic acid further comprises a nucleotide sequence encoding a Chase ABC polypeptide.

5. The recombinant expression vector of claim 1, wherein: the vector is a modified herpes simplex virus.

* * * * *

UNITED STATES PATENT AND TRADEMARK OFFICE
CERTIFICATE OF CORRECTION

PATENT NO. : 8,450,106 B2  
APPLICATION NO. : 12/697891  
DATED : May 28, 2013  
INVENTOR(S) : Kaur et al.

Page 1 of 1

It is certified that error appears in the above-identified patent and that said Letters Patent is hereby corrected as shown below:

In the Specification

Column 1, Line 16 (approx.), after the first paragraph, please add:
"STATEMENT REGARDING FEDERALLY SPONSORED RESEARCH OR DEVELOPMENT
This invention was made with government support under grant number R21 NS056203 awarded by the National Institutes of Health. The government has certain rights in the invention."

Signed and Sealed this
Fourth Day of August, 2020

Andrei Iancu
*Director of the United States Patent and Trademark Office*

SEQUENCE LISTING

```
<160> NUMBER OF SEQ ID NOS: 12

<210> SEQ ID NO 1
<211> LENGTH: 2796
<212> TYPE: DNA
<213> ORGANISM: Homo sapiens
<220> FEATURE:
<221> NAME/KEY: CDS
<222> LOCATION: (1)..(2796)

<400> SEQUENCE: 1 atg agg ggc cag gcc gcc gcc ccg ggc ccc gtc tgg atc ctc gcc ccg      48
Met Arg Gly Gln Ala Ala Ala Pro Gly Pro Val Trp Ile Leu Ala Pro
1               5                   10                  15 ctg cta ctg ctg ctg ctg ctg ctg gga cgc cgc gcg cgg gcg gcc gcc      96
Leu Leu Leu Leu Leu Leu Leu Leu Gly Arg Arg Ala Arg Ala Ala Ala
            20                  25                  30 gga gca gac gcg ggg ccc ggg ccc gag ccg tgc gcc acg ctg gtg cag     144
Gly Ala Asp Ala Gly Pro Gly Pro Glu Pro Cys Ala Thr Leu Val Gln
        35                  40                  45 gga aag ttc ttc ggc tac ttc tcc gcg gcc gcc gtg ttc ccg gcc aac     192
Gly Lys Phe Phe Gly Tyr Phe Ser Ala Ala Ala Val Phe Pro Ala Asn
```

```
                 50                    55                    60
gcc tcg cgc tgc tcc tgg acg cta cgc aac ccg gac ccg cgg cgc tac       240
Ala Ser Arg Cys Ser Trp Thr Leu Arg Asn Pro Asp Pro Arg Arg Tyr
 65                  70                    75                    80 act ctc tac atg aag gtg gcc aag gcg ccc gtg ccc tgc agc ggc ccc       288
Thr Leu Tyr Met Lys Val Ala Lys Ala Pro Val Pro Cys Ser Gly Pro
                     85                    90                    95 ggc cgc gtg cgc acc tac cag ttc gac tcc ttc ctc gag tcc acg cgc       336
Gly Arg Val Arg Thr Tyr Gln Phe Asp Ser Phe Leu Glu Ser Thr Arg
                100                   105                   110 acc tac ctg ggc gtg gag agc ttc gac gag gtg ctg cgg ctc tgc gac       384
Thr Tyr Leu Gly Val Glu Ser Phe Asp Glu Val Leu Arg Leu Cys Asp
            115                   120                   125 ccc tcc gca ccc ctg gcc ttc ctg cag gcc agc aag cag ttc ctg cag       432
Pro Ser Ala Pro Leu Ala Phe Leu Gln Ala Ser Lys Gln Phe Leu Gln
        130                   135                   140 atg cgg cgc cag cag ccg ccc cag cac gac ggg ctc cgg ccc cgg gcc       480
Met Arg Arg Gln Gln Pro Pro Gln His Asp Gly Leu Arg Pro Arg Ala
145                   150                   155                   160 ggg ccg ccg ggc ccc acc gac gac ttc tcc gtg gag tac ctg gtg gtg       528
Gly Pro Pro Gly Pro Thr Asp Asp Phe Ser Val Glu Tyr Leu Val Val
                    165                   170                   175 ggg aac cgc aac ccc agc cgt gcc gcc tgc cag atg ctg tgc cgc tgg       576
Gly Asn Arg Asn Pro Ser Arg Ala Ala Cys Gln Met Leu Cys Arg Trp
                180                   185                   190 ctg gac gcg tgt ctg gcc ggt agt cgc agc tcg cac ccc tgc ggg atc       624
Leu Asp Ala Cys Leu Ala Gly Ser Arg Ser Ser His Pro Cys Gly Ile
            195                   200                   205 atg cag acc ccc tgc gcc tgc ctg ggc ggc gag gcg ggc ggc cct gcc       672
Met Gln Thr Pro Cys Ala Cys Leu Gly Gly Glu Ala Gly Gly Pro Ala
        210                   215                   220 gcg gga ccc ctg gcc ccc cgc ggg gat gtc tgc ttg aga gat gcg gtg       720
Ala Gly Pro Leu Ala Pro Arg Gly Asp Val Cys Leu Arg Asp Ala Val
225                   230                   235                   240 gct ggt ggc cct gaa aac tgc ctc acc agc ctg acc cag gac cgg ggc       768
Ala Gly Gly Pro Glu Asn Cys Leu Thr Ser Leu Thr Gln Asp Arg Gly
                    245                   250                   255 ggg cac ggc gcc aca ggc ggc tgg aag ctg tgg tcc ctg tgg ggc gaa       816
Gly His Gly Ala Thr Gly Gly Trp Lys Leu Trp Ser Leu Trp Gly Glu
                260                   265                   270 tgc acg cgg gac tgc ggg gga ggc ctc cag acg cgg acg cgc acc tgc       864
Cys Thr Arg Asp Cys Gly Gly Gly Leu Gln Thr Arg Thr Arg Thr Cys
            275                   280                   285 ctg ccc gcg ccg ggc gtg gag ggc ggc ggc tgc gag ggg gtg ctg gag       912
Leu Pro Ala Pro Gly Val Glu Gly Gly Gly Cys Glu Gly Val Leu Glu
        290                   295                   300 gag ggt cgc cag tgc aac cgc gag gcc tgc ggc ccc gct ggg cgc acc       960
Glu Gly Arg Gln Cys Asn Arg Glu Ala Cys Gly Pro Ala Gly Arg Thr
305                   310                   315                   320 agc tcc cgg agc cag tcc ctg cgg tcc aca gat gcc cgg cgg cgc gag       1008
Ser Ser Arg Ser Gln Ser Leu Arg Ser Thr Asp Ala Arg Arg Arg Glu
                    325                   330                   335 gag ctg ggg gac gag ctg cag cag ttt ggg ttc cca gcc ccc cag acc       1056
Glu Leu Gly Asp Glu Leu Gln Gln Phe Gly Phe Pro Ala Pro Gln Thr
                340                   345                   350 ggt gac cca gca gcc gag gag tgg tcc ccg tgg agc gtg tgc tcc agc       1104
Gly Asp Pro Ala Ala Glu Glu Trp Ser Pro Trp Ser Val Cys Ser Ser
            355                   360                   365 acc tgc ggc gag ggc tgg cag acc cgc acg cgc ttc tgc gtg tcc tcc       1152
Thr Cys Gly Glu Gly Trp Gln Thr Arg Thr Arg Phe Cys Val Ser Ser
```

```
                370                   375                   380
tcc tac agc acg cag tgc agc gga ccc ctg cgc gag cag cgg ctg tgc      1200
Ser Tyr Ser Thr Gln Cys Ser Gly Pro Leu Arg Glu Gln Arg Leu Cys
385                   390                   395                   400 aac aac tct gcc gtg tgc cca gtg cat ggt gcc tgg gat gag tgg tcg      1248
Asn Asn Ser Ala Val Cys Pro Val His Gly Ala Trp Asp Glu Trp Ser
                      405                   410                   415 ccc tgg agc ctc tgc tcc agc acc tgt ggc cgt ggc ttt cgg gat cgc      1296
Pro Trp Ser Leu Cys Ser Ser Thr Cys Gly Arg Gly Phe Arg Asp Arg
        420                   425                   430 acg cgc acc tgc agg ccc ccc cag ttt ggg ggc aac ccc tgt gag ggc      1344
Thr Arg Thr Cys Arg Pro Pro Gln Phe Gly Gly Asn Pro Cys Glu Gly
            435                   440                   445 cct gag aag caa acc aag ttc tgc aac att gcc ctg tgc cct ggc cgg      1392
Pro Glu Lys Gln Thr Lys Phe Cys Asn Ile Ala Leu Cys Pro Gly Arg
450                   455                   460 gca gtg gat gga aac tgg aat gag tgg tcg agc tgg agc gcc tgc tcc      1440
Ala Val Asp Gly Asn Trp Asn Glu Trp Ser Ser Trp Ser Ala Cys Ser
465                   470                   475                   480 gcc agc tgc tcc cag ggc cga cag cag cgc acg cgt gaa tgc aac ggg      1488
Ala Ser Cys Ser Gln Gly Arg Gln Gln Arg Thr Arg Glu Cys Asn Gly
                      485                   490                   495 cct tcc tac ggg ggt gcg gag tgc cag ggc cac tgg gtg gag acc cga      1536
Pro Ser Tyr Gly Gly Ala Glu Cys Gln Gly His Trp Val Glu Thr Arg
        500                   505                   510 gac tgc ttc ctg cag cag tgc cca gtg gat ggc aag tgg cag gcc tgg      1584
Asp Cys Phe Leu Gln Gln Cys Pro Val Asp Gly Lys Trp Gln Ala Trp
            515                   520                   525 gcg tca tgg ggc agt tgc agc gtc acg tgt ggg gct ggc agc cag cga      1632
Ala Ser Trp Gly Ser Cys Ser Val Thr Cys Gly Ala Gly Ser Gln Arg
530                   535                   540 cgg gag cgt gtc tgc tct ggg ccc ttc ttc ggg gga gca gcc tgc cag      1680
Arg Glu Arg Val Cys Ser Gly Pro Phe Phe Gly Gly Ala Ala Cys Gln
545                   550                   555                   560 ggc ccc cag gat gag tac cgg cag tgc ggc acc cag cgg tgt ccc gag      1728
Gly Pro Gln Asp Glu Tyr Arg Gln Cys Gly Thr Gln Arg Cys Pro Glu
                      565                   570                   575 ccc cat gag atc tgt gat gag gac aac ttt ggt gct gtg atc tgg aag      1776
Pro His Glu Ile Cys Asp Glu Asp Asn Phe Gly Ala Val Ile Trp Lys
        580                   585                   590 gag acc cca gcg gga gag gtg gct gct gtc cgg tgt ccc cgc aac gcc      1824
Glu Thr Pro Ala Gly Glu Val Ala Ala Val Arg Cys Pro Arg Asn Ala
            595                   600                   605 aca gga ctc atc ctg cga cgg tgt gag ctg gac gag gaa ggc atc gcc      1872
Thr Gly Leu Ile Leu Arg Arg Cys Glu Leu Asp Glu Glu Gly Ile Ala
610                   615                   620 tac tgg gag ccc ccc acc tac atc cgc tgt gtt tcc att gac tac aga      1920
Tyr Trp Glu Pro Pro Thr Tyr Ile Arg Cys Val Ser Ile Asp Tyr Arg
625                   630                   635                   640 aac atc cag atg atg acc cgg gag cac ctg gcc aag gct cag cga ggg      1968
Asn Ile Gln Met Met Thr Arg Glu His Leu Ala Lys Ala Gln Arg Gly
                      645                   650                   655 ctg cct ggg gag ggg gtc tcg gag gtc atc cag aca ctg gtg gag atc      2016
Leu Pro Gly Glu Gly Val Ser Glu Val Ile Gln Thr Leu Val Glu Ile
        660                   665                   670 tct cag gac ggg acc agc tac agt ggg gac ctg ctg tcc acc atc gat      2064
Ser Gln Asp Gly Thr Ser Tyr Ser Gly Asp Leu Leu Ser Thr Ile Asp
            675                   680                   685 gtc ctg agg aac atg aca gag att ttc cgg aga gcg tac tac agc ccc      2112
Val Leu Arg Asn Met Thr Glu Ile Phe Arg Arg Ala Tyr Tyr Ser Pro
```

-continued

```
                690                 695                 700
acc cct ggg gac gta cag aac ttt gtc cag atc ctt agc aac ctg ttg      2160
Thr Pro Gly Asp Val Gln Asn Phe Val Gln Ile Leu Ser Asn Leu Leu
705                 710                 715                 720 gca gag gag aat cgg gac aag tgg gag gag gcc cag ctg gcg ggc ccc      2208
Ala Glu Glu Asn Arg Asp Lys Trp Glu Glu Ala Gln Leu Ala Gly Pro
                725                 730                 735 aac gcc aag gag ctg ttc cgg ctg gtg gag gac ttt gtg gac gtc atc      2256
Asn Ala Lys Glu Leu Phe Arg Leu Val Glu Asp Phe Val Asp Val Ile
            740                 745                 750 ggc ttc cgc atg aag gac ctg agg gat gca tac cag gtg aca gac aac      2304
Gly Phe Arg Met Lys Asp Leu Arg Asp Ala Tyr Gln Val Thr Asp Asn
        755                 760                 765 ctg gtt ctc agc atc cat aag ctc cca gcc agc gga gcc act gac atc      2352
Leu Val Leu Ser Ile His Lys Leu Pro Ala Ser Gly Ala Thr Asp Ile
    770                 775                 780 agc ttc ccc atg aag ggc tgg cgg gcc acg ggt gac tgg gcc aag gtg      2400
Ser Phe Pro Met Lys Gly Trp Arg Ala Thr Gly Asp Trp Ala Lys Val
785                 790                 795                 800 cca gag gac agg gtc act gtg tcc aag agt gtc ttc tcc acg ggg ctg      2448
Pro Glu Asp Arg Val Thr Val Ser Lys Ser Val Phe Ser Thr Gly Leu
                805                 810                 815 aca gag gcc gat gaa gca tcc gtg ttt gtg gtg ggc acc gtg ctc tac      2496
Thr Glu Ala Asp Glu Ala Ser Val Phe Val Val Gly Thr Val Leu Tyr
            820                 825                 830 agg aac ctg ggc agc ttc ctg gcc ctg cag agg aac acg acc gtc ctg      2544
Arg Asn Leu Gly Ser Phe Leu Ala Leu Gln Arg Asn Thr Thr Val Leu
        835                 840                 845 aat tct aag gtg atc tcc gtg act gtg aaa ccc ccg cct cgc tcc ctg      2592
Asn Ser Lys Val Ile Ser Val Thr Val Lys Pro Pro Pro Arg Ser Leu
    850                 855                 860 cgc aca ccc ttg gag atc gag ttt gcc cac atg tat aat ggc acc acc      2640
Arg Thr Pro Leu Glu Ile Glu Phe Ala His Met Tyr Asn Gly Thr Thr
865                 870                 875                 880 aac cag acc tgt atc ctg tgg gat gag acg gat gta ccc tcc tcc tcc      2688
Asn Gln Thr Cys Ile Leu Trp Asp Glu Thr Asp Val Pro Ser Ser Ser
                885                 890                 895 gcc ccc ccg cag ctc ggg ccc tgg tcg tgg cgc ggc tgc cgc acg gtg      2736
Ala Pro Pro Gln Leu Gly Pro Trp Ser Trp Arg Gly Cys Arg Thr Val
            900                 905                 910 ccc ctc gac gcc ctc cgg acg cgc tgc ctc tgt gac cgg ctc tcc acc      2784
Pro Leu Asp Ala Leu Arg Thr Arg Cys Leu Cys Asp Arg Leu Ser Thr
        915                 920                 925 ttc gat atc tta                                                      2796
Phe Asp Ile Leu
    930
```

<210> SEQ ID NO 2
<211> LENGTH: 932
<212> TYPE: PRT
<213> ORGANISM: Homo sapiens

<400> SEQUENCE: 2

```
Met Arg Gly Gln Ala Ala Ala Pro Gly Pro Val Trp Ile Leu Ala Pro
1               5                   10                  15

Leu Leu Leu Leu Leu Leu Leu Leu Gly Arg Arg Ala Arg Ala Ala Ala
                20                  25                  30

Gly Ala Asp Ala Gly Pro Gly Pro Glu Pro Cys Ala Thr Leu Val Gln
            35                  40                  45

Gly Lys Phe Phe Gly Tyr Phe Ser Ala Ala Ala Val Phe Pro Ala Asn
```

```
                  50                  55                  60
Ala Ser Arg Cys Ser Trp Thr Leu Arg Asn Pro Asp Pro Arg Tyr
65                  70                  75                  80

Thr Leu Tyr Met Lys Val Ala Lys Ala Pro Val Pro Cys Ser Gly Pro
                85                  90                  95

Gly Arg Val Arg Thr Tyr Gln Phe Asp Ser Phe Leu Glu Ser Thr Arg
                100                 105                 110

Thr Tyr Leu Gly Val Glu Ser Phe Asp Glu Val Leu Arg Leu Cys Asp
                115                 120                 125

Pro Ser Ala Pro Leu Ala Phe Leu Gln Ala Ser Lys Gln Phe Leu Gln
130                 135                 140

Met Arg Arg Gln Gln Pro Pro Gln His Asp Gly Leu Arg Pro Arg Ala
145                 150                 155                 160

Gly Pro Pro Gly Pro Thr Asp Asp Phe Ser Val Glu Tyr Leu Val Val
                165                 170                 175

Gly Asn Arg Asn Pro Ser Arg Ala Ala Cys Gln Met Leu Cys Arg Trp
                180                 185                 190

Leu Asp Ala Cys Leu Ala Gly Ser Arg Ser His Pro Cys Gly Ile
                195                 200                 205

Met Gln Thr Pro Cys Ala Cys Leu Gly Gly Glu Ala Gly Gly Pro Ala
210                 215                 220

Ala Gly Pro Leu Ala Pro Arg Gly Asp Val Cys Leu Arg Asp Ala Val
225                 230                 235                 240

Ala Gly Gly Pro Glu Asn Cys Leu Thr Ser Leu Thr Gln Asp Arg Gly
                245                 250                 255

Gly His Gly Ala Thr Gly Gly Trp Lys Leu Trp Ser Leu Trp Gly Glu
                260                 265                 270

Cys Thr Arg Asp Cys Gly Gly Gly Leu Gln Thr Arg Thr Arg Thr Cys
                275                 280                 285

Leu Pro Ala Pro Gly Val Glu Gly Gly Gly Cys Glu Gly Val Leu Glu
290                 295                 300

Glu Gly Arg Gln Cys Asn Arg Glu Ala Cys Gly Pro Ala Gly Arg Thr
305                 310                 315                 320

Ser Ser Arg Ser Gln Ser Leu Arg Ser Thr Asp Ala Arg Arg Glu
                325                 330                 335

Glu Leu Gly Asp Glu Leu Gln Gln Phe Gly Phe Pro Ala Pro Gln Thr
                340                 345                 350

Gly Asp Pro Ala Ala Glu Glu Trp Ser Pro Trp Ser Val Cys Ser Ser
                355                 360                 365

Thr Cys Gly Glu Gly Trp Gln Thr Arg Thr Arg Phe Cys Val Ser Ser
                370                 375                 380

Ser Tyr Ser Thr Gln Cys Ser Gly Pro Leu Arg Glu Gln Arg Leu Cys
385                 390                 395                 400

Asn Asn Ser Ala Val Cys Pro Val His Gly Ala Trp Asp Glu Trp Ser
                405                 410                 415

Pro Trp Ser Leu Cys Ser Ser Thr Cys Gly Arg Gly Phe Arg Asp Arg
                420                 425                 430

Thr Arg Thr Cys Arg Pro Pro Gln Phe Gly Gly Asn Pro Cys Glu Gly
                435                 440                 445

Pro Glu Lys Gln Thr Lys Phe Cys Asn Ile Ala Leu Cys Pro Gly Arg
                450                 455                 460

Ala Val Asp Gly Asn Trp Asn Glu Trp Ser Ser Trp Ser Ala Cys Ser
465                 470                 475                 480
```

```
Ala Ser Cys Ser Gln Gly Arg Gln Arg Thr Arg Glu Cys Asn Gly
                485                 490                 495

Pro Ser Tyr Gly Gly Ala Glu Cys Gln Gly His Trp Val Glu Thr Arg
            500                 505                 510

Asp Cys Phe Leu Gln Gln Cys Pro Val Asp Gly Lys Trp Gln Ala Trp
            515                 520                 525

Ala Ser Trp Gly Ser Cys Ser Val Thr Cys Gly Ala Gly Ser Gln Arg
    530                 535                 540

Arg Glu Arg Val Cys Ser Gly Pro Phe Phe Gly Gly Ala Ala Cys Gln
545                 550                 555                 560

Gly Pro Gln Asp Glu Tyr Arg Gln Cys Gly Thr Gln Arg Cys Pro Glu
                565                 570                 575

Pro His Glu Ile Cys Asp Glu Asp Asn Phe Gly Ala Val Ile Trp Lys
            580                 585                 590

Glu Thr Pro Ala Gly Glu Val Ala Ala Val Arg Cys Pro Arg Asn Ala
            595                 600                 605

Thr Gly Leu Ile Leu Arg Arg Cys Glu Leu Asp Glu Glu Gly Ile Ala
    610                 615                 620

Tyr Trp Glu Pro Pro Thr Tyr Ile Arg Cys Val Ser Ile Asp Tyr Arg
625                 630                 635                 640

Asn Ile Gln Met Met Thr Arg Glu His Leu Ala Lys Ala Gln Arg Gly
                645                 650                 655

Leu Pro Gly Glu Gly Val Ser Glu Val Ile Gln Thr Leu Val Glu Ile
            660                 665                 670

Ser Gln Asp Gly Thr Ser Tyr Ser Gly Asp Leu Leu Ser Thr Ile Asp
            675                 680                 685

Val Leu Arg Asn Met Thr Glu Ile Phe Arg Arg Ala Tyr Tyr Ser Pro
    690                 695                 700

Thr Pro Gly Asp Val Gln Asn Phe Val Gln Ile Leu Ser Asn Leu Leu
705                 710                 715                 720

Ala Glu Glu Asn Arg Asp Lys Trp Glu Glu Ala Gln Leu Ala Gly Pro
                725                 730                 735

Asn Ala Lys Glu Leu Phe Arg Leu Val Glu Asp Phe Val Asp Val Ile
            740                 745                 750

Gly Phe Arg Met Lys Asp Leu Arg Asp Ala Tyr Gln Val Thr Asp Asn
    755                 760                 765

Leu Val Leu Ser Ile His Lys Leu Pro Ala Ser Gly Ala Thr Asp Ile
    770                 775                 780

Ser Phe Pro Met Lys Gly Trp Arg Ala Thr Gly Asp Trp Ala Lys Val
785                 790                 795                 800

Pro Glu Asp Arg Val Thr Val Ser Lys Ser Val Phe Ser Thr Gly Leu
                805                 810                 815

Thr Glu Ala Asp Glu Ala Ser Val Phe Val Val Gly Thr Val Leu Tyr
            820                 825                 830

Arg Asn Leu Gly Ser Phe Leu Ala Leu Gln Arg Asn Thr Thr Val Leu
    835                 840                 845

Asn Ser Lys Val Ile Ser Val Thr Val Lys Pro Pro Arg Ser Leu
    850                 855                 860

Arg Thr Pro Leu Glu Ile Glu Phe Ala His Met Tyr Asn Gly Thr Thr
865                 870                 875                 880

Asn Gln Thr Cys Ile Leu Trp Asp Glu Thr Asp Val Pro Ser Ser Ser
                885                 890                 895

Ala Pro Pro Gln Leu Gly Pro Trp Ser Trp Arg Gly Cys Arg Thr Val
            900                 905                 910
```

-continued

```
Pro Leu Asp Ala Leu Arg Thr Arg Cys Leu Cys Asp Arg Leu Ser Thr
            915                 920                 925

Phe Asp Ile Leu
        930

<210> SEQ ID NO 3
<211> LENGTH: 2962
<212> TYPE: DNA
<213> ORGANISM: Homo sapiens
<220> FEATURE:
<221> NAME/KEY: CDS
<222> LOCATION: (1)..(2961)

<400> SEQUENCE: 3 atg agg ggc cag gcc gcc gcc ccg ggc ccc gtc tgg atc ctc gcc ccg      48
Met Arg Gly Gln Ala Ala Ala Pro Gly Pro Val Trp Ile Leu Ala Pro
1               5                   10                  15 ctg cta ctg ctg ctg ctg ctg gga cgc cgc gcg cgg gcg gcc gcc          96
Leu Leu Leu Leu Leu Leu Leu Gly Arg Arg Ala Arg Ala Ala Ala
            20                  25                  30 gga gca gac gcg ggg ccc ggg ccc gag ccg tgc gcc acg ctg gtg cag     144
Gly Ala Asp Ala Gly Pro Gly Pro Glu Pro Cys Ala Thr Leu Val Gln
        35                  40                  45 gga aag ttc ttc ggc tac ttc tcc gcg gcc gcc gtg ttc ccg gcc aac     192
Gly Lys Phe Phe Gly Tyr Phe Ser Ala Ala Ala Val Phe Pro Ala Asn
    50                  55                  60 gcc tcg cgc tgc tcc tgg acg cta cgc aac ccg gac ccg cgg cgc tac     240
Ala Ser Arg Cys Ser Trp Thr Leu Arg Asn Pro Asp Pro Arg Arg Tyr
65                  70                  75                  80 act ctc tac atg aag gtg gcc aag gcg ccc gtg ccc tgc agc ggc ccc     288
Thr Leu Tyr Met Lys Val Ala Lys Ala Pro Val Pro Cys Ser Gly Pro
                85                  90                  95 ggc cgc gtg cgc acc tac cag ttc gac tcc ttc ctc gag tcc acg cgc     336
Gly Arg Val Arg Thr Tyr Gln Phe Asp Ser Phe Leu Glu Ser Thr Arg
            100                 105                 110 acc tac ctg ggc gtg gag agc ttc gac gag gtg ctg cgg ctc tgc gac     384
Thr Tyr Leu Gly Val Glu Ser Phe Asp Glu Val Leu Arg Leu Cys Asp
        115                 120                 125 ccc tcc gca ccc ctg gcc ttc ctg cag gcc agc aag cag ttc ctg cag     432
Pro Ser Ala Pro Leu Ala Phe Leu Gln Ala Ser Lys Gln Phe Leu Gln
    130                 135                 140 atg cgg cgc cag cag ccg ccc cag cac gac ggg ctc cgg ccc cgg gcc     480
Met Arg Arg Gln Gln Pro Pro Gln His Asp Gly Leu Arg Pro Arg Ala
145                 150                 155                 160 ggg ccg ccg ggc ccc acc gac gac ttc tcc gtg gag tac ctg gtg gtg     528
Gly Pro Pro Gly Pro Thr Asp Asp Phe Ser Val Glu Tyr Leu Val Val
                165                 170                 175 ggg aac cgc aac ccc agc cgt gcc gcc tgc cag atg ctg tgc cgc tgg     576
Gly Asn Arg Asn Pro Ser Arg Ala Ala Cys Gln Met Leu Cys Arg Trp
            180                 185                 190 ctg gac gcg tgt ctg gcc ggt agt cgc agc tcg cac ccc tgc ggg atc     624
Leu Asp Ala Cys Leu Ala Gly Ser Arg Ser Ser His Pro Cys Gly Ile
        195                 200                 205 atg cag acc ccc tgc gcc tgc ctg ggc ggc gag gcg ggc ggc cct gcc     672
Met Gln Thr Pro Cys Ala Cys Leu Gly Gly Glu Ala Gly Gly Pro Ala
    210                 215                 220 gcg gga ccc ctg gcc ccc cgc ggg gat gtc tgc ttg aga gat gcg gtg     720
Ala Gly Pro Leu Ala Pro Arg Gly Asp Val Cys Leu Arg Asp Ala Val
225                 230                 235                 240 gct ggt ggc cct gaa aac tgc ctc acc agc ctg acc cag gac cgg ggc     768
Ala Gly Gly Pro Glu Asn Cys Leu Thr Ser Leu Thr Gln Asp Arg Gly
```

-continued

```
                245                 250                 255
ggg cac ggc gcc aca ggc ggc tgg aag ctg tgg tcc ctg tgg ggc gaa      816
Gly His Gly Ala Thr Gly Gly Trp Lys Leu Trp Ser Leu Trp Gly Glu
        260                 265                 270 tgc acg cgg gac tgc ggg gga ggc ctc cag acg cgg acg cgc acc tgc      864
Cys Thr Arg Asp Cys Gly Gly Gly Leu Gln Thr Arg Thr Arg Thr Cys
        275                 280                 285 ctg ccc gcg ccg ggc gtg gag ggc ggc ggc tgc gag ggg gtg ctg gag      912
Leu Pro Ala Pro Gly Val Glu Gly Gly Gly Cys Glu Gly Val Leu Glu
        290                 295                 300 gag ggt cgc cag tgc aac cgc gag gcc tgc ggc ccc gct ggg cgc acc      960
Glu Gly Arg Gln Cys Asn Arg Glu Ala Cys Gly Pro Ala Gly Arg Thr
305                 310                 315                 320 agc tcc cgg agc cag tcc ctg cgg tcc aca gat gcc cgg cgc gcg gag     1008
Ser Ser Arg Ser Gln Ser Leu Arg Ser Thr Asp Ala Arg Arg Arg Glu
                325                 330                 335 gag ctg ggg gac gag ctg cag cag ttt ggg ttc cca gcc ccc cag acc     1056
Glu Leu Gly Asp Glu Leu Gln Gln Phe Gly Phe Pro Ala Pro Gln Thr
            340                 345                 350 ggt gac cca gca gcc gag gag tgg tcc ccg tgg agc gtg tgc tcc agc     1104
Gly Asp Pro Ala Ala Glu Glu Trp Ser Pro Trp Ser Val Cys Ser Ser
        355                 360                 365 acc tgc ggc gag ggc tgg cag acc cgc acg cgc ttc tgc gtg tcc tcc     1152
Thr Cys Gly Glu Gly Trp Gln Thr Arg Thr Arg Phe Cys Val Ser Ser
        370                 375                 380 tcc tac agc acg cag tgc agc gga ccc ctg cgc gag cag cgg ctg tgc     1200
Ser Tyr Ser Thr Gln Cys Ser Gly Pro Leu Arg Glu Gln Arg Leu Cys
385                 390                 395                 400 aac aac tct gcc gtg tgc cca gtg cat ggt gcc tgg gat gag tgg tcg     1248
Asn Asn Ser Ala Val Cys Pro Val His Gly Ala Trp Asp Glu Trp Ser
                405                 410                 415 ccc tgg agc ctc tgc tcc agc acc tgt ggc cgt ggc ttt cgg gat cgc     1296
Pro Trp Ser Leu Cys Ser Ser Thr Cys Gly Arg Gly Phe Arg Asp Arg
            420                 425                 430 acg cgc acc tgc agg ccc ccc cag ttt ggg ggc aac ccc tgt gag ggc     1344
Thr Arg Thr Cys Arg Pro Pro Gln Phe Gly Gly Asn Pro Cys Glu Gly
        435                 440                 445 cct gag aag caa acc aag ttc tgc aac att gcc ctg tgc cct ggc cgg     1392
Pro Glu Lys Gln Thr Lys Phe Cys Asn Ile Ala Leu Cys Pro Gly Arg
450                 455                 460 gca gtg gat gga aac tgg aat gag tgg tcg agc tgg agc gcc tgc tcc     1440
Ala Val Asp Gly Asn Trp Asn Glu Trp Ser Ser Trp Ser Ala Cys Ser
465                 470                 475                 480 gcc agc tgc tcc cag ggc cga cag cag cgc acg cgt gaa tgc aac ggg     1488
Ala Ser Cys Ser Gln Gly Arg Gln Gln Arg Thr Arg Glu Cys Asn Gly
                485                 490                 495 cct tcc tac ggg ggt gcg gag tgc cag ggc cac tgg gtg gag acc cga     1536
Pro Ser Tyr Gly Gly Ala Glu Cys Gln Gly His Trp Val Glu Thr Arg
            500                 505                 510 gac tgc ttc ctg cag cag tgc cca gtg gat ggc aag tgg cag gcc tgg     1584
Asp Cys Phe Leu Gln Gln Cys Pro Val Asp Gly Lys Trp Gln Ala Trp
        515                 520                 525 gcg tca tgg ggc agt tgc agc gtc acg tgt ggg gct ggc agc cag cga     1632
Ala Ser Trp Gly Ser Cys Ser Val Thr Cys Gly Ala Gly Ser Gln Arg
        530                 535                 540 cgg gag cgt gtc tgc tct ggg ccc ttc ttc ggg gga gca gcc tgc cag     1680
Arg Glu Arg Val Cys Ser Gly Pro Phe Phe Gly Gly Ala Ala Cys Gln
545                 550                 555                 560 ggc ccc cag gat gag tac cgg cag tgc ggc acc cag cgg tgt ccc gag     1728
Gly Pro Gln Asp Glu Tyr Arg Gln Cys Gly Thr Gln Arg Cys Pro Glu
```

-continued

```
                   565                 570                 575
ccc cat gag atc tgt gat gag gac aac ttt ggt gct gtg atc tgg aag    1776
Pro His Glu Ile Cys Asp Glu Asp Asn Phe Gly Ala Val Ile Trp Lys
            580                 585                 590 gag acc cca gcg gga gag gtg gct gct gtc cgg tgt ccc cgc aac gcc    1824
Glu Thr Pro Ala Gly Glu Val Ala Ala Val Arg Cys Pro Arg Asn Ala
        595                 600                 605 aca gga ctc atc ctg cga cgg tgt gag ctg gac gag gaa ggc atc gcc    1872
Thr Gly Leu Ile Leu Arg Arg Cys Glu Leu Asp Glu Glu Gly Ile Ala
    610                 615                 620 tac tgg gag ccc ccc acc tac atc cgc tgt gtt tcc att gac tac aga    1920
Tyr Trp Glu Pro Pro Thr Tyr Ile Arg Cys Val Ser Ile Asp Tyr Arg
625                 630                 635                 640 aac atc cag atg atg acc cgg gag cac ctg gcc aag gct cag cga ggg    1968
Asn Ile Gln Met Met Thr Arg Glu His Leu Ala Lys Ala Gln Arg Gly
                645                 650                 655 ctg cct ggg gag ggg gtc tcg gag gtc atc cag aca ctg gtg gag atc    2016
Leu Pro Gly Glu Gly Val Ser Glu Val Ile Gln Thr Leu Val Glu Ile
            660                 665                 670 tct cag gac ggg acc agc tac agt ggg gac ctg ctg tcc acc atc gat    2064
Ser Gln Asp Gly Thr Ser Tyr Ser Gly Asp Leu Leu Ser Thr Ile Asp
        675                 680                 685 gtc ctg agg aac atg aca gag att ttc cgg aga gcg tac tac agc ccc    2112
Val Leu Arg Asn Met Thr Glu Ile Phe Arg Arg Ala Tyr Tyr Ser Pro
    690                 695                 700 acc cct ggg gac gta cag aac ttt gtc cag atc ctt agc aac ctg ttg    2160
Thr Pro Gly Asp Val Gln Asn Phe Val Gln Ile Leu Ser Asn Leu Leu
705                 710                 715                 720 gca gag gag aat cgg gac aag tgg gag gag gcc cag ctg gcg ggc ccc    2208
Ala Glu Glu Asn Arg Asp Lys Trp Glu Glu Ala Gln Leu Ala Gly Pro
                725                 730                 735 aac gcc aag gag ctg ttc cgg ctg gtg gag gac ttt gtg gac gtc atc    2256
Asn Ala Lys Glu Leu Phe Arg Leu Val Glu Asp Phe Val Asp Val Ile
            740                 745                 750 ggc ttc cgc atg aag gac ctg agg gat gca tac cag gtg aca gac aac    2304
Gly Phe Arg Met Lys Asp Leu Arg Asp Ala Tyr Gln Val Thr Asp Asn
        755                 760                 765 ctg gtt ctc agc atc cat aag ctc cca gcc agc gga gcc act gac atc    2352
Leu Val Leu Ser Ile His Lys Leu Pro Ala Ser Gly Ala Thr Asp Ile
    770                 775                 780 agc ttc ccc atg aag ggc tgg cgg gcc acg ggt gac tgg gcc aag gtg    2400
Ser Phe Pro Met Lys Gly Trp Arg Ala Thr Gly Asp Trp Ala Lys Val
785                 790                 795                 800 cca gag gac agg gtc act gtg tcc aag agt gtc ttc tcc acg ggg ctg    2448
Pro Glu Asp Arg Val Thr Val Ser Lys Ser Val Phe Ser Thr Gly Leu
                805                 810                 815 aca gag gcc gat gaa gca tcc gtg ttt gtg gtg ggc acc gtg ctc tac    2496
Thr Glu Ala Asp Glu Ala Ser Val Phe Val Val Gly Thr Val Leu Tyr
            820                 825                 830 agg aac ctg ggc agc ttc ctg gcc ctg cag agg aac acg acc gtc ctg    2544
Arg Asn Leu Gly Ser Phe Leu Ala Leu Gln Arg Asn Thr Thr Val Leu
        835                 840                 845 aat tct aag gtg atc tcc gtg act gtg aaa ccc ccg cct cgc tcc ctg    2592
Asn Ser Lys Val Ile Ser Val Thr Val Lys Pro Pro Pro Arg Ser Leu
    850                 855                 860 cgc aca ccc ttg gag atc gag ttt gcc cac atg tat aat ggc acc acc    2640
Arg Thr Pro Leu Glu Ile Glu Phe Ala His Met Tyr Asn Gly Thr Thr
865                 870                 875                 880 aac cag acc tgt atc ctg tgg gat gag acg gat gta ccc tcc tcc tcc    2688
Asn Gln Thr Cys Ile Leu Trp Asp Glu Thr Asp Val Pro Ser Ser Ser
```

```
                              885                 890                 895
gcc ccc ccg cag ctc ggg ccc tgg tcg tgg cgc ggc tgc cgc acg gtg          2736
Ala Pro Pro Gln Leu Gly Pro Trp Ser Trp Arg Gly Cys Arg Thr Val
            900                 905                 910 ccc ctc gac gcc ctc cgg acg cgc tgc ctc tgt gac cgg ctc tcc acc          2784
Pro Leu Asp Ala Leu Arg Thr Arg Cys Leu Cys Asp Arg Leu Ser Thr
        915                 920                 925 ttc gat atc tta atc aag ctt ggt acc gag ctc gga tcc act agt cca          2832
Phe Asp Ile Leu Ile Lys Leu Gly Thr Glu Leu Gly Ser Thr Ser Pro
    930                 935                 940 gtg tgg tgg aat tct gca gat atc cag cac agt ggc ggc cgc tcg agt          2880
Val Trp Trp Asn Ser Ala Asp Ile Gln His Ser Gly Gly Arg Ser Ser
945                 950                 955                 960 cta gag ggc ccg cgg ttc gaa caa aaa ctc atc tca gaa gag gat ctg          2928
Leu Glu Gly Pro Arg Phe Glu Gln Lys Leu Ile Ser Glu Glu Asp Leu
                965                 970                 975 aat atg cat acc ggt cat cat cac cat cac cat t                            2962
Asn Met His Thr Gly His His His His His His
            980                 985
```

<210> SEQ ID NO 4
<211> LENGTH: 987
<212> TYPE: PRT
<213> ORGANISM: Homo sapiens

<400> SEQUENCE: 4

```
Met Arg Gly Gln Ala Ala Ala Pro Gly Pro Val Trp Ile Leu Ala Pro
1               5                   10                  15

Leu Leu Leu Leu Leu Leu Leu Leu Gly Arg Arg Ala Arg Ala Ala Ala
                20                  25                  30

Gly Ala Asp Ala Gly Pro Gly Pro Glu Pro Cys Ala Thr Leu Val Gln
            35                  40                  45

Gly Lys Phe Phe Gly Tyr Phe Ser Ala Ala Val Phe Pro Ala Asn
        50                  55                  60

Ala Ser Arg Cys Ser Trp Thr Leu Arg Asn Pro Asp Pro Arg Arg Tyr
65                  70                  75                  80

Thr Leu Tyr Met Lys Val Ala Lys Ala Pro Val Pro Cys Ser Gly Pro
                85                  90                  95

Gly Arg Val Arg Thr Tyr Gln Phe Asp Ser Phe Leu Glu Ser Thr Arg
            100                 105                 110

Thr Tyr Leu Gly Val Glu Ser Phe Asp Glu Val Leu Arg Leu Cys Asp
        115                 120                 125

Pro Ser Ala Pro Leu Ala Phe Leu Gln Ala Ser Lys Gln Phe Leu Gln
    130                 135                 140

Met Arg Arg Gln Gln Pro Pro Gln His Asp Gly Leu Arg Pro Arg Ala
145                 150                 155                 160

Gly Pro Pro Gly Pro Thr Asp Asp Phe Ser Val Glu Tyr Leu Val Val
                165                 170                 175

Gly Asn Arg Asn Pro Ser Arg Ala Ala Cys Gln Met Leu Cys Arg Trp
            180                 185                 190

Leu Asp Ala Cys Leu Ala Gly Ser Arg Ser Ser His Pro Cys Gly Ile
        195                 200                 205

Met Gln Thr Pro Cys Ala Cys Leu Gly Gly Glu Ala Gly Gly Pro Ala
    210                 215                 220

Ala Gly Pro Leu Ala Pro Arg Gly Asp Val Cys Leu Arg Asp Ala Val
225                 230                 235                 240

Ala Gly Gly Pro Glu Asn Cys Leu Thr Ser Leu Thr Gln Asp Arg Gly
```

```
                245             250             255
Gly His Gly Ala Thr Gly Gly Trp Lys Leu Trp Ser Leu Trp Gly Glu
            260             265             270

Cys Thr Arg Asp Cys Gly Gly Leu Gln Thr Arg Thr Arg Thr Cys
        275             280             285

Leu Pro Ala Pro Gly Val Glu Gly Gly Cys Glu Gly Val Leu Glu
    290             295             300

Glu Gly Arg Gln Cys Asn Arg Glu Ala Cys Pro Ala Gly Arg Thr
305             310             315             320

Ser Ser Arg Ser Gln Ser Leu Arg Ser Thr Asp Ala Arg Arg Glu
            325             330             335

Glu Leu Gly Asp Glu Leu Gln Gln Phe Gly Phe Pro Ala Pro Gln Thr
            340             345             350

Gly Asp Pro Ala Ala Glu Glu Trp Ser Pro Trp Ser Val Cys Ser Ser
            355             360             365

Thr Cys Gly Glu Gly Trp Gln Thr Arg Thr Arg Phe Cys Val Ser Ser
        370             375             380

Ser Tyr Ser Thr Gln Cys Ser Gly Pro Leu Arg Glu Gln Arg Leu Cys
385             390             395             400

Asn Asn Ser Ala Val Cys Pro Val His Gly Ala Trp Asp Glu Trp Ser
            405             410             415

Pro Trp Ser Leu Cys Ser Ser Thr Cys Gly Arg Gly Phe Arg Asp Arg
            420             425             430

Thr Arg Thr Cys Arg Pro Pro Gln Phe Gly Gly Asn Pro Cys Glu Gly
        435             440             445

Pro Glu Lys Gln Thr Lys Phe Cys Asn Ile Ala Leu Cys Pro Gly Arg
    450             455             460

Ala Val Asp Gly Asn Trp Asn Glu Trp Ser Ser Trp Ser Ala Cys Ser
465             470             475             480

Ala Ser Cys Ser Gln Gly Arg Gln Arg Thr Arg Glu Cys Asn Gly
            485             490             495

Pro Ser Tyr Gly Gly Ala Glu Cys Gln Gly His Trp Val Glu Thr Arg
            500             505             510

Asp Cys Phe Leu Gln Gln Cys Pro Val Asp Gly Lys Trp Gln Ala Trp
        515             520             525

Ala Ser Trp Gly Ser Cys Ser Val Thr Cys Gly Ala Gly Ser Gln Arg
    530             535             540

Arg Glu Arg Val Cys Ser Gly Pro Phe Phe Gly Gly Ala Ala Cys Gln
545             550             555             560

Gly Pro Gln Asp Glu Tyr Arg Gln Cys Gly Thr Gln Arg Cys Pro Glu
            565             570             575

Pro His Glu Ile Cys Asp Glu Asp Asn Phe Gly Ala Val Ile Trp Lys
            580             585             590

Glu Thr Pro Ala Gly Glu Val Ala Ala Val Arg Cys Pro Arg Asn Ala
        595             600             605

Thr Gly Leu Ile Leu Arg Arg Cys Glu Leu Asp Glu Glu Gly Ile Ala
    610             615             620

Tyr Trp Glu Pro Pro Thr Tyr Ile Arg Cys Val Ser Ile Asp Tyr Arg
625             630             635             640

Asn Ile Gln Met Met Thr Arg Glu His Leu Ala Lys Ala Gln Arg Gly
            645             650             655

Leu Pro Gly Glu Gly Val Ser Glu Val Ile Gln Thr Leu Val Glu Ile
            660             665             670
```

```
Ser Gln Asp Gly Thr Ser Tyr Ser Gly Asp Leu Leu Ser Thr Ile Asp
            675                 680                 685

Val Leu Arg Asn Met Thr Glu Ile Phe Arg Arg Ala Tyr Tyr Ser Pro
690                 695                 700

Thr Pro Gly Asp Val Gln Asn Phe Val Gln Ile Leu Ser Asn Leu Leu
705                 710                 715                 720

Ala Glu Glu Asn Arg Asp Lys Trp Glu Glu Gln Leu Ala Gly Pro
            725                 730                 735

Asn Ala Lys Glu Leu Phe Arg Leu Val Glu Asp Phe Val Asp Val Ile
            740                 745                 750

Gly Phe Arg Met Lys Asp Leu Arg Asp Ala Tyr Gln Val Thr Asp Asn
            755                 760                 765

Leu Val Leu Ser Ile His Lys Leu Pro Ala Ser Gly Ala Thr Asp Ile
770                 775                 780

Ser Phe Pro Met Lys Gly Trp Arg Ala Thr Gly Asp Trp Ala Lys Val
785                 790                 795                 800

Pro Glu Asp Arg Val Thr Val Ser Lys Ser Val Phe Ser Thr Gly Leu
            805                 810                 815

Thr Glu Ala Asp Glu Ala Ser Val Phe Val Val Gly Thr Val Leu Tyr
            820                 825                 830

Arg Asn Leu Gly Ser Phe Leu Ala Leu Gln Arg Asn Thr Thr Val Leu
            835                 840                 845

Asn Ser Lys Val Ile Ser Val Thr Val Lys Pro Pro Arg Ser Leu
850                 855                 860

Arg Thr Pro Leu Glu Ile Glu Phe Ala His Met Tyr Asn Gly Thr Thr
865                 870                 875                 880

Asn Gln Thr Cys Ile Leu Trp Asp Glu Thr Asp Val Pro Ser Ser Ser
            885                 890                 895

Ala Pro Pro Gln Leu Gly Pro Trp Ser Trp Arg Gly Cys Arg Thr Val
            900                 905                 910

Pro Leu Asp Ala Leu Arg Thr Arg Cys Leu Cys Asp Arg Leu Ser Thr
            915                 920                 925

Phe Asp Ile Leu Ile Lys Leu Gly Thr Glu Leu Gly Ser Thr Ser Pro
930                 935                 940

Val Trp Trp Asn Ser Ala Asp Ile Gln His Ser Gly Arg Ser Ser
945                 950                 955                 960

Leu Glu Gly Pro Arg Phe Glu Gln Lys Leu Ile Ser Glu Glu Asp Leu
            965                 970                 975

Asn Met His Thr Gly His His His His His His
            980                 985

<210> SEQ ID NO 5
<211> LENGTH: 144
<212> TYPE: DNA
<213> ORGANISM: Herpes simplex virus
<220> FEATURE:
<221> NAME/KEY: promoter
<222> LOCATION: (1)..(144)

<400> SEQUENCE: 5
ttcgcacttc gtcccaatat atatatatta ttagggcgaa gtgcgagcac tggcgccgtg      60
cccgactccg cgccggcccc gggggcgggc ccgggcggcg gggggcgggt ctctccggcg     120
cacataaagg cccggcgcga ccga                                            144

<210> SEQ ID NO 6
<211> LENGTH: 2997
```

<212> TYPE: DNA
<213> ORGANISM: Proteus vulgaris
<220> FEATURE:
<221> NAME/KEY: CDS
<222> LOCATION: (1)..(2997)

<400> SEQUENCE: 6

```
atg gcc acc agc aat cct gca ttt gat cct aaa aat ctg atg cag tca      48
Met Ala Thr Ser Asn Pro Ala Phe Asp Pro Lys Asn Leu Met Gln Ser
1               5                   10                  15 gaa att tac cat ttt gca caa aat aac cca tta gca gac ttc tca tca      96
Glu Ile Tyr His Phe Ala Gln Asn Asn Pro Leu Ala Asp Phe Ser Ser
            20                  25                  30 gat aaa aac tca ata cta acg tta tct gat aaa cgt agc att atg gga     144
Asp Lys Asn Ser Ile Leu Thr Leu Ser Asp Lys Arg Ser Ile Met Gly
        35                  40                  45 aac caa tct ctt tta tgg aaa tgg aaa ggt ggt agt agc ttt act tta     192
Asn Gln Ser Leu Leu Trp Lys Trp Lys Gly Gly Ser Ser Phe Thr Leu
    50                  55                  60 cat aaa aaa ctg att gtc ccc acc gat aaa gaa gca tct aaa gca tgg     240
His Lys Lys Leu Ile Val Pro Thr Asp Lys Glu Ala Ser Lys Ala Trp
65                  70                  75                  80 gga cgc tca tct acc ccc gtt ttc tca ttt tgg ctt tac aat gaa aaa     288
Gly Arg Ser Ser Thr Pro Val Phe Ser Phe Trp Leu Tyr Asn Glu Lys
                85                  90                  95 ccg att gat ggt tat ctt act atc gat ttc gga gaa aaa ctc att tca     336
Pro Ile Asp Gly Tyr Leu Thr Ile Asp Phe Gly Glu Lys Leu Ile Ser
            100                 105                 110 acc agt gag gct cag gca ggc ttt aaa gta aaa tta gat ttc act ggc     384
Thr Ser Glu Ala Gln Ala Gly Phe Lys Val Lys Leu Asp Phe Thr Gly
        115                 120                 125 tgg cgt act gtg gga gtc tct tta aat aac gat ctt gaa aat cga gag     432
Trp Arg Thr Val Gly Val Ser Leu Asn Asn Asp Leu Glu Asn Arg Glu
    130                 135                 140 atg acc tta aat gca acc aat acc tcc tct gat ggt act caa gac agc     480
Met Thr Leu Asn Ala Thr Asn Thr Ser Ser Asp Gly Thr Gln Asp Ser
145                 150                 155                 160 att ggg cgt tct tta ggt gct aaa gtc gat agt att cgt ttt aaa gcg     528
Ile Gly Arg Ser Leu Gly Ala Lys Val Asp Ser Ile Arg Phe Lys Ala
                165                 170                 175 cct tct aat gtg agt cag ggt gaa atc tat atc gac cgt att atg ttt     576
Pro Ser Asn Val Ser Gln Gly Glu Ile Tyr Ile Asp Arg Ile Met Phe
            180                 185                 190 tct gtc gat gat gct cgc tac caa tgg tct gat tat caa gta aaa act     624
Ser Val Asp Asp Ala Arg Tyr Gln Trp Ser Asp Tyr Gln Val Lys Thr
        195                 200                 205 cgc tta tca gaa cct gaa att caa ttt cac aac gta aag cca caa cta     672
Arg Leu Ser Glu Pro Glu Ile Gln Phe His Asn Val Lys Pro Gln Leu
    210                 215                 220 cct gta aca cct gaa aat tta gcg gcc att gat ctt atc cgc caa cgt     720
Pro Val Thr Pro Glu Asn Leu Ala Ala Ile Asp Leu Ile Arg Gln Arg
225                 230                 235                 240 cta att aat gaa ttt gtc gga ggt gaa aaa gag aca aac ctc gca tta     768
Leu Ile Asn Glu Phe Val Gly Gly Glu Lys Glu Thr Asn Leu Ala Leu
                245                 250                 255 gaa gag aat atc agc aaa tta aaa agt gat ttc gat gct ctt aat att     816
Glu Glu Asn Ile Ser Lys Leu Lys Ser Asp Phe Asp Ala Leu Asn Ile
            260                 265                 270 cac act tta gca aat ggt gga acg caa ggc aga cat ctg gtc act gat     864
His Thr Leu Ala Asn Gly Gly Thr Gln Gly Arg His Leu Val Thr Asp
        275                 280                 285
```

```
aaa caa atc att att tat caa cca gag aat cct aac tct caa gat aaa    912
Lys Gln Ile Ile Ile Tyr Gln Pro Glu Asn Pro Asn Ser Gln Asp Lys
    290             295                 300 caa cta ttt gat aat tat gtt att tta ggt aat tac acg aca tta atg    960
Gln Leu Phe Asp Asn Tyr Val Ile Leu Gly Asn Tyr Thr Thr Leu Met
305             310                 315                 320 ttt aat att agc cgt gct tat gtg ctg gaa aaa gat ccc aca caa aag   1008
Phe Asn Ile Ser Arg Ala Tyr Val Leu Glu Lys Asp Pro Thr Gln Lys
                325                 330                 335 gcg caa cta aag cag atg tac tta tta atg aca aag cat tta tta gat   1056
Ala Gln Leu Lys Gln Met Tyr Leu Leu Met Thr Lys His Leu Leu Asp
            340                 345                 350 caa ggc ttt gtt aaa ggg agt gct tta gtg aca acc cat cac tgg gga   1104
Gln Gly Phe Val Lys Gly Ser Ala Leu Val Thr Thr His His Trp Gly
        355                 360                 365 tac agt tct cgt tgg tgg tat att tcc acg tta tta atg tct gat gca   1152
Tyr Ser Ser Arg Trp Trp Tyr Ile Ser Thr Leu Leu Met Ser Asp Ala
    370                 375                 380 cta aaa gaa gcg aac cta caa act caa gtt tat gat tca tta ctg tgg   1200
Leu Lys Glu Ala Asn Leu Gln Thr Gln Val Tyr Asp Ser Leu Leu Trp
385             390                 395                 400 tat tca cgt gag ttt aaa agt agt ttt gat atg aaa gta agt gct gat   1248
Tyr Ser Arg Glu Phe Lys Ser Ser Phe Asp Met Lys Val Ser Ala Asp
                405                 410                 415 agc tct gat cta gat tat ttc aat acc tta tct cgc caa cat tta gcc   1296
Ser Ser Asp Leu Asp Tyr Phe Asn Thr Leu Ser Arg Gln His Leu Ala
            420                 425                 430 tta tta cta cta gag cct gat gat caa aag cgt atc aac tta gtt aat   1344
Leu Leu Leu Leu Glu Pro Asp Asp Gln Lys Arg Ile Asn Leu Val Asn
        435                 440                 445 act ttc agc cat tat atc act ggc gca tta acg caa gtg cca ccg ggt   1392
Thr Phe Ser His Tyr Ile Thr Gly Ala Leu Thr Gln Val Pro Pro Gly
    450                 455                 460 ggt aaa gat ggt tta cgc cct gat ggt aca gca tgg cga cat gaa ggc   1440
Gly Lys Asp Gly Leu Arg Pro Asp Gly Thr Ala Trp Arg His Glu Gly
465             470                 475                 480 aac tat ccg ggc tac tct ttc cca gcc ttt aaa aat gcc tct cag ctt   1488
Asn Tyr Pro Gly Tyr Ser Phe Pro Ala Phe Lys Asn Ala Ser Gln Leu
                485                 490                 495 att tat tta tta cgc gat aca cca ttt tca gtg ggt gaa agt ggt tgg   1536
Ile Tyr Leu Leu Arg Asp Thr Pro Phe Ser Val Gly Glu Ser Gly Trp
            500                 505                 510 aat aac ctg aaa aaa gcg atg gtt tca gcg tgg atc tac agt aat cca   1584
Asn Asn Leu Lys Lys Ala Met Val Ser Ala Trp Ile Tyr Ser Asn Pro
        515                 520                 525 gaa gtt gga tta ccg ctt gca gga aga cac cct ttt aac tca cct tcg   1632
Glu Val Gly Leu Pro Leu Ala Gly Arg His Pro Phe Asn Ser Pro Ser
    530                 535                 540 tta aaa tca gtc gct caa ggc tat tac tgg ctt gcc atg tct gca aaa   1680
Leu Lys Ser Val Ala Gln Gly Tyr Tyr Trp Leu Ala Met Ser Ala Lys
545             550                 555                 560 tca tcg cct gat aaa aca ctt gca tct att tat ctt gcg att agt gat   1728
Ser Ser Pro Asp Lys Thr Leu Ala Ser Ile Tyr Leu Ala Ile Ser Asp
                565                 570                 575 aaa aca caa aat gaa tca act gct att ttt gga gaa act att aca cca   1776
Lys Thr Gln Asn Glu Ser Thr Ala Ile Phe Gly Glu Thr Ile Thr Pro
            580                 585                 590 gcg tct tta cct caa ggt ttc tat gcc ttt aat ggc ggt gct ttt ggt   1824
Ala Ser Leu Pro Gln Gly Phe Tyr Ala Phe Asn Gly Gly Ala Phe Gly
        595                 600                 605
```

```
att cat cgt tgg caa gat aaa atg gtg aca ctg aaa gct tat aac acc       1872
Ile His Arg Trp Gln Asp Lys Met Val Thr Leu Lys Ala Tyr Asn Thr
    610                 615                 620 aat gtt tgg tca tct gaa att tat aac aaa gat aac cgt tat ggc cgt       1920
Asn Val Trp Ser Ser Glu Ile Tyr Asn Lys Asp Asn Arg Tyr Gly Arg
625                 630                 635                 640 tac caa agt cat ggt gtc gct caa ata gtg agt aat ggc tcg cag ctt       1968
Tyr Gln Ser His Gly Val Ala Gln Ile Val Ser Asn Gly Ser Gln Leu
                645                 650                 655 tca cag ggc tat cag caa gaa ggt tgg gat tgg aat aga atg cca ggg       2016
Ser Gln Gly Tyr Gln Gln Glu Gly Trp Asp Trp Asn Arg Met Pro Gly
            660                 665                 670 gca acc act att cac ctt cct ctt aaa gac tta gac agt cct aaa cct       2064
Ala Thr Thr Ile His Leu Pro Leu Lys Asp Leu Asp Ser Pro Lys Pro
        675                 680                 685 cat acc tta atg caa cgt gga gag cgt gga ttt agc gga aca tca tcc       2112
His Thr Leu Met Gln Arg Gly Glu Arg Gly Phe Ser Gly Thr Ser Ser
    690                 695                 700 ctt gaa ggt caa tat ggc atg atg gca ttc gat ctt att tat ccc gcc       2160
Leu Glu Gly Gln Tyr Gly Met Met Ala Phe Asp Leu Ile Tyr Pro Ala
705                 710                 715                 720 aat ctt gag cgt ttt gat cct aat ttc act gcg aaa aag agt gta tta       2208
Asn Leu Glu Arg Phe Asp Pro Asn Phe Thr Ala Lys Lys Ser Val Leu
                725                 730                 735 gcc gct gat aat cac tta att ttt att ggt agc aat ata aat agt agt       2256
Ala Ala Asp Asn His Leu Ile Phe Ile Gly Ser Asn Ile Asn Ser Ser
            740                 745                 750 gat aaa aat aaa aat gtt gaa acg acc tta ttc caa cat gcc att act       2304
Asp Lys Asn Lys Asn Val Glu Thr Thr Leu Phe Gln His Ala Ile Thr
        755                 760                 765 cca aca tta aat acc ctt tgg att aat gga caa aag ata gaa aac atg       2352
Pro Thr Leu Asn Thr Leu Trp Ile Asn Gly Gln Lys Ile Glu Asn Met
    770                 775                 780 cct tat caa aca aca ctt caa caa ggt gat tgg tta att gat agc aat       2400
Pro Tyr Gln Thr Thr Leu Gln Gln Gly Asp Trp Leu Ile Asp Ser Asn
785                 790                 795                 800 ggc aat ggt tac tta att act caa gca gaa aaa gta aat gta agt cgc       2448
Gly Asn Gly Tyr Leu Ile Thr Gln Ala Glu Lys Val Asn Val Ser Arg
                805                 810                 815 caa cat cag gtt tca gcg gaa aat aaa aat cgc caa ccg aca gaa gga       2496
Gln His Gln Val Ser Ala Glu Asn Lys Asn Arg Gln Pro Thr Glu Gly
            820                 825                 830 aac ttt agc tcg gca tgg atc gat cac agc act cgc ccc aaa gat gcc       2544
Asn Phe Ser Ser Ala Trp Ile Asp His Ser Thr Arg Pro Lys Asp Ala
        835                 840                 845 agt tat gag tat atg gtc ttt tta gat gcg aca cct gaa aaa atg gga       2592
Ser Tyr Glu Tyr Met Val Phe Leu Asp Ala Thr Pro Glu Lys Met Gly
    850                 855                 860 gag atg gca caa aaa ttc cgt gaa aat aat ggg tta tat cag gtt ctt       2640
Glu Met Ala Gln Lys Phe Arg Glu Asn Asn Gly Leu Tyr Gln Val Leu
865                 870                 875                 880 cgt aag gat aaa gac gtt cat att att ctc gat aaa ctc agc aat gta       2688
Arg Lys Asp Lys Asp Val His Ile Ile Leu Asp Lys Leu Ser Asn Val
                885                 890                 895 acg gga tat gcc ttt tat cag cca gca tca att gaa gac aaa tgg atc       2736
Thr Gly Tyr Ala Phe Tyr Gln Pro Ala Ser Ile Glu Asp Lys Trp Ile
            900                 905                 910 aaa aag gtt aat aaa cct gca att gtg atg act cat cga caa aaa gac       2784
Lys Lys Val Asn Lys Pro Ala Ile Val Met Thr His Arg Gln Lys Asp
        915                 920                 925
```

```
act ctt att gtc agt gca gtt aca cct gat tta aat atg act cgc caa    2832
Thr Leu Ile Val Ser Ala Val Thr Pro Asp Leu Asn Met Thr Arg Gln
    930                 935                 940 aaa gca gca act cct gtc acc atc aat gtc acg att aat ggc aaa tgg    2880
Lys Ala Ala Thr Pro Val Thr Ile Asn Val Thr Ile Asn Gly Lys Trp
945                 950                 955                 960 caa tct gct gat aaa aat agt gaa gtg aaa tat cag gtt tct ggt gat    2928
Gln Ser Ala Asp Lys Asn Ser Glu Val Lys Tyr Gln Val Ser Gly Asp
                965                 970                 975 aac act gaa ctg acg ttt acg agt tac ttt ggt att cca caa gaa atc    2976
Asn Thr Glu Leu Thr Phe Thr Ser Tyr Phe Gly Ile Pro Gln Glu Ile
            980                 985                 990 aaa ctc tcg cca ctc cct tga                                        2997
Lys Leu Ser Pro Leu Pro
        995

<210> SEQ ID NO 7
<211> LENGTH: 998
<212> TYPE: PRT
<213> ORGANISM: Proteus vulgaris

<400> SEQUENCE: 7

Met Ala Thr Ser Asn Pro Ala Phe Asp Pro Lys Asn Leu Met Gln Ser
1               5                   10                  15

Glu Ile Tyr His Phe Ala Gln Asn Asn Pro Leu Ala Asp Phe Ser Ser
            20                  25                  30

Asp Lys Asn Ser Ile Leu Thr Leu Ser Asp Lys Arg Ser Ile Met Gly
        35                  40                  45

Asn Gln Ser Leu Leu Trp Lys Trp Lys Gly Gly Ser Ser Phe Thr Leu
    50                  55                  60

His Lys Lys Leu Ile Val Pro Thr Asp Lys Glu Ala Ser Lys Ala Trp
65                  70                  75                  80

Gly Arg Ser Ser Thr Pro Val Phe Ser Phe Trp Leu Tyr Asn Glu Lys
                85                  90                  95

Pro Ile Asp Gly Tyr Leu Thr Ile Asp Phe Gly Glu Lys Leu Ile Ser
            100                 105                 110

Thr Ser Glu Ala Gln Ala Gly Phe Lys Val Lys Leu Asp Phe Thr Gly
        115                 120                 125

Trp Arg Thr Val Gly Val Ser Leu Asn Asn Asp Leu Glu Asn Arg Glu
    130                 135                 140

Met Thr Leu Asn Ala Thr Asn Thr Ser Ser Asp Gly Thr Gln Asp Ser
145                 150                 155                 160

Ile Gly Arg Ser Leu Gly Ala Lys Val Asp Ser Ile Arg Phe Lys Ala
                165                 170                 175

Pro Ser Asn Val Ser Gln Gly Glu Ile Tyr Ile Asp Arg Ile Met Phe
            180                 185                 190

Ser Val Asp Asp Ala Arg Tyr Gln Trp Ser Asp Tyr Gln Val Lys Thr
        195                 200                 205

Arg Leu Ser Glu Pro Glu Ile Gln Phe His Asn Val Lys Pro Gln Leu
    210                 215                 220

Pro Val Thr Pro Glu Asn Leu Ala Ala Ile Asp Leu Ile Arg Gln Arg
225                 230                 235                 240

Leu Ile Asn Glu Phe Val Gly Gly Glu Lys Glu Thr Asn Leu Ala Leu
                245                 250                 255

Glu Glu Asn Ile Ser Lys Leu Lys Ser Asp Phe Asp Ala Leu Asn Ile
            260                 265                 270

His Thr Leu Ala Asn Gly Gly Thr Gln Gly Arg His Leu Val Thr Asp
```

```
                275                 280                 285
Lys Gln Ile Ile Ile Tyr Gln Pro Glu Asn Pro Asn Ser Gln Asp Lys
        290                 295                 300

Gln Leu Phe Asp Asn Tyr Val Ile Leu Gly Asn Tyr Thr Thr Leu Met
305                 310                 315                 320

Phe Asn Ile Ser Arg Ala Tyr Val Leu Glu Lys Asp Pro Thr Gln Lys
                325                 330                 335

Ala Gln Leu Lys Gln Met Tyr Leu Leu Met Thr Lys His Leu Leu Asp
            340                 345                 350

Gln Gly Phe Val Lys Gly Ser Ala Leu Val Thr Thr His His Trp Gly
        355                 360                 365

Tyr Ser Ser Arg Trp Trp Tyr Ile Ser Thr Leu Leu Met Ser Asp Ala
    370                 375                 380

Leu Lys Glu Ala Asn Leu Gln Thr Gln Val Tyr Asp Ser Leu Leu Trp
385                 390                 395                 400

Tyr Ser Arg Glu Phe Lys Ser Ser Phe Asp Met Lys Val Ser Ala Asp
                405                 410                 415

Ser Ser Asp Leu Asp Tyr Phe Asn Thr Leu Ser Arg Gln His Leu Ala
            420                 425                 430

Leu Leu Leu Leu Glu Pro Asp Asp Gln Lys Arg Ile Asn Leu Val Asn
        435                 440                 445

Thr Phe Ser His Tyr Ile Thr Gly Ala Leu Thr Gln Val Pro Pro Gly
    450                 455                 460

Gly Lys Asp Gly Leu Arg Pro Asp Gly Thr Ala Trp Arg His Glu Gly
465                 470                 475                 480

Asn Tyr Pro Gly Tyr Ser Phe Pro Ala Phe Lys Asn Ala Ser Gln Leu
                485                 490                 495

Ile Tyr Leu Leu Arg Asp Thr Pro Phe Ser Val Gly Glu Ser Gly Trp
            500                 505                 510

Asn Asn Leu Lys Lys Ala Met Val Ser Ala Trp Ile Tyr Ser Asn Pro
        515                 520                 525

Glu Val Gly Leu Pro Leu Ala Gly Arg His Pro Phe Asn Ser Pro Ser
    530                 535                 540

Leu Lys Ser Val Ala Gln Gly Tyr Tyr Trp Leu Ala Met Ser Ala Lys
545                 550                 555                 560

Ser Ser Pro Asp Lys Thr Leu Ala Ser Ile Tyr Leu Ala Ile Ser Asp
                565                 570                 575

Lys Thr Gln Asn Glu Ser Thr Ala Ile Phe Gly Glu Thr Ile Thr Pro
            580                 585                 590

Ala Ser Leu Pro Gln Gly Phe Tyr Ala Phe Asn Gly Gly Ala Phe Gly
        595                 600                 605

Ile His Arg Trp Gln Asp Lys Met Val Thr Leu Lys Ala Tyr Asn Thr
    610                 615                 620

Asn Val Trp Ser Ser Glu Ile Tyr Asn Lys Asp Asn Arg Tyr Gly Arg
625                 630                 635                 640

Tyr Gln Ser His Gly Val Ala Gln Ile Val Ser Asn Gly Ser Gln Leu
                645                 650                 655

Ser Gln Gly Tyr Gln Gln Glu Gly Trp Asp Trp Asn Arg Met Pro Gly
            660                 665                 670

Ala Thr Thr Ile His Leu Pro Leu Lys Asp Leu Asp Ser Pro Lys Pro
        675                 680                 685

His Thr Leu Met Gln Arg Gly Glu Arg Gly Phe Ser Gly Thr Ser Ser
    690                 695                 700
```

-continued

Leu Glu Gly Gln Tyr Gly Met Met Ala Phe Asp Leu Ile Tyr Pro Ala
705                 710                 715                 720

Asn Leu Glu Arg Phe Asp Pro Asn Phe Thr Ala Lys Lys Ser Val Leu
            725                 730                 735

Ala Ala Asp Asn His Leu Ile Phe Ile Gly Ser Asn Ile Asn Ser Ser
        740                 745                 750

Asp Lys Asn Lys Asn Val Glu Thr Thr Leu Phe Gln His Ala Ile Thr
    755                 760                 765

Pro Thr Leu Asn Thr Leu Trp Ile Asn Gly Gln Lys Ile Glu Asn Met
770                 775                 780

Pro Tyr Gln Thr Thr Leu Gln Gln Gly Asp Trp Leu Ile Asp Ser Asn
785                 790                 795                 800

Gly Asn Gly Tyr Leu Ile Thr Gln Ala Glu Lys Val Asn Val Ser Arg
            805                 810                 815

Gln His Gln Val Ser Ala Glu Asn Lys Asn Arg Gln Pro Thr Glu Gly
        820                 825                 830

Asn Phe Ser Ser Ala Trp Ile Asp His Ser Thr Arg Pro Lys Asp Ala
    835                 840                 845

Ser Tyr Glu Tyr Met Val Phe Leu Asp Ala Thr Pro Glu Lys Met Gly
850                 855                 860

Glu Met Ala Gln Lys Phe Arg Glu Asn Asn Gly Leu Tyr Gln Val Leu
865                 870                 875                 880

Arg Lys Asp Lys Asp Val His Ile Ile Leu Asp Lys Leu Ser Asn Val
            885                 890                 895

Thr Gly Tyr Ala Phe Tyr Gln Pro Ala Ser Ile Glu Asp Lys Trp Ile
        900                 905                 910

Lys Lys Val Asn Lys Pro Ala Ile Val Met Thr His Arg Gln Lys Asp
    915                 920                 925

Thr Leu Ile Val Ser Ala Val Thr Pro Asp Leu Asn Met Thr Arg Gln
930                 935                 940

Lys Ala Ala Thr Pro Val Thr Ile Asn Val Thr Ile Asn Gly Lys Trp
945                 950                 955                 960

Gln Ser Ala Asp Lys Asn Ser Glu Val Lys Tyr Gln Val Ser Gly Asp
            965                 970                 975

Asn Thr Glu Leu Thr Phe Thr Ser Tyr Phe Gly Ile Pro Gln Glu Ile
        980                 985                 990

Lys Leu Ser Pro Leu Pro
        995

<210> SEQ ID NO 8
<211> LENGTH: 3099
<212> TYPE: DNA
<213> ORGANISM: Artificial Sequence
<220> FEATURE:
<223> OTHER INFORMATION: Human Igk attached to N terminal to permit
      secretion of bacterial protein.  N terminal 72 bp of bacterial
      Chase ABC are omitted.
<220> FEATURE:
<221> NAME/KEY: CDS
<222> LOCATION: (1)..(3099)

<400> SEQUENCE: 8 atg gag aca gac aca ctc ctg cta tgg gta ctg ctg ctc tgg gtt cca      48
Met Glu Thr Asp Thr Leu Leu Leu Trp Val Leu Leu Leu Trp Val Pro
1               5                   10                  15 ggt tcc act ggt gac gcg gcc cag ccg gcc agg cgc gcg cgc gtt acg      96
Gly Ser Thr Gly Asp Ala Ala Gln Pro Ala Arg Arg Ala Arg Arg Thr
            20                  25                  30

```
aag ctc gcc ctt acc agc aat cct gca ttt gat cct aaa aat ctg atg      144
Lys Leu Ala Leu Thr Ser Asn Pro Ala Phe Asp Pro Lys Asn Leu Met
         35                  40                  45 cag tca gaa atc tat cat ttt gcg caa agt aac cca tta gag gac ttt      192
Gln Ser Glu Ile Tyr His Phe Ala Gln Ser Asn Pro Leu Glu Asp Phe
     50                  55                  60 tca tca gat aaa aac tca gca ctg acg tta tct gat aaa cgt agc att      240
Ser Ser Asp Lys Asn Ser Ala Leu Thr Leu Ser Asp Lys Arg Ser Ile
65                  70                  75                  80 atg gga aac caa tcc ctt ttg tgg aaa tgg aaa ggt agt agt ttt          288
Met Gly Asn Gln Ser Leu Leu Trp Lys Trp Lys Gly Ser Ser Phe
                 85                  90                  95 act ttg cat aaa aaa ctt att gtc cca aca gat aaa gaa gcg tct aaa      336
Thr Leu His Lys Lys Leu Ile Val Pro Thr Asp Lys Glu Ala Ser Lys
             100                 105                 110 gca tgg gga cga gca tca aca cct gtt tta tca ttt tgg ctt tat aat      384
Ala Trp Gly Arg Ala Ser Thr Pro Val Leu Ser Phe Trp Leu Tyr Asn
         115                 120                 125 gaa aaa ccc att gat ggc tat ctt act atc gat ttt gga gag aag ctg      432
Glu Lys Pro Ile Asp Gly Tyr Leu Thr Ile Asp Phe Gly Glu Lys Leu
     130                 135                 140 aat tca acg agc gaa gcg caa gcg ggt ttt aaa gta aaa cta aat ttc      480
Asn Ser Thr Ser Glu Ala Gln Ala Gly Phe Lys Val Lys Leu Asn Phe
145                 150                 155                 160 act ggc tgg cgt gct gtt ggg atc tct tta aat aac gat ctt gaa aat      528
Thr Gly Trp Arg Ala Val Gly Ile Ser Leu Asn Asn Asp Leu Glu Asn
                 165                 170                 175 cga gag atg acc tta aat gca atg aat acc tct tct gat ggt acg caa      576
Arg Glu Met Thr Leu Asn Ala Met Asn Thr Ser Ser Asp Gly Thr Gln
             180                 185                 190 gac agc att ggt cgc tct tta ggt gct aat gtc gat agt att cga ttt      624
Asp Ser Ile Gly Arg Ser Leu Gly Ala Asn Val Asp Ser Ile Arg Phe
         195                 200                 205 aaa gcc cca tca aat ata ggt cag ggt gaa atc tat atc gat cgt att      672
Lys Ala Pro Ser Asn Ile Gly Gln Gly Glu Ile Tyr Ile Asp Arg Ile
     210                 215                 220 atg ttt tct atc gat gat gct cgc tat caa tgg tct gat tat caa gtt      720
Met Phe Ser Ile Asp Asp Ala Arg Tyr Gln Trp Ser Asp Tyr Gln Val
225                 230                 235                 240 aaa aca cgc tta tca gag cct gag atc caa ttt cat aac gta caa cct      768
Lys Thr Arg Leu Ser Glu Pro Glu Ile Gln Phe His Asn Val Gln Pro
                 245                 250                 255 cag tta ccg gtg aca cct gaa aat cta gct gca att gat ctt att cgc      816
Gln Leu Pro Val Thr Pro Glu Asn Leu Ala Ala Ile Asp Leu Ile Arg
             260                 265                 270 caa cgt ttg ata aat gag ttt gtt ggt ggc gaa aaa gag aca aat ctc      864
Gln Arg Leu Ile Asn Glu Phe Val Gly Gly Glu Lys Glu Thr Asn Leu
         275                 280                 285 gca cta gaa gaa aat att ggt aag tta aaa agt gat ttt gat gct ctt      912
Ala Leu Glu Glu Asn Ile Gly Lys Leu Lys Ser Asp Phe Asp Ala Leu
     290                 295                 300 aat att cac gct tta gag aat ggc aca ata caa ggg cga cac ctg atc      960
Asn Ile His Ala Leu Glu Asn Gly Thr Ile Gln Gly Arg His Leu Ile
305                 310                 315                 320 aca gac aaa caa act att att tac caa cct gaa aat ctc aac cct caa     1008
Thr Asp Lys Gln Thr Ile Ile Tyr Gln Pro Glu Asn Leu Asn Pro Gln
                 325                 330                 335 gat aaa caa cta ttt gat aat tat gtc att tta ggt aat tac aca aca     1056
Asp Lys Gln Leu Phe Asp Asn Tyr Val Ile Leu Gly Asn Tyr Thr Thr
             340                 345                 350
```

```
                                                      -continued
ttg atg ttt aat att agt cgg gct tat gtg ctg gaa aaa gat ccc tca   1104
Leu Met Phe Asn Ile Ser Arg Ala Tyr Val Leu Glu Lys Asp Pro Ser
        355                 360                 365 caa aaa gct caa cta aag cag atg tac tta tta atg aca aaa cac tta   1152
Gln Lys Ala Gln Leu Lys Gln Met Tyr Leu Leu Met Thr Lys His Leu
    370                 375                 380 tta gat caa ggc ttt gtt aaa gga agt gca tta gtc aca acc cat cac   1200
Leu Asp Gln Gly Phe Val Lys Gly Ser Ala Leu Val Thr Thr His His
385                 390                 395                 400 tgg ggg tat agt tct cgt tgg tgg tat att tcc aca tta cta atg tct   1248
Trp Gly Tyr Ser Ser Arg Trp Trp Tyr Ile Ser Thr Leu Leu Met Ser
                405                 410                 415 gat gca cta aaa gag gca aac tta caa act caa gtt tat gat tca ttg   1296
Asp Ala Leu Lys Glu Ala Asn Leu Gln Thr Gln Val Tyr Asp Ser Leu
        420                 425                 430 ttg tgg tat tca cga gag ttt aaa agt agt ttt gat atg aaa gtg ggt   1344
Leu Trp Tyr Ser Arg Glu Phe Lys Ser Ser Phe Asp Met Lys Val Gly
    435                 440                 445 gca gat agc tcc gac tta gac tat ttc aat acc cta tct cgt caa cac   1392
Ala Asp Ser Ser Asp Leu Asp Tyr Phe Asn Thr Leu Ser Arg Gln His
450                 455                 460 tta gcc tta tta cta cta gag cct gat gat caa aaa cgt atc aac tta   1440
Leu Ala Leu Leu Leu Leu Glu Pro Asp Asp Gln Lys Arg Ile Asn Leu
465                 470                 475                 480 gtt aat acc ttc agc cat tac atc act ggc gca tta act caa gta ccg   1488
Val Asn Thr Phe Ser His Tyr Ile Thr Gly Ala Leu Thr Gln Val Pro
                485                 490                 495 ccg ggt ggt aaa ggt ggt tta cgc cct gac ggt act gcg tgg cga cat   1536
Pro Gly Gly Lys Gly Gly Leu Arg Pro Asp Gly Thr Ala Trp Arg His
        500                 505                 510 gaa ggc aac tat cca ggc tac tct ttc cca gct ttt aaa aat gcc tct   1584
Glu Gly Asn Tyr Pro Gly Tyr Ser Phe Pro Ala Phe Lys Asn Ala Ser
    515                 520                 525 caa ctt att tat tta cta cgt ggt acc cca ttt tca gta ggt gaa agc   1632
Gln Leu Ile Tyr Leu Leu Arg Gly Thr Pro Phe Ser Val Gly Glu Ser
530                 535                 540 ggt tgg aat aac cta aaa aaa gcg atg att tca gcg tgg atc tac agt   1680
Gly Trp Asn Asn Leu Lys Lys Ala Met Ile Ser Ala Trp Ile Tyr Ser
545                 550                 555                 560 aat cca gaa gtt gga tta cct ctt gct gga agg cac cct ttt aac tca   1728
Asn Pro Glu Val Gly Leu Pro Leu Ala Gly Arg His Pro Phe Asn Ser
                565                 570                 575 cct tcg tta aaa tca gtc gct caa ggt tac tac tgg ctt gcc atg tct   1776
Pro Ser Leu Lys Ser Val Ala Gln Gly Tyr Tyr Trp Leu Ala Met Ser
        580                 585                 590 gca aaa ccg tct cca gat aaa act ctc gcg tct att tat ctt gca ata   1824
Ala Lys Pro Ser Pro Asp Lys Thr Leu Ala Ser Ile Tyr Leu Ala Ile
    595                 600                 605 agt gat aaa aca caa aat gaa tcg aag gct att ttt gga gaa act att   1872
Ser Asp Lys Thr Gln Asn Glu Ser Lys Ala Ile Phe Gly Glu Thr Ile
610                 615                 620 gca cca gca gcg ttg cct caa ggt ttc tat gcc ttt aat ggc ggg gct   1920
Ala Pro Ala Ala Leu Pro Gln Gly Phe Tyr Ala Phe Asn Gly Gly Ala
625                 630                 635                 640 ttt ggt att cat cgt tgg caa gat aaa atg gtg aca ctg aaa gct tat   1968
Phe Gly Ile His Arg Trp Gln Asp Lys Met Val Thr Leu Lys Ala Tyr
                645                 650                 655 aat acc aat gtt tgg tca tct gaa att tat aat aaa gat aac cgt tat   2016
Asn Thr Asn Val Trp Ser Ser Glu Ile Tyr Asn Lys Asp Asn Arg Tyr
        660                 665                 670
```

```
ggt cgt tat caa agt cat ggt gtc gct caa ata gtg agt aat ggt tcg    2064
Gly Arg Tyr Gln Ser His Gly Val Ala Gln Ile Val Ser Asn Gly Ser
        675                 680                 685 cag ctc tca cag ggc tat cag caa gaa ggt tgg gat tgg aat agg atg    2112
Gln Leu Ser Gln Gly Tyr Gln Gln Glu Gly Trp Asp Trp Asn Arg Met
690                 695                 700 cca gga gca acc act att cat ctt tct ctt aaa gag tta gat agc cct    2160
Pro Gly Ala Thr Thr Ile His Leu Ser Leu Lys Glu Leu Asp Ser Pro
705                 710                 715                 720 aaa cct cat aca tta atg caa cgt ggc gag cgt gga ttt agc gga aca    2208
Lys Pro His Thr Leu Met Gln Arg Gly Glu Arg Gly Phe Ser Gly Thr
                725                 730                 735 tct gcc ctt gat ggt aaa tat ggg atg atg gca ttc gat ctt att tat    2256
Ser Ala Leu Asp Gly Lys Tyr Gly Met Met Ala Phe Asp Leu Ile Tyr
            740                 745                 750 cct acc aac ctt gaa cgt ttt gat cct aat ttc act gcg aaa aag agt    2304
Pro Thr Asn Leu Glu Arg Phe Asp Pro Asn Phe Thr Ala Lys Lys Ser
        755                 760                 765 gta tta gcc gtt gat aat cac tta att ttt att ggt agc aat ata aat    2352
Val Leu Ala Val Asp Asn His Leu Ile Phe Ile Gly Ser Asn Ile Asn
770                 775                 780 agt agt gat aaa aat aaa aat gtt gaa acg act tta ttt caa cat gct    2400
Ser Ser Asp Lys Asn Lys Asn Val Glu Thr Thr Leu Phe Gln His Ala
785                 790                 795                 800 ata aca cca aca tta aat acc att tgg gtt aat gga caa aaa gtt gag    2448
Ile Thr Pro Thr Leu Asn Thr Ile Trp Val Asn Gly Gln Lys Val Glu
                805                 810                 815 acc ttt cct tat caa gca aca ctt aaa caa ggt gat tgg tta att gat    2496
Thr Phe Pro Tyr Gln Ala Thr Leu Lys Gln Gly Asp Trp Leu Ile Asp
            820                 825                 830 agc aac ggt aat ggc tat tta att acg caa gct gaa aaa gta aat att    2544
Ser Asn Gly Asn Gly Tyr Leu Ile Thr Gln Ala Glu Lys Val Asn Ile
        835                 840                 845 agc cgt caa cac cag act tcg gct gaa aat aaa aat cgc caa cca aca    2592
Ser Arg Gln His Gln Thr Ser Ala Glu Asn Lys Asn Arg Gln Pro Thr
850                 855                 860 gaa gga aac ttt agc tcg gca tgg att gat cac agt gtt caa cct aaa    2640
Glu Gly Asn Phe Ser Ser Ala Trp Ile Asp His Ser Val Gln Pro Lys
865                 870                 875                 880 gat tcc aac tat gag tat atg gtc ttt tta gat gct act cct gaa aga    2688
Asp Ser Asn Tyr Glu Tyr Met Val Phe Leu Asp Ala Thr Pro Glu Arg
                885                 890                 895 atg gga gaa ata gca caa aaa ttt cgt gaa aat aat ggg tta tat cag    2736
Met Gly Glu Ile Ala Gln Lys Phe Arg Glu Asn Asn Gly Leu Tyr Gln
            900                 905                 910 gtt ctt cgt aag gat aaa gac gtt cat att att ctc gat aaa ctc agt    2784
Val Leu Arg Lys Asp Lys Asp Val His Ile Ile Leu Asp Lys Leu Ser
        915                 920                 925 aat gta acg gga tat gcc ttt tat cag tct gct tca att gaa gat aaa    2832
Asn Val Thr Gly Tyr Ala Phe Tyr Gln Ser Ala Ser Ile Glu Asp Lys
930                 935                 940 tgg atc aaa aaa gtt gat aaa ccc gcg att gtg atg act cat cga caa    2880
Trp Ile Lys Lys Val Asp Lys Pro Ala Ile Val Met Thr His Arg Gln
945                 950                 955                 960 aaa gat act ctt att gtc agt gct gtt aca cct gat tta aat atg act    2928
Lys Asp Thr Leu Ile Val Ser Ala Val Thr Pro Asp Leu Asn Met Thr
                965                 970                 975 cgc caa aaa gca gca act cct gtc atc atc aat gtc acg att aat ggt    2976
Arg Gln Lys Ala Ala Thr Pro Val Ile Ile Asn Val Thr Ile Asn Gly
            980                 985                 990
```

-continued

```
aaa tgg caa tct gct gat aaa aat agc aaa gta aaa tat agt gtt tca     3024
Lys Trp Gln Ser Ala Asp Lys Asn Ser Lys Val Lys Tyr Ser Val Ser
        995                 1000                1005 ggt gat aac act gaa ctg act ttt acc agc tac ttt ggt att cca         3069
Gly Asp Asn Thr Glu Leu Thr Phe Thr Ser Tyr Phe Gly Ile Pro
    1010                1015                1020 caa gaa atc aaa ctc tcg cca ctc cct tga                             3099
Gln Glu Ile Lys Leu Ser Pro Leu Pro
    1025                1030

<210> SEQ ID NO 9
<211> LENGTH: 1032
<212> TYPE: PRT
<213> ORGANISM: Artificial Sequence
<220> FEATURE:
<223> OTHER INFORMATION: Synthetic Construct

<400> SEQUENCE: 9
```

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
            20                  25                  30

Lys Leu Ala Leu Thr Ser Asn Pro Ala Phe Asp Pro Lys Asn Leu Met
        35                  40                  45

Gln Ser Glu Ile Tyr His Phe Ala Gln Ser Asn Pro Leu Glu Asp Phe
    50                  55                  60

Ser Ser Asp Lys Asn Ser Ala Leu Thr Leu Ser Asp Lys Arg Ser Ile
65                  70                  75                  80

Met Gly Asn Gln Ser Leu Leu Trp Lys Trp Lys Gly Ser Ser Phe
                85                  90                  95

Thr Leu His Lys Lys Leu Ile Val Pro Thr Asp Lys Glu Ala Ser Lys
            100                 105                 110

Ala Trp Gly Arg Ala Ser Thr Pro Val Leu Ser Phe Trp Leu Tyr Asn
        115                 120                 125

Glu Lys Pro Ile Asp Gly Tyr Leu Thr Ile Asp Phe Gly Glu Lys Leu
    130                 135                 140

Asn Ser Thr Ser Glu Ala Gln Ala Gly Phe Lys Val Lys Leu Asn Phe
145                 150                 155                 160

Thr Gly Trp Arg Ala Val Gly Ile Ser Leu Asn Asn Asp Leu Glu Asn
                165                 170                 175

Arg Glu Met Thr Leu Asn Ala Met Asn Thr Ser Ser Asp Gly Thr Gln
            180                 185                 190

Asp Ser Ile Gly Arg Ser Leu Gly Ala Asn Val Asp Ser Ile Arg Phe
        195                 200                 205

Lys Ala Pro Ser Asn Ile Gly Gln Gly Glu Ile Tyr Ile Asp Arg Ile
    210                 215                 220

Met Phe Ser Ile Asp Asp Ala Arg Tyr Gln Trp Ser Asp Tyr Gln Val
225                 230                 235                 240

Lys Thr Arg Leu Ser Glu Pro Glu Ile Gln Phe His Asn Val Gln Pro
                245                 250                 255

Gln Leu Pro Val Thr Pro Glu Asn Leu Ala Ala Ile Asp Leu Ile Arg
            260                 265                 270

Gln Arg Leu Ile Asn Glu Phe Val Gly Gly Lys Glu Thr Asn Leu
        275                 280                 285

Ala Leu Glu Glu Asn Ile Gly Lys Leu Lys Ser Asp Phe Asp Ala Leu
    290                 295                 300

Asn Ile His Ala Leu Glu Asn Gly Thr Ile Gln Gly Arg His Leu Ile

-continued

```
                305                 310                 315                 320
        Thr Asp Lys Gln Thr Ile Ile Tyr Gln Pro Glu Asn Leu Asn Pro Gln
                        325                 330                 335

Asp Lys Gln Leu Phe Asp Asn Tyr Val Ile Leu Gly Asn Tyr Thr Thr
                        340                 345                 350

Leu Met Phe Asn Ile Ser Arg Ala Tyr Val Leu Glu Lys Asp Pro Ser
                        355                 360                 365

Gln Lys Ala Gln Leu Lys Gln Met Tyr Leu Leu Met Thr Lys His Leu
                        370                 375                 380

Leu Asp Gln Gly Phe Val Lys Gly Ser Ala Leu Val Thr Thr His His
        385                 390                 395                 400

Trp Gly Tyr Ser Ser Arg Trp Trp Tyr Ile Ser Thr Leu Leu Met Ser
                        405                 410                 415

Asp Ala Leu Lys Glu Ala Asn Leu Gln Thr Gln Val Tyr Asp Ser Leu
                        420                 425                 430

Leu Trp Tyr Ser Arg Glu Phe Lys Ser Phe Asp Met Lys Val Gly
                        435                 440                 445

Ala Asp Ser Ser Asp Leu Asp Tyr Phe Asn Thr Leu Ser Arg Gln His
                        450                 455                 460

Leu Ala Leu Leu Leu Leu Glu Pro Asp Asp Gln Lys Arg Ile Asn Leu
        465                 470                 475                 480

Val Asn Thr Phe Ser His Tyr Ile Thr Gly Ala Leu Thr Gln Val Pro
                        485                 490                 495

Pro Gly Gly Lys Gly Gly Leu Arg Pro Asp Gly Thr Ala Trp Arg His
                        500                 505                 510

Glu Gly Asn Tyr Pro Gly Tyr Ser Phe Pro Ala Phe Lys Asn Ala Ser
                        515                 520                 525

Gln Leu Ile Tyr Leu Leu Arg Gly Thr Pro Phe Ser Val Gly Glu Ser
                        530                 535                 540

Gly Trp Asn Asn Leu Lys Lys Ala Met Ile Ser Ala Trp Ile Tyr Ser
        545                 550                 555                 560

Asn Pro Glu Val Gly Leu Pro Leu Ala Gly Arg His Pro Phe Asn Ser
                        565                 570                 575

Pro Ser Leu Lys Ser Val Ala Gln Gly Tyr Tyr Trp Leu Ala Met Ser
                        580                 585                 590

Ala Lys Pro Ser Pro Asp Lys Thr Leu Ala Ser Ile Tyr Leu Ala Ile
                        595                 600                 605

Ser Asp Lys Thr Gln Asn Glu Ser Lys Ala Ile Phe Gly Glu Thr Ile
                        610                 615                 620

Ala Pro Ala Ala Leu Pro Gln Gly Phe Tyr Ala Phe Asn Gly Gly Ala
        625                 630                 635                 640

Phe Gly Ile His Arg Trp Gln Asp Lys Met Val Thr Leu Lys Ala Tyr
                        645                 650                 655

Asn Thr Asn Val Trp Ser Ser Glu Ile Tyr Asn Lys Asp Asn Arg Tyr
                        660                 665                 670

Gly Arg Tyr Gln Ser His Gly Val Ala Gln Ile Val Ser Asn Gly Ser
                        675                 680                 685

Gln Leu Ser Gln Gly Tyr Gln Gln Glu Gly Trp Asp Trp Asn Arg Met
                        690                 695                 700

Pro Gly Ala Thr Thr Ile His Leu Ser Leu Lys Glu Leu Asp Ser Pro
        705                 710                 715                 720

Lys Pro His Thr Leu Met Gln Arg Gly Glu Arg Gly Phe Ser Gly Thr
                        725                 730                 735
```

| | | | | | | | | | | | |
|---|---|---|---|---|---|---|---|---|---|---|---|
|Ser|Ala|Leu|Asp|Gly|Lys|Tyr|Gly|Met|Met|Ala|Phe|Asp|Leu|Ile|Tyr|
| | | |740| | | |745| | | |750| | | | |

Ser Ala Leu Asp Gly Lys Tyr Gly Met Met Ala Phe Asp Leu Ile Tyr
            740          745          750

Pro Thr Asn Leu Glu Arg Phe Asp Pro Asn Phe Thr Ala Lys Lys Ser
          755          760          765

Val Leu Ala Val Asp Asn His Leu Ile Phe Ile Gly Ser Asn Ile Asn
 770           775          780

Ser Ser Asp Lys Asn Lys Asn Val Glu Thr Thr Leu Phe Gln His Ala
785           790          795          800

Ile Thr Pro Thr Leu Asn Thr Ile Trp Val Asn Gly Gln Lys Val Glu
          805          810          815

Thr Phe Pro Tyr Gln Ala Thr Leu Lys Gln Gly Asp Trp Leu Ile Asp
           820         825         830

Ser Asn Gly Asn Gly Tyr Leu Ile Thr Gln Ala Glu Lys Val Asn Ile
        835          840          845

Ser Arg Gln His Gln Thr Ser Ala Glu Asn Lys Asn Arg Gln Pro Thr
850           855          860

Glu Gly Asn Phe Ser Ser Ala Trp Ile Asp His Ser Val Gln Pro Lys
865           870          875          880

Asp Ser Asn Tyr Glu Tyr Met Val Phe Leu Asp Ala Thr Pro Glu Arg
          885          890          895

Met Gly Glu Ile Ala Gln Lys Phe Arg Glu Asn Asn Gly Leu Tyr Gln
        900          905          910

Val Leu Arg Lys Asp Lys Asp Val His Ile Ile Leu Asp Lys Leu Ser
     915          920          925

Asn Val Thr Gly Tyr Ala Phe Tyr Gln Ser Ala Ser Ile Glu Asp Lys
 930           935          940

Trp Ile Lys Lys Val Asp Lys Pro Ala Ile Val Met Thr His Arg Gln
945           950          955          960

Lys Asp Thr Leu Ile Val Ser Ala Val Thr Pro Asp Leu Asn Met Thr
          965          970          975

Arg Gln Lys Ala Ala Thr Pro Val Ile Ile Asn Val Thr Ile Asn Gly
        980          985          990

Lys Trp Gln Ser Ala Asp Lys Asn Ser Lys Val Lys Tyr Ser Val Ser
     995          1000        1005

Gly Asp Asn Thr Glu Leu Thr Phe Thr Ser Tyr Phe Gly Ile Pro
 1010           1015          1020

Gln Glu Ile Lys Leu Ser Pro Leu Pro
     1025          1030

```
<210> SEQ ID NO 10
<211> LENGTH: 6915
<212> TYPE: DNA
<213> ORGANISM: Artificial Sequence
<220> FEATURE:
<223> OTHER INFORMATION: Shuttle plasmid containing BstBI to XbaI
      fragment with IE 4/5 operably linked to partial Vasculostatin
      sequence.
<220> FEATURE:
<221> NAME/KEY: misc_feature
<222> LOCATION: (2276)..(6641)
<223> OTHER INFORMATION: IE 4/5 - Vasculostatin (

```
attgggaaga caatagcgat ccggaaccct aatataact tcgtataatg tatgctatac      300
gaagttatta ggtccctcga cctgcaggca tggctaattc tgtcagccgt taagtgttcc      360
tgtgtcactg aaaattgctt tgagaggctc taagggcttc tcagtgcgtt acatccctgg      420
cttgttgtcc acaaccgtta aaccttaaaa gctttaaaag ccttatatat tcttttttt       480 cttataaaac ttaaaccctt agaggctatt taagttgctg atttatatta attttattgt      540
tcaaacatga gagcttagta cgtgaaacat gagagcttag tacgttagcc atgagagctt      600
agtacgttag ccatgagggt ttagttcgtt aaacatgaga gcttagtacg ttaaacatga      660
gagcttagta cgtgaaacat gagagcttag tacgtactat caacaggttg aactgcggat      720
cttgcggccg gccgcaatcg ggcaaatcgc tgaatattcc ttttgtctcc gaccatcagg      780
cacctgagtc gctgtctttt tcgtgacatt cagttcgctg cgctcacggc tctggcagtg      840
aatgggggta aatggcacta caggcgcctt ttatggattc atgcaaggaa actcaaaata      900
atacaagaaa agcccgtcac gggcttctca gggcgtttta tggcgggtct gctatgtggt      960
gctatctgac tttttgctgt tcagcagttc ctgccctctg attttccagt ctgaccactt      1020
cggattatcc cgtgacaggt cattcagact ggctaatgca cccagtaagg cagcggtatc      1080
atcaacgggg tctgacgctc agtggaacga aaactcacgt taagggattt tggtcatgag      1140
attatcaaaa aggatcttca cctagatcct tttaaattaa aaatgaagtt ttaaatcaat      1200
ctaaagtata tatgagtaaa cttggtctga cagttaccaa tgcttaatca gtgaggcacc      1260
tatctcagcg atctgtctat ttcgttcatc catagttgcc tgactccccg tcgtgtagat      1320
aactacgata cgggagggct taccatctgg ccccagtgct gcaatgatac cgcgagaccc      1380
acgctcaccg gctccagatt tatcagcaat aaaccagcca gccggaaggg ccgagcgcag      1440
aagtggtcct gcaactttat ccgcctccat ccagtctatt aattgttgcc gggaagctag      1500
agtaagtagt tcgccagtta atagtttgcg caacgttgtt gccattgcta caggcatcgt      1560
ggtgtcacgc tcgtcgtttg gtatggcttc attcagctcc ggttcccaac gatcaaggcg      1620
agttacatga tcccccatgt tgtgcaaaaa agcggttagc tccttcggtc ctccgatcgt      1680
tgtcagaagt aagttggccg cagtgttatc actcatggtt atggcagcac tgcataattc      1740
tcttactgtc atgccatccg taagatgctt ttctgtgact ggtgagtact caaccaagtc      1800
attctgagaa tagtgtatgc ggcgaccgag ttgctcttgc ccggcgtcaa tacgggataa      1860
taccgcgcca catagcagaa ctttaaaagt gctcatcatt ggaaaacgtt cttcggggcg      1920
aaaactctca aggatcttac cgctgttgag atccagttcg atgtaaccca ctcgtgcacc      1980
caactgatct tcagcatctt ttactttcac cagcgtttct gggtgagcaa aaacaggaag      2040
gcaaaatgcc gcaaaaaagg gaataagggc gacacggaaa tgttgaatac tcatactctt      2100
cctttttcaa tattattgaa gcatttatca gggttattgt ctcatgagcg gatacatatt      2160
tgaatgtatt tagaaaaata aacaaatagg ggttccgcgc acatttcccc gaaaagtgcc      2220
acttgcatcg atgaattgat ccgaagttcc tattctctag aaagtatagg aacttcgaat      2280
tgtcgaggcc gcaataaaat atctttattt tcattacatc tgtgtgttgg ttttttgtgt      2340
gaatcgatag tactaacata cgctctccat caaaacaaaa cgaaacaaaa caaactagca      2400
aaataggctg tccccagtgc aagtgcaggt gccagaacat ttctctatcg ataggtaccg      2460
tcgacctatg gtgcactctc agtacaatct gctctgatgc cgcatagtta agccagtata      2520
cactccgcta tcgctacgtg actgggtcat ggctgcgccc cgacaccgc caacaccgc      2580 tgacgcgccc tgacgggctt gtctgctccc ggcatccgct tacagacaag ctgtgaccgt      2640
```

```
ctccgggagc tgcatgtgtc agaggttttc accgtcatca ccgaaacgcg cgaggcagcc    2700
ggccattatg cacgaccccg ccccgacgcc ggcacgccgg gggcccgtgg ccgcggcccg    2760
ttggtcgaac ccccggcccc gcccatccgc gccatctgcc atgggcgggg cgcgagggcg    2820
ggtgggtccg cgcccgccc cgcatggcat ctcattaccg cccgatccgg cggtttccgc     2880
ttccgttccg catgctaacg aggaacgggc aggggcggg gcccgggccc cgacttcccg     2940
gttcggcggt aatgagatac gagcccgcg cgcccgttgg ccgtccccgg ccccccggt     3000 cccgcccgcc ggacgccggg accaacggga cggcgggcgg cccaagggcc gcccgccttg    3060 ccgcccccc attggccggc gggcgggacc gccccaaggg ggcggggccg ccgggtaaaa     3120
gaagtgagaa cgcgaagcgt tcgcacttcg tcccaatata tatatattat tagggcgaag    3180
tgcgagcact ggcgccgtgc ccgactccgc gccggcccg gggcgggcc cgggcggcgg     3240 ggggcgggtc tctccggcgc acataaaggc ccggcgcgac cgacgcccgc agacggcgcc    3300
ggccacgaac gacgggagcg gctgcggagc acgcggaccg ggagcgggag tcgcagaggg    3360
ccgtcggagc ggacggcgtc ggcatcgcga cgccccggct cgggatcggg atcgcatcgg    3420
aaagggacac gcggacgcgg gggggaaaga cccgcccacc ccacccacga aacacagggg    3480
acgcaccccg ggggcctccg acgacagaaa cccaccggtc cgcctttttt gcacgggtaa    3540
gcaccttggg tgggcggagg agggggggac gcggggggtgg aggagggggg acgcgggggc   3600
ggaggagggg ggacgcgggg gcggaggagg ggggacgcgg gggcggagga gggggacgc    3660 ggggggcggag gagggggctc acccgcgttc gtgccttccc gcaggaggaa cgtcctcgtc   3720
gataagctag cgcggccgca tcgataagct tcgagctagg atgaggggcc aggccgccgc    3780
cccgggcccc gtctggatcc tcgcccgct gctactgctg ctgctgctgc tgggacgccg     3840
cgcgcgggcg gccgccggag cagacgcggg gcccgggccc gagccgtgcg ccacgctggt    3900
gcagggaaag ttcttcggct acttctccgg ggccgccgtg ttcccggcca acgcctcgcg    3960
ctgctcctgg acgctacgca acccggaccc gcggcgctac actctctaca tgaaggtggc   4020
caaggcgccc gtgccctgca gcggcccgg ccgcgtgcgc acctaccagt tcgactcctt    4080
cctcgagtcc acgcgcacct acctgggcgt ggagagcttc gacgaggtgc tgcggctctg   4140 cgaccccctcc gcaccctgg ccttcctgca ggccagcaag cagttcctgc agatgcggcg    4200
ccagcagccg ccccagcacg acgggctccg gccccgggcc gggccgccgg ccccaccga    4260 cgacttctcc gtggagtacc tggtggtggg gaaccgcaac cccagccgtg ccgcctgcca    4320
gatgctgtgc cgctggctgg acgcgtgtct ggccggtagt cgcagctcgc acccctgcgg    4380
gatcatgcag ccccctgcg cctgcctggg cggcgaggcg ggcggccctg ccgcgggacc    4440 cctggcccc cgcggggatg tctgcttgag agatgcggtg gctggtggcc ctgaaaactg    4500
cctcaccagc ctgacccagg accggggcgg gcacggcgcc acaggcggct ggaagctgtg    4560
gtccctgtgg ggcgaatgca cgcgggactg cggggaggc ctccagacgc ggacgcgcac    4620
ctgcctgccc gcgccgggcg tggagggcgg cggctgcgag ggggtgctgg aggagggtcg    4680
ccagtgcaac cgcgaggcct gcggccccgc tgggcgcacc agctcccgga ccagtccct    4740 gcggtccaca gatgcccggc ggcgcgagga gctgggggac gagctgcagc agtttgggtt    4800
cccagccccc cagaccggtg acccagcagc cgaggagtgg tccccgtgga gcgtgtgctc    4860
cagcacctgc ggcgagggct ggcagacccg cacgcgcttc tgcgtgtcct cctcctacag    4920
cacgcagtgc agcggacccc tgcgcgagca gcggctgtgc aacaactctg ccgtgtgccc    4980
agtgcatggt gcctgggatg agtggtcgcc ctggagcctc tgctccagca cctgtggccg    5040
```

```
tggctttcgg gatcgcacgc gcacctgcag gcccccccag tttgggggca acccctgtga   5100
gggccctgag aagcaaacca agttctgcaa cattgccctg tgccctggcc gggcagtgga   5160
tggaaactgg aatgagtggt cgagctggag cgcctgctcc gccagctgct cccagggccg   5220
acagcagcgc acgcgtgaat gcaacgggcc ttcctacggg ggtgcggagt gccagggcca   5280
ctgggtggag acccgagact gcttcctgca gcagtgccca gtggatggca agtggcaggc   5340
ctgggcgtca tggggcagtt gcagcgtcac gtgtggggct ggcagccagc gacgggagcg   5400
tgtctgctct gggcccttct tcggggagc agcctgccag gccccccagg atgagtaccg   5460
gcagtgcggc acccagcggt gtcccgagcc ccatgagatc tgtgatgagg acaactttgg   5520
tgctgtgatc tggaaggaga ccccagcggg agaggtggct gctgtccggt gtccccgcaa   5580
cgccacagga ctcatcctgc gacggtgtga gctggacgag gaaggcatcg cctactggga   5640
gcccccacc tacatccgct gtgtttccat tgactacaga acatccaga tgatgacccg   5700
ggagcacctg gccaaggctc agcgagggct gcctggggag ggggtctcgg aggtcatcca   5760
gacactggtg gagatctctc aggacgggac cagctacagt ggggacctgc tgtccaccat   5820
cgatgtcctg aggaacatga cagagatttt ccggagagcg tactacagcc ccaccccctgg   5880
ggacgtacag aactttgtcc agatccttag caacctgttg gcagaggaga atcgggacaa   5940
gtgggaggag gcccagctgg cgggcccaa cgccaaggga ctgttccggc tggtggagga   6000
ctttgtggac gtcatcggct tccgcatgaa ggacctgagg gatgcatacc aggtgacaga   6060
caacctggtt tcagcatcc ataagctccc agccagcgga gccactgaca tcagcttccc   6120
catgaagggc tggcgggcca cgggtgactg ggccaaggtg ccagaggaca gggtcactgt   6180
gtccaagagt gtcttctcca cggggctgac agaggccgat gaagcatccg tgtttgtggt   6240
gggcaccgtg ctctacagga acctgggcag cttcctggcc ctgcagagga acgaccgt   6300
cctgaattct aaggtgatct ccgtgactgt gaaaccccg cctcgctccc tgcgcacacc   6360
cttggagatc gagtttgccc acatgtataa tggcaccacc aaccagacct gtatcctgtg   6420
ggatgagacg gatgtaccct cctcctccgc ccccccgcag ctcgggccct ggtcgtggcg   6480
cggctgccgc acggtgcccc tcgacgccct ccggacgcgc tgcctctgtg accggctctc   6540
caccttcgat atcttaatca agcttggtac cgagctcgga tccactagtc cagtgtggtg   6600
gaattctgca gatatccagc acagtggcgg ccgctcgagt ctagagggcc gcggttcga   6660
acaaaactc atctcagaag aggatctgaa tatgcatacc ggtcatcatc accatcacca   6720
ttgagtttat ctctagagct gagaacttca gggtgagttt ggggacccct gattgttctt   6780
tcttttcgc tattgtaaaa ttcatgttat atggaggggg caaagtttc agggtgttgt   6840
ttagaatggg aagatgtccc ttgtatcacc atggaccctc atgataattt tgtttctttc   6900
actttctact ctgtt                                                     6915
```

<210> SEQ ID NO 11
<211> LENGTH: 4594
<212> TYPE: DNA
<213> ORGANISM: Artificial Sequence
<220> FEATURE:
<223> OTHER INFORMATION: plasmid containing Nestin enhancer driven
      ICP34.5
<220> FEATURE:
<221> NAME/KEY: misc_feature
<222> LOCATION: (808)..(812)
<223> OTHER INFORMATION: n is a,g, c, or t
<220> FEATURE:
<221> NAME/KEY: misc_feature
<222> LOCATION: (3155)..(3157)

<223> OTHER INFORMATION: n is a,g, c, or t

<400> SEQUENCE: 11

```
tgccgggaag ctagagtaag tagttcgcca gttaatagtt tgcgcaacgt tgttgccatt      60
gctacaggca tcgtggtgtc acgctcgtcg tttggtatgg cttcattcag ctccggttcc     120
caacgatcaa ggcgagttac atgatccccc atgttgtgca aaaaagcggt tagctccttc     180
ggtcctccga tcgttgtcag aagtaagttg gccgcagtgt tatcactcat ggttatggca     240
gcactgcata attctcttac tgtcatgcca tccgtaagat gcttttctgt gactggtgag     300
tactcaacca agtcattctg agaatagtgt atgcggcgac cgagttgctc ttgcccggcg     360
tcaatacggg ataataccgc gccacatagc agaactttaa aagtgctcat cattggaaaa     420
cgttcttcgg ggcgaaaact ctcaaggatc ttaccgctgt tgagatccag ttcgatgtaa     480
cccactcgtg cacccaactg atcttcagca tcttttactt tcaccagcgt ttctgggtga     540
gcaaaaacag gaaggcaaaa tgccgcaaaa aagggaataa gggcgacacg gaaatgttga     600
atactcatac tcttcctttt tcaatattat tgaagcattt atcagggtta ttgtctcatg     660
agcggataca tatttgaatg tatttagaaa aataaacaaa taggggttcc gcgcacattt     720
ccccgaaaag tgccacttgc atcgatgaat tgatccgaag ttcctattct ctagaaagta     780
taggaacttc gaattgtcga cggatccnnn nnccgcggaa gacccaggcc gcctcgggtg     840
taacgttaga ccgagttcgc cgggccggct ccgcgggcca gggcccgggc acgggcctcg     900
ggccccaggc acggcccgat gaccgcctcg gcctccgcca ccggcgccg gaaccgagcc     960
cggtcggccc gctcgcgggc ccacgagccg cggcgcgcca ggcgggcggc cgaggcccag    1020
accaccaggt ggcgcacccg gacgtggggc gagaagcgca cccgcgcggg ggtcgcgggg    1080
gtcgcggggg tcgcgggggt cgcggggggtc gcggggggct ccggcgcccc ctccccgccc    1140
gcgcgtcgca ggcgcaggcg cgccaggtgc tccgcggtga cgcgcaggcg gagggcgagg    1200
cgcggcggaa ggcggaaggg gcgcgagggg gggtgggagg ggtcagcccc gcccccgggg    1260
cccacgccgg gcggtggggg ccggggccgg gggcggcgg cggtgggccg ggcctctggc    1320
gccggctcgg gcgggggggct gtccggccag tcgtcgtcat cgtcgtcgtc ggacgcggac    1380
tcgggaacgt ggagccactg gcgcagcagc agcgaacaag aaggcggggg cccaccggcg    1440
gggggcggcg gcggggcggc cgcgggcgcg ctcctgaccg cgggttccga gttgggcgtg    1500
gaggttacct gggactgtgc ggttgggacg gcgcccgtgg gcccgggcgg ccggggggcgg    1560
cgggggccgc gatggcggcg gcggcgggcc atgatcaagc tcatgcgcc gcgctctgct    1620
tctggaaggc tgcgctccgc ggcgtggatg ctccggggaa agttgcgctc cgcggcaggg    1680
atgctcctgg gaaggttgcg ctccgcggca gggatgctct ggggaaggct ggtcctggcc    1740
gaggatcggg aacgcgccgc tcgctctgct tctcttgtct tcgcttgtct ctggatggaa    1800
ccagatttgg ttctgagtag ctgtcagcgt ctggtgacct gctcgccgcc ctgcgccttt    1860
aaggagtctt caccggcccc gcccactctc cgctgggcca atcagcgagc cggaggaggc    1920
cttgggccca ggaatcttcc agcagtttcg cgtctggtgg agcttccccg cctcccttga    1980
gtaatcggag ttgtgggttc cgcccttgtc cagaactctc cagaggtttc tggggttcac    2040
tggagagtac ggattcctga gggggagggt gtggggaagt gctggtgcta ctagtgacac    2100
tgttgctatg gcgacgcatt actaaggcct gtgtggaatg acaagaaag atcacctcta    2160
gctcggtgtt gtgtacagtt tgttgtgatt tgtggggttt cgccaactcg cacagttctg    2220
aatatggggg ttaaaggcta aaacttaagg gctaaaactt ctccccgcca agtttaggag    2280
```

```
acccagggag atgcctgggg gcgtgtccgg tgacgtgatc ctctccaatc gcgttacaat    2340
ggcagtgctg cctctgacct catggactaa tttaggaact agaggctctg tcccagcaca    2400
ggctcaaagt tgccgggagg ggcggggtgg ggggtggggg gaccccggc tgctcagttt     2460
ggatgttcct ggagctcggt acccgcgatc gcccctagag gatctactag tcatatgata   2520
agcctgaacc tcgtccaggt gtctgcaacc gagagttctc agcctccagc agagtcctgg   2580
tggggagtgg ggagataggg tcagctccag ctgaggtagc atgtcctgcc actgcaggat   2640
caatctctat tgtgaccatt gtcatataaa agccacacag tcatataccc acagatatat   2700
acttagccaa cccatatttg agacacaggg agacccaca tgcagattcc cacagtcgga    2760
ggcagggcca aatgaattgc taacacttat atcagactcc tcagatcagt ctccgcctcc   2820
ccacccaagg ccaaggccga tgacctcatc ctctgggagg gaggccgatt ctcatgctaa   2880
ttattgcctt ttgtccacac taccatctgg agggcctaag aagggagggc tcctcagggg   2940
aagtgggaat tctcaggctg ttcccagggg atggctctct ctctgccccc agagctggta   3000
acagacaaaa gcaaatgaat tcagctcccc ttctccaaat ccttttcaga cctcaaacgc   3060
cagtggttac attcctcaga gctgcctgga ccctttccct cagaggactg actgggctaa   3120
aagccctcat ctcaggatca caaactcttc agggnnngga tctcgagccc gggctagcac   3180
gcgtaagagc tcggtaccta tcgatagaga aatgttctgg cacctgcact tgcactgggg   3240
acagccatt ttgctagttt gttttgtttc gttttgtttt gatggagagc gtatgttagt    3300
actatcgatt cacacaaaaa accaacacac agatgtaatg aaaataaaga tattttattg   3360
cggccgatcc ggaacccta atataacttc gtataatgta tgctatacga agttattagg    3420
tccctcgacc tgcaggcatg gctaattctg tcagccgtta agtgttcctg tgtcactgaa   3480
aattgctttg agaggctcta agggcttctc agtgcgttac atccctggct tgttgtccac   3540
aaccgttaaa ccttaaaagc tttaaaagcc ttatatattc ttttttttct tataaaactt   3600
aaaaccttag aggctattta agttgctgat ttatattaat tttattgttc aaacatgaga   3660
gcttagtacg tgaaacatga gagcttagta cgttagccat gagagcttag tacgttagcc   3720
atgagggttt agttcgttaa acatgagagc ttagtacgtt aaacatgaga gcttagtacg   3780
tgaaacatga gagcttagta cgtactatca acaggttgaa ctgcggatct tgcggccggc   3840
cgcaatcggg caaatcgctg aatattcctt ttgtctccga ccatcaggca cctgagtcgc   3900
tgtcttttc gtgacattca gttcgctgcg ctcacggctc tggcagtgaa tgggggtaaa    3960
tggcactaca ggcgccttt atggattcat gcaaggaaac tcaaaataat acaagaaaag    4020
cccgtcacgg gcttctcagg gcgttttatg gcgggtctgc tatgtggtgc tatctgactt   4080
tttgctgttc agcagttcct gccctctgat tttccagtct gaccacttcg gattatcccg   4140
tgacaggtca ttcagactgg ctaatgcacc cagtaaggca gcggtatcat caacggggtc   4200
tgacgctcag tggaacgaaa actcacgtta agggattttg gtcatgagat tatcaaaaag   4260
gatcttcacc tagatccttt taaattaaaa atgaagtttt aaatcaatct aaagtatata   4320
tgagtaaact tggtctgaca gttaccaatg cttaatcagt gaggcaccta tctcagcgat   4380
ctgtctattt cgttcatcca tagttgcctg actccccgtc gtgtagataa ctacgatacg   4440
ggagggctta ccatctggcc ccagtgctgc aatgataccg cgagacccac gctcaccggc   4500
tccagattta tcagcaataa accagccagc cggaagggcc gagcgcagaa gtggtcctgc   4560
aactttatcc gcctccatcc agtctattaa ttgt                               4594

<210> SEQ ID NO 12
```

-continued

```
<211> LENGTH: 9292
<212> TYPE: DNA
<213> ORGANISM: Artificial Sequence
<220> FEATURE:
<223> OTHER INFORMATION: Plasmid with IE 4/5 - Vaculostatin with Nestin
      enhancer driven ICP34.5 cassette
<220> FEATURE:
<221> NAME/KEY: misc_feature
<222> LOCATION: (4736)..(4740)
<223> OTHER INFORMATION: n is a, t, g, or c
<220> FEATURE:
<221> NAME/KEY: misc_feature
<222> LOCATION: (7083)..(7085)
<223> OTHER INFORMATION: n is a, t, g, or c

<400> SEQUENCE: 12
ctagaaagta taggaacttc ccatagagcc caccgcatcc ccagcatgcc tgctattgtc      60
ttcccaatcc tcccccttgc tgtcctgccc caccccaccc ccagaataga atgacacctt     120
actcagacaa tgcgatgcaa tttcctcatt ttattaggaa aggacagtgg gagtggcacc     180
ttccagggtc aaggaaggca cggggggaggg gcaaacaaca gatggctggc aactagaagg     240
cacagtcgag gctgatcagc gggttttaaac tcaatggtga tggtgatgat gaccggtatg     300
catattcaga tcctcttctg agatgagttt ttgttcgaac cgcgggccct ctagactcga     360
gcggccgcca ctgtgctgga tatctgcaga attccaccac actggactag tggatccgag     420
ctcggtacca agcttgatta agatatcgaa ggtggagagc cggtcacaga ggcagcgcgt     480
ccggagggcg tcgaggggca ccgtgcggca gccgcgccac gaccagggcc cgagctgcgg     540
gggggcggag gaggagggta catccgtctc atcccacagg atacaggtct ggttggtggt     600
gccattatac atgtgggcaa actcgatctc caagggtgtg cgcagggagc gaggcggggg     660
tttcacagtc acgagatca ccttagaatt caggacggtc gtgttcctct gcagggccag     720
gaagctgccc aggttcctgt agagcacggt gcccaccaca aacacggatg cttcatcggc     780
ctctgtcagc cccgtggaga agacactctt ggacacagtg accctgtcct ctggcacctt     840
ggcccagtca cccgtggccc gccagccctt catggggaag ctgatgtcag tggctccgct     900
ggctgggagc ttatggatgc tgagaaccag gttgtctgtc acctggtatg catccctcag     960
gtccttcatg cggaagccga tgacgtccac aaagtcctcc accagccgga acagctcctt    1020
ggcgttgggg cccgccagct gggcctcctc ccacttgtcc cgattctcct ctgccaacag    1080
gttgctaagg atctggacaa agttctgtac gtccccaggg gtgggctgt agtacgctct    1140 ccggaaaatc tctgtcatgt tcctcaggac atcgatggtg gacagcaggt ccccactgta    1200
gctggtcccg tcctgagaga tctccaccag tgtctggatg acctccgaga cccctcccc    1260 aggcagccct cgctgagcct tggccaggtc ctcccgggtc atcatctgga tgtttctgta    1320
gtcaatggaa acacagcgga tgtaggtggg gggctcccag taggcgatgc cttcctcgtc    1380
cagctcacac cgtcgcagga tgagtcctgt ggcgttgcgg ggacaccgga cagcagccac    1440
ctctcccgct ggggtctcct tccagatcac agcaccaaag ttgtcctcat cacagatctc    1500
atggggctcg ggacaccgct gggtgccgca ctgccggtac tcatcctggg ggccctggca    1560
ggctgctccc ccgaagaagg gcccagagca gacacgctcc cgtcgctggc tgccagcccc    1620
acacgtgacg ctgcaactgc cccatgacgc ccaggcctgc cacttgccat ccactgggca    1680
ctgctgcagg aagcagtctc gggtctccac ccagtggccc tggcactccg caccccgta    1740 ggaaggcccg ttgcattcac gcgtgcgctg ctgtcggccc tgggagcagc tggcggagca    1800
ggcgctccag ctcgaccact cattccagtt tccatccact gccggccag gcacagggc    1860 aatgttgcag aacttggttt gcttctcagg gccctcacag gggttgcccc caaactgggg    1920
```

-continued

```
gggcctgcag gtgcgcgtgc gatcccgaaa gccacggcca caggtgctgg agcagaggct    1980
ccagggcgac cactcatccc aggcaccatg cactgggcac acggcagagt tgttgcacag    2040
ccgctgctcg cgcaggggtc cgctgcactg cgtgctgtag gaggaggaca cgcagaagcg    2100
cgtgcgggtc tgccagccct cgccgcaggt gctggagcac acgctccacg gggaccactc    2160
ctcggctgct gggtcaccgg tctgggggc tgggaaccca aactgctgca gctcgtcccc     2220
cagctcctcg cgccgccggg catctgtgga ccgcaggac tggctccggg agctggtgcg     2280
cccagcgggg ccgcaggcct cgcggttgca ctggcgaccc cctccagca ccccctcgca     2340 gccgccgccc tccacgcccg gcgcgggcag gcaggtgcgc gtccgcgtct ggaggcctcc    2400
cccgcagtcc cgcgtgcatt cgccccacag ggaccacagc ttccagccgc ctgtggcgcc    2460
gtgcccgccc cggtcctggg tcaggctggt gaggcagttt tcagggccac cagccaccgc    2520
atctctcaag cagacatccc cgcggggggc caggggtccc gcggcagggc cgcccgcctc    2580
gccgcccagg caggcgcagg gggtctgcat gatcccgcag gggtgcgagc tgcgactacc    2640
ggccagacac gcgtccagcc agcggcacag catctggcag gcggcacggc tggggttgcg    2700
gttccccacc accaggtact ccacggagaa gtcgtcggtg gggcccggcg ccccggcccg    2760
gggccggagc ccgtcgtgct ggggcggctg ctggcgccgc atctgcagga actgcttgct    2820
ggcctgcagg aaggccaggg gtgcggaggg gtcgcagagc cgcagcacct cgtcgaagct    2880
ctccacgccc aggtaggtgc gcgtggactc gaggaaggag tcgaactggt aggtgcgcac    2940
gcggccgggg ccgctgcagg gcacgggcgc cttggccacc ttcatgtaga gagtgtagcg    3000
ccgcgggtcc gggttgcgta gcgtccagga gcagcgcgag gcgttggccg ggaacacggc    3060
ggccgcggag aagtagccga agaactttcc ctgcaccagc gtggcgcacg gctcgggccc    3120
gggccccgcg tctgctccgg cggccgcccg cgcgcggcgt cccagcagca gcagcagcag    3180
tagcagcggg gcgaggatcc agacggggcc cggggcggcg gcctggcccc tcatcctagc    3240
tcgaagctta tcgatgcggc cgcgctagct tatcgacgag gacgttcctc ctgcgggaag    3300
gcacgaacgc gggtgagccc cctcctccgc ccccgcgtcc cccctcctcc gccccgcgt    3360 cccccctcct ccgcccccgc gtcccccctc ctccgccccc gcgtccccc tcctccaccc     3420 ccgcgtcccc ccctcctccg cccacccaag gtgcttaccc gtgcaaaaaa ggcggaccgg    3480
tgggtttctg tcgtcggagg ccccccggggt gcgtcccctg tgtttcgtgg gtggggtggg    3540
cgggtctttc ccccccgcgt ccgcgtgtcc ctttccgatg cgatcccgat cccgagccgg    3600
ggcgtcgcga tgccgacgcc gtccgctccg acggccctct gcgactcccg ctcccggtcc    3660
gcgtgctccg cagccgctcc cgtcgttcgt ggccggcgcc gtctgcgggc gtcggtcgcg    3720
ccgggccttt atgtgcgccg gagagacccg ccccccgccg cccggggcccg ccccggggc     3780 cggcgcggag tcgggcacgg cgccagtgct cgcacttcgc cctaataata tatatatt     3840 gggacgaagt gcgaacgctt cgcgttctca cttcttttac ccggcggccc cgccccttg     3900 gggcggtccc gcccgccggc caatgggggg gcggcaaggc gggcggccct tgggccgccc    3960
gccgtcccgt tggtcccggc gtccggcggg cgggaccggg gggcccgggg acggccaacg    4020
ggcgcgcggg gctcgtatct cattaccgcc gaaccgggaa gtcggggccc gggcccgcc     4080 ccctgccgt tcctcgttag catgcggaac ggaagcggaa accgcggat cgggcggtaa      4140 tgagatgcca tgcggggcgg ggcggggacc cacccgccct cgcgcccgc ccatggcaga     4200 tggcgcggat gggcggggcc gggggttcga ccaacgggcc gcggccacgg gccccggcg     4260 tgccggcgtc ggggcggggt cgtgcataat ggccggctgc ctcgcgcgtt tcggtgatga    4320
```

```
cggtgaaaac ctctgacaca tgcagctccc ggagacggtc acagcttgtc tgtaagcgga    4380
tgccgggagc agacaagccc gtcagggcgc gtcagcgggt gttggcgggt gtcgggcgc     4440 agccatgacc cagtcacgta gcgatagcgg agtgtatact ggcttaacta tgcggcatca    4500
gagcagattg tactgagagt gcaccatagg tcgacggtac ctatcgatag agaaatgttc    4560
tggcacctgc acttgcactg gggacagcct atttttgctag tttgttttgt ttcgttttgt   4620
tttgatggag agcgtatgtt agtactatcg attcacacaa aaaaccaaca cacagatgta    4680
atgaaaataa agatatttta ttgcggcctc gacaattcga attgtcgacg gatccnnnnn    4740
ccgcggaaga cccaggccgc ctcgggtgta acgttagacc gagttcgccg ggccggctcc    4800
gcgggccagg gcccgggcac gggcctcggg ccccaggcac ggcccgatga ccgcctcggc    4860
ctccgccacc cggcgccgga accgagcccg gtcggcccgc tcgcgggccc acgagccgcg    4920
gcgcgccagg cgggcggccg aggcccagac caccaggtgg cgcacccgga cgtggggcga    4980
gaagcgcacc cgcgcggggg tcgcggggt cgcggggtc gcggggtcg cggggtcgc        5040 gggggctcc ggcgccccct ccccgcccgc gcgtcgcagg cgcaggcgcg ccaggtgctc     5100
cgcggtgacg cgcaggcgga gggcgaggcg cggcggaagg cggaagggc gcgagggggg     5160 gtgggagggg tcagccccgc cccccgggcc cacgccgggc ggtgggggcc ggggccgggg    5220
ggcggcggcg gtgggccggg cctctggcgc cggctcgggc gggggctgt ccggccagtc     5280 gtcgtcatcg tcgtcgtcgg acgcggactc gggaacgtgg agccactggc gcagcagcag    5340
cgaacaagaa ggcgggggcc caccggcggg gggcggcggc ggggcggccg cgggcgcgct    5400
cctgaccgcg ggttccgagt tgggcgtgga ggttacctgg gactgtgcgg ttgggacggc    5460
gcccgtgggc ccggccggcc ggggcggcg gggccgcga tggcggcggc ggcgggccat      5520
gatcaagctc atggcgccgc gctctgcttc tggaaggctg cgctccgcgg cgtggatgct    5580
ccggggaaag ttgcgctccg cggcagggat gctcctggga aggttgcgct ccgcggcagg    5640
gatgctctgg ggaaggctgg tcctggccga ggatcgggaa cgcgccgctc gctctgcttc    5700
tcttgtcttc gcttgtctct ggatggaacc agatttggtt ctgagtagct gtcagcgtct    5760
ggtgacctgc tcgccgccct gcgcctttaa ggagtcttca ccggccccgc ccactctccg    5820
ctgggccaat cagcgagccg gaggaggcct tggggccagg aatcttccag cagtttcgcg    5880
tctggtggag cttccccgcc tcccttgagt aatcggagtt gtgggttccg cccttgtcca    5940
gaactctcca gaggtttctg gggttcactg gagagtacgg attcctgagg gggagggtgt    6000
ggggaagtgc tggtgctact agtgacactg ttgctatggc gacgcattac taaggcctgt    6060
gtggaatgga caagaaagat cacctctagc tcggtgttgt gtacagtttg ttgtgatttg    6120
tggggtttcg ccaactcgca cagttctgaa tatgggggtt aaaggctaaa acttaagggc    6180
taaaacttct ccccgccaag tttaggagac ccagggagat gcctggggc gtgtccggtg     6240 acgtgatcct ctccaatcgc gttacaatgg cagtgctgcc tctgacctca tggactaatt    6300
taggaactag aggctctgtc ccagcacagg ctcaaagttg ccgggagggg cgggtgggg     6360 ggtgggggg accccggctg ctcagtttgg atgttcctgg agctcggtac ccgcgatcgc     6420
ccctagagga tctactagtc atatgataag cctgaacctc gtccaggtgt ctgcaaccga    6480
gagttctcag cctccagcag agtcctggtg gggagtgggg agatagggtc agctccagct    6540
gaggtagcat gtcctgccac tgcaggatca atctctattg tgaccattgt catataaaag    6600
ccacacagtc ataccccac agatatatac ttagccaacc catatttgag acacaggag      6660 accccacatg cagattccca cagtcggagg cagggccaaa tgaattgcta acacttatat    6720
```

```
cagactcctc agatcagtct ccgcctcccc acccaaggcc aaggccgatg acctcatcct   6780
ctgggaggga ggccgattct catgctaatt attgcctttt gtccacacta ccatctggag   6840
ggcctaagaa gggagggctc ctcaggggaa gtgggaattc tcaggctgtt cccaggggat   6900
ggctctctct ctgccccccag agctggtaac agacaaaagc aaatgaattc agctcccctt   6960
ctccaaatcc ttttcagacc tcaaacgcca gtggttacat tcctcagagc tgcctggacc   7020
cttcccctca gaggactgac tggggctaaa gccctcatct caggatcaca aactcttcag   7080
ggnnnggatc tcgagcccgg gctagcacgc gtaagagctc ggtacctatc gatagagaaa   7140
tgttctggca cctgcacttg cactggggac agcctatttt gctagtttgt tttgtttcgt   7200
tttgttttga tggagagcgt atgttagtac tatcgattca cacaaaaaac caacacacag   7260
atgtaatgaa aataaagata ttttattgcg gccgatccgg aacccttaat ataacttcgt   7320
ataatgtatg ctatacgaag ttattaggtc cctcgacctg caggcatggc taattctgtc   7380
agccgttaag tgttcctgtg tcactgaaaa ttgctttgag aggctctaag ggcttctcag   7440
tgcgttacat ccctggcttg ttgtccacaa ccgttaaacc ttaaaagctt taaaagcctt   7500
atatattctt ttttttctta taaaacttaa aaccttagag gctatttaag ttgctgattt   7560
atattaattt tattgttcaa acatgagagc ttagtacgtg aaacatgaga gcttagtacg   7620
ttagccatga gagcttagta cgttagccat gagggtttag ttcgttaaac atgagagctt   7680
agtacgttaa acatgagagc ttagtacgtg aaacatgaga gcttagtacg tactatcaac   7740
aggttgaact gcggatcttg cggccggccg caatcgggca aatcgctgaa tattcctttt   7800
gtctccgacc atcaggcacc tgagtcgctg tcttttcgt gacattcagt tcgctgcgct   7860
cacggctctg gcagtgaatg ggggtaaatg gcactacagg cgccttttat ggattcatgc   7920
aaggaaactc aaaataatac aagaaaagcc cgtcacgggc ttctcagggc gttttatggc   7980
gggtctgcta tgtggtgcta tctgactttt tgctgttcag cagttcctgc cctctgattt   8040
tccagtctga ccacttcgga ttatcccgtg acaggtcatt cagactggct aatgcaccca   8100
gtaaggcagc ggtatcatca acggggtctg acgctcagtg gaacgaaaac tcacgttaag   8160
ggattttggt catgagatta tcaaaaagga tcttcaccta gatccttttta aattaaaaat   8220 gaagttttaa atcaatctaa agtatatatg agtaaacttg gtctgacagt taccaatgct   8280
taatcagtga ggcacctatc tcagcgatct gtctatttcg ttcatccata gttgcctgac   8340
tccccgtcgt gtagataact acgatacggg agggcttacc atctggcccc agtgctgcaa   8400
tgataccgcg agacccacgc tcaccggctc cagatttatc agcaataaac cagccagccg   8460
gaagggccga gcgcagaagt ggtcctgcaa ctttatccgc ctccatccag tctattaatt   8520
gttgccggga agctagagta agtagttcgc cagttaatag tttgcgcaac gttgttgcca   8580
ttgctacagg catcgtggtg tcacgctcgt cgtttggtat ggcttcattc agctccggtt   8640
cccaacgatc aaggcgagtt acatgatccc ccatgttgtg caaaaaagcg gttagctcct   8700
tcggtcctcc gatcgttgtc agaagtaagt tggccgcagt gttatcactc atggttatgg   8760
cagcactgca taattctctt actgtcatgc catccgtaag atgcttttct gtgactggtg   8820
agtactcaac caagtcattc tgagaatagt gtatgcggcg accgagttgc tcttgcccgg   8880
cgtcaatacg ggataatacc gcgccacata gcagaacttt aaaagtgctc atcattggaa   8940
aacgttcttc ggggcgaaaa ctctcaagga tcttaccgct gttgagatcc agttcgatgt   9000
aacccactcg tgcacccaac tgatcttcag catcttttac tttcaccagc gtttctgggt   9060
gagcaaaaac aggaaggcaa aatgccgcaa aaaagggaat aagggcgaca cggaaatgtt   9120
```

```
gaatactcat actcttcctt tttcaatatt attgaagcat ttatcagggt tattgtctca    9180
tgagcggata catatttgaa tgtatttaga aaaataaaca aatagggtt ccgcgcacat     9240 ttccccgaaa agtgccactt gcatcgatga attgatccga agttcctatt ct           9292
```